US012570969B2

(12) United States Patent (10) Patent No.: US 12,570,969 B2
Sakamoto et al. (45) Date of Patent: Mar. 10, 2026

(54) PYRROLYSYL-tRNA SYNTHETASE

(71) Applicant: RIKEN, Saitama (JP)

(72) Inventors: Kensaku Sakamoto, Saitama (JP);
Atsushi Yamaguchi, Saitama (JP);
Fumie Kimura, Saitama (JP);
Shigeyuki Yokoyama, Saitama (JP);
Tatsuo Yanagisawa, Saitama (JP); **Eiko
Seki, Saitama (JP); Mitsuo Kuratani**,
Saitama (JP)

(73) Assignee: RIKEN, Saitama (JP)

( * ) Notice: Subject to any disclaimer, the term of this
patent is extended or adjusted under 35
U.S.C. 154(b) by 448 days.

(21) Appl. No.: 17/271,818

(22) PCT Filed: Aug. 30, 2019

(86) PCT No.: PCT/JP2019/034233
§ 371 (c)(1),
(2) Date: Feb. 26, 2021

(87) PCT Pub. No.: WO2020/045656
PCT Pub. Date: Mar. 5, 2020

(65) Prior Publication Data
US 2021/0324363 A1 Oct. 21, 2021

(30) Foreign Application Priority Data

Aug. 31, 2018 (JP) ................................. 2018-163967
Apr. 19, 2019 (JP) ................................. 2019-080459
Jul. 19, 2019 (JP) ................................. 2019-134129

(51) Int. Cl.
*C12N 9/00* (2006.01)
*C12P 21/00* (2006.01)
(52) U.S. Cl.
CPC ................ *C12N 9/93* (2013.01); *C12P 21/00*
(2013.01); *C12Y 601/01026* (2013.01)
(58) Field of Classification Search
CPC . C12N 9/93; C12P 21/00; C12P 21/02; C12Y
601/01026
See application file for complete search history.

(56) References Cited

U.S. PATENT DOCUMENTS

| | | | | |
|---|---|---|---|---|
| 8,735,093 B2 * | 5/2014 | Yokoyama | .............. | C12P 21/02 |
| | | | | 435/325 |
| 2010/0184134 A1 | 7/2010 | Voloshin et al. | | |
| 2010/0184135 A1 | 7/2010 | Voloshin et al. | | |
| 2010/0267087 A1 | 10/2010 | Yokoyama et al. | | |
| 2010/0304431 A1 | 12/2010 | Yokoyama et al. | | |
| 2011/0136168 A1 | 6/2011 | Yokoyama et al. | | |
| 2014/0322751 A1 | 10/2014 | Yokoyama et al. | | |
| 2016/0176811 A1 | 6/2016 | Marelli et al. | | |
| 2017/0292139 A1 | 10/2017 | Alfonta et al. | | |
| 2019/0127488 A1 | 5/2019 | Sakamoto et al. | | |

FOREIGN PATENT DOCUMENTS

| | | | | |
|---|---|---|---|---|
| JP | 2012-514979 A | 7/2012 | | |
| JP | 2016-534099 A | 11/2016 | | |
| WO | WO-2009/038195 A1 | 3/2009 | | |
| WO | WO-2009/066761 A1 | 5/2009 | | |
| WO | WO-2010/083148 A1 | 7/2010 | | |
| WO | WO-2017/030156 A1 | 2/2017 | | |
| WO | PCT/EP2018/058731 | * 4/2018 | .............. | C12N 9/00 |
| WO | WO 2018/185222 A1 | * 10/2018 | .............. | C12N 9/00 |

OTHER PUBLICATIONS

Broun et al., Catalytic plasticity of fatty acid modification enzymes
underlying chemical diversity of plant lipids. Science, 1998, vol.
282: 1315-1317. (Year: 1998).*
Devos et al., Practical limits of function prediction. Proteins:
Structure, Function, and Genetics. 2000, vol. 41: 98-107. (Year:
2000).*
Ryu et al., Efficient incorporation of unnatural amino acids into
proteins in *Escherichia coli*. Nat. Methods., 2006, vol. 3(4): 263-
265. (Year: 2006).*
Seffernick et al., Melamine deaminase and Atrazine chlorohydrolase:
98 percent identical but functionally different. J. Bacteriol., 2001,
vol. 183 (8): 2405-2410. (Year: 2001).*
Whisstock et al., Prediction of protein function from protein sequence.
Q. Rev. Biophysics., 2003, vol. 36 (3): 307-340. (Year: 2003).*
Witkowski et al., Conversion of b-ketoacyl synthase to a Malonyl
Decarboxylase by replacement of the active cysteine with gluta-
mine. Biochemistry, 1999, vol. 38: 11643-11650. (Year: 1999).*

(Continued)

*Primary Examiner* — Ganapathirama Raghu
(74) *Attorney, Agent, or Firm* — Clark & Elbing LLP

(57) ABSTRACT

Obtained is: a method for efficiently producing a polypep-
tide containing a non-canonical amino acid; a method for
incorporating a non-canonical amino acid into a polypep-
tide; a method for producing tRNA bound to a non-canonical
amino acid; a non-canonical amino acid incorporation sys-
tem; a material for use in these methods; or the like. Used
is a method for producing a polypeptide containing a non-
canonical amino acid, comprising: a step of contacting
PylRS from an organism belonging to the order Methano-
massiliicoccales or Thermoplasmatales with the non-canoni-
cal amino acid; and an incorporation step selected from step
(a) of incorporating the non-canonical amino acid into the
polypeptide with higher efficiency than in a case of using a
cell-free protein synthesis system with PylRS of *Metha-
nosarcina mazei* (MmPylRS) or step (b) of incorporating the
non-canonical amino acid into the polypeptide with higher
efficiency than in a case of using an *Escherichia coli* protein
synthesis system with a vector carrying a gene for the PylRS
under regulation by a glmS promoter or a case of using an
*Escherichia coli* protein synthesis system with a vector
carrying a gene for the PylRS under regulation by a glnS
promoter. Alternatively, used is a non-canonical amino acid
incorporation system containing highly concentrated PylRS
from an organism belonging to the order Methanomassiliic-
occales or Thermoplasmatales.

8 Claims, 25 Drawing Sheets

Specification includes a Sequence Listing.

(56) References Cited

OTHER PUBLICATIONS

Zeng et al., NagR Differentially Regulates the Expression of the glmS and nagAB Genes Required for Amino Sugar Metabolism by *Streptococcus mutans*. J. Bacteriol., 2015, vol. 197(22): 3533-3544. (Year: 2015).*

NovoPro: pKW vector (V016297), 6 pages, dated Nov. 1, 2024. (Year: 2024).*

Robertson WE., Repurposing the Translational Machinery to Incorporate Backbone-Modified Substrates. Ph.D., Thesis, Yale Univ., 2017, pp. 1-194 (Year: 2017).*

Willis et al., Mutually orthogonal pyrrolysyl-tRNA synthetase/tRNA pairs, Supplementary Information. Nature, 2018, vol. 10, pp. 1-18 (Year: 2018).*

Seki et al., Cell-Free synthesis for multiple site-specific incorporation of noncanonical amino acids using cell extracts from RF-1 deletion *E. coli* strains. Methods and Protocols, Methods in Molecular Biology, 2018, vol. 1728: 49-65 (Year: 2018).*

Herring et al., "The amino-terminal domain of pyrrolysyl-tRNA synthetase is dispensable in vitro but required for in vivo activity," FEBS Lett. 581(17):3197-3203 (2007) (14 pages).

Hohsaka et al., "Incorporation of nonnatural amino acids into proteins in cell-free translation systems," Journal of Japanese Biochemical Society 79(3):247-253 (2007).

International Search Report mailed Nov. 26, 2019, for PCT International Application No. PCT/JP2019/034233, Sakamoto et al., "Pyrrolysyl-tRNA Synthetase," Aug. 30, 2018 (2 pages).

Jiang et al., "PylSn and the homologous N-terminal domain of pyrrolysyl-tRNA synthetase bind the tRNA that is essential for the genetic encoding of pyrrolysine," J. Biol. Chem. 287(39):32738-32746 (2012).

Kanamori et al., "Cell-free translation system: Development in biochemistry and advance in synthetic biology," Journal of Japanese Biochemical Society 89(2):211-220 (2017).

Suzuki et al., "Crystal structures reveal an elusive functional domain of pyrrolysyl-tRNA synthetase," Nat. Chem. Biol. 13(12):1261-1266 (2017) (21 pages).

Willis et al., "Mutually orthogonal pyrrolysyl-tRNA synthetase/tRNA pairs," Nat. Chem. 10(8):831-837 (2018) (25 pages).

Yamaguchi et al., "Pyrrolysyl-tRNA synthetase with a unique architecture enhances the availability of lysine derivatives in synthetic genetic codes," Molecules 23(10):2460 (2018) (14 pages).

Extended European Search Report dated May 19, 2022, for European Patent Application No. 19854542.8, Sakamoto et al., "Pyrrolysyl-tRNA Synthetase," filed Aug. 30, 2019 (11 pages).

UniProt Accession No. M9SC49, "SubName: Full=Pyrrolysyl-tRNA synthetase {ECO:0000313 EMBL:AGI85861.1}; EC=6.1.1.26 {ECO:0000313 | EMBL:AGI85861.1};" last modified Jan. 19, 2022 (2013); Jun. 26, 2013 (1 page).

Arbely et al., "Photocontrol of tyrosine phosphorylation in mammalian cells via genetic encoding of photocaged tyrosine," J Am Chem Soc. 134(29):11912-5 (Jul. 2012).

Chen et al., "A facile system for encoding unnatural amino acids in mammalian cells," Angew Chem Int Ed Engl. 48(22):4052-5 (2009).

Engelke et al., "Control of protein function through optochemical translocation," ACS Synth Biol. 3(10):731-6 (Feb. 2014).

Erickson et al., "Precise photoremovable perturbation of a virus-host interaction," Angew Chem Int Ed Engl. 56(15):4234-7 (Mar. 2017).

Gautier et al., "Genetically encoded photocontrol of protein localization in mammalian cells," J Am Chem Soc. 132(12):4086-8 (Mar. 2010).

Gautier et al., "Light-activated kinases enable temporal dissection of signaling networks in living cells," J Am Chem Soc. 133(7):2124-7 (Jan. 2011).

Hemphill et al., "Genetically encoded light-activated transcription for spatiotemporal control of gene expression and gene silencing in mammalian cells," J Am Chem Soc. 135(36):13433-9 (Aug. 2013).

Hemphill et al., "Optical control of CRISPR/Cas9 gene editing," J Am Chem Soc. 137(17):5642-5 (Apr. 2015).

Liaunardy-Jopeace et al., "Encoding optical control in LCK kinase to quantitatively investigate its activity in live cells," Nat Struct Mol Biol. 24(12):1155-63 (Oct. 2017) (14 pages).

Liu et al., "Genetic code expansion in zebrafish embryos and its application to optical control of cell signaling," J Am Chem Soc. 139(27):9100-3 (Jun. 2017).

Luo et al., "Genetic encoding of photocaged tyrosines with improved light-activation properties for the optical control of protease function," Chembiochem. 18(14):1442-7 (Jun. 2017).

Luo et al., "Genetically encoded optical activation of DNA recombination in human cells," Chem Commun. 52(55):8529-32 (Jun. 2016).

Luo et al., "Genetically encoded optochemical probes for simultaneous fluorescence reporting and light activation of protein function with two-photon excitation," J Am Chem Soc. 136(44):15551-8 (Oct. 2014).

Mukai et al., "Reassignment of a rare sense codon to a non-canonical amino acid in *Escherichia coli*," Nucleic Acids Res. 43(16):8111-22 (Aug. 2015).

Nguyen et al., "Genetic encoding of photocaged cysteine allows photoactivation of TEV protease in live mammalian cells," J Am Chem Soc. 136(6): 2240-2243 (Jan. 2014).

Tharp et al., "Genetic incorporation of seven ortho-substituted phenylalanine derivatives," ACS Chem Biol. 9(4):884-90 (Jan. 2014).

Tuley et al., "The genetic incorporation of thirteen novel non-canonical amino acids," Chem Commun. 50(20):2673-5 (Mar. 2014).

Uprety et al., "Genetic encoding of caged cysteine and caged homocysteine in bacterial and mammalian cells," Chembiochem. 15(12):1793-9 (Jun. 2014).

Walker et al., "Photoactivation of mutant isocitrate dehydrogenase 2 reveals rapid cancer-associated metabolic and epigenetic changes," J Am Chem Soc. 138(3):718-21 (Jan. 2016).

Wan et al., "Pyrrolysyl-tRNA synthetase: an ordinary enzyme but an outstanding genetic code expansion tool," Biochim Biophys Acta. 1844(6):1059-70 (Jun. 2014).

Wang et al., "A rationally designed pyrrolysyl-tRNA synthetase mutant with a broad substrate spectrum," J Am Chem Soc. 134(6):2950-3 (Feb. 2012).

Wang et al., "Genetic incorporation of twelve meta-substituted phenylalanine derivatives using a single pyrrolysyl-tRNA synthetase mutant," ACS Chem Biol. 8(2):405-15 (Nov. 2012).

Wang et al., "The de novo engineering of pyrrolysyl-tRNA synthetase for genetic incorporation of L-phenylalanine and its derivatives," Mol Biosyst. 7(3):714-7 (Jan. 2011).

Welegedara et al., "Site-specific incorporation of selenocysteine by genetic encoding as a photocaged unnatural amino acid," Bioconjug Chem. 29(7):2257-64 (Jul. 2018).

Xiao et al., "Genetic incorporation of histidine derivatives using an engineered pyrrolysyl-tRNA synthetase," ACS Chem Biol. 9(5):1092-6 (Mar. 2014).

Office Action dated Aug. 15, 2023 for Chinese Patent Application No. 201980056281.3, Sakamoto et al., "Pyrrolysyl-tRNA Synthetase," filed Aug. 30, 2019 (English translation) (11 pages).

Office Action dated Mar. 26, 2024, for Japanese Patent Application No. 2020-539647, Sakamoto et al., "Pyrrolysyl-tRNA Synthetase," filed Aug. 30, 2019 (English machine translation) (14 pages).

UniProt Accession No. A0A126QV54, "SubName: Full=Pyrrolysyl-tRNA synthetase PylS {ECO:0000313 | EMBL:AMK13702.1};" sequence version 1: May 11, 2016, last modified Jun. 7, 2017 (2016) (1 page).

UniProt Accession No. M9SC49, "SubName: Full=Pyrrolysyl-tRNA synthetase {ECO:0000313 EMBL:AGI85861.1}; EC=6.1.1.26 {ECO:0000313 | EMBL:AGI85861.1};" sequence version 1: Jun. 26, 2013, last modified Mar. 28, 2018 (2013) (1 page).

Yokogawa, "Designing novel functions of proteins by using an artificial genetic code dictionary," A Grant-in-Aid for Scientific Research Subsidies Research Result Report (2011) (English abstract) (6 pages).

(56) References Cited

OTHER PUBLICATIONS

Yoshisaka et al., "Development of synthetic biology," Biochemistry. 79(3):247-53 (2007).

Deuschle et al., "Promoters of *Escherichia coli*: a hierarchy of in vivo strength indicates alternate structures," EMBO J. 5(11):2987-94 (Nov. 1986).

Kato et al., "Extensive Survey of Antibody Invariant Positions for Efficient Chemical Conjugation Using Expanded Genetic Codes," Bioconjug Chem. 28(8):2099-108 (Epub Jul. 2017).

Mukai et al., "Adding I-lysine derivatives to the genetic code of mammalian cells with engineered pyrrolysyl-tRNA synthetases," Biochem Biophys Res Commun. 371(4):818-22 (Epub May 2008) (includes suppl. content) (18 pages).

Mukai et al., "Genetic-code evolution for protein synthesis with non-natural amino acids," Biochem Biophys Res Commun. 411(4):757-61 (Epub Jul. 2011).

Odoi et al., "Nonsense and sense suppression abilities of original and derivative Methanosarcina mazei pyrrolysyl-tRNA synthetase-tRNA(Pyl) pairs in the *Escherichia coli* BL21(DE3) cell strain," PLoS One. 8(3):e57035 (Epub Mar. 2013) (11 pages).

Yanagisawa et al., "Multiple site-specific installations of N[epsilon]-monomethyl-L-lysine into histone proteins by cell-based and cell-free protein synthesis," Chembiochem. 15(12):1830-8 (Epub Jul. 2014).

Hong et al., "Cell-free protein synthesis from a release factor 1 deficient *Escherichia coli* activates efficient and multiple site-specific nonstandard amino acid incorporation," ACS Synth Biol. 3(6):398-409 (Epub Jan. 2014, published Dec. 13, 2013).

Supporting Information for Hong et al., "Cell-free protein synthesis from a release factor 1 deficient *Escherichia coli* activates efficient and multiple site-specific nonstandard amino acid incorporation," ACS Synth Biol. 3(6):398-409 (Epub Jan. 2014, published Dec. 13, 2013), (6 pages).

* cited by examiner

Fig. 2

```
M.barkeri    MDKKPLDVLISATGLWMSRTGTLHKIKHHEVSRSKIYIEMACGDHLVVNNSRSCRTARAF 60
M.mazei      MDKKPLNTLISATGLWMSRTGTIHKIKHHEVSRSKIYIEMACGDHLVVNNSRSSRTARAL 60
D.hafniense  ------------------------------------------------------------ 0
M.alvus      ------------------------------------------------------------ 0
ISO4-G1      ------------------------------------------------------------ 0

M.barkeri    RHHKYRKTCKRCRVSDEDINNFLTRSTESKNSVKVRVVSAPK-VKKAMPKSVSRAPKPLE 119
M.mazei      RHHKYRKTCKRCRVSDEDLNKFLTKANEDQTSVKVKVVSAPTRTKKAMPKSVARAPKPLE 120
D.hafniense  ------------------------------------------------------------ 0
M.alvus      ------------------------------------------------------------ 0
ISO4-G1      ------------------------------------------------------------ 0

M.barkeri    NSVSAKASTNTSRSVPSP----------------------------------AKSTPNSS 145
M.mazei      NTEAAQAQPSGSKFSPAIPVSTQESVSVPASVSTSISSISTGATASALVKGNTNPITSMS 180
D.hafniense  ------------------------------------------------------------ 0
M.alvus      ------------------------------------------------------------ 0
ISO4-G1      ------------------------------------------------------------ 0

M.barkeri    VPASAPAPSLTRSQL  VEALLSPED------KISLNMAKPFRELEPELV RRKND R  199
M.mazei      APVQASAPALTKSQT  EVLLNPKD------EISLNSGKPFRELESELL RRKKD  Q  234
D.hafniense  -----MSSSWTKVQY  KELNASGEQLEMGFSDALSRDRAFQGIEHQLM QGKRH  QL   55
M.alvus      -----MTVKYTDAQI  REYGN-GTYEQKVFEDLASRDAA SKEMSVAS DNEKK  KG   54
ISO4-G1      -----MVVKFTDSQI  MEYGD-NDWSEAEFEDAAARDKE SSQFSKLK ANDKG  KD   54
                *   *  ::: .          .      *          :  .. :: :

M.barkeri    YTNDREDYLGKLERD TKFFVDRGF  KSPI PAEYVE MGIN DTELSKQ FRVDK  259
M.mazei      YAEERENYLGKLERE TRFFVDRGF  KSPI PLEYIE MGID DTELSKQ FRVDK  294
D.hafniense  RTVKYRPALLELEEK AKALHQQGF  VTPT TKSA A MTIG DHPLFSQ FW DG  115
M.alvus      IANPSRHGLTQLMND ADALVAEGF  RTPI SKDA A MTIT DKPLFKQ FW DE  114
ISO4-G1      IANPR-NDLTDLENK REKLAARGF  HTPI VSKSA A MTIT DHPLFKQ FW DD  113
                :      * ,* ,,:   :  .**::: :* ::  . : :* * :*  * .*:* :*  :

M.barkeri    LCLRPMLAPTLYNYL RKLDRILPGP  IFEVGPCYRKESDGKEHL EFTM   C GSGC 319
M.mazei      FCLRPMLAPNLYNYL RKLDRALPDP  IFE GPCYRKESDGKEHL EFTM   C GSGC 354
D.hafniense  KCLRPMLAPNLYTL  ELERLWDKP  IFE GTC RKESQGAQHL EFTM   T GTPL 175
M.alvus      RALRPMLAPNLYSVM DLRDHTDGP K IFE GSC RKESHSGMHL EFTM   V GPRG 174
ISO4-G1      RALRPMHAMNLYKVM ELRDHTKGP  IFE GSC RKESKSSTHL EFTM   V GPDG 173
                .****  * .**. *.*      *;:***:* *;****.. **;****:*. ;:*

M.barkeri    T--RENLEALIKEF DYLE -DFEIVG SCMV G T D MHGDLE SSAV GFVPLDREW 376
M.mazei      T--RENLESIITDF NHLG -DFKIVG SCMV G T D MHGDLE SSAV GFIPLDREW 411
D.hafniense  EERH RLGDMARWV EAAG RE ELVT SSVV G T D MKGDLE ASGA HFLDEKW 235
M.alvus      D-AT VLKNYISVV KAAG P DLVQ ESDV KET D EINGQE CSAA GFHY DAAH 233
ISO4-G1      D-PM HLKMYIGDI DAVG - TTSRE ESDV V T D EINGTE ASGA GFHK DPAH 231
                : *       .:.   : ::   :.. ** :*:*:  .. *:.*..:** **

M.barkeri    G DKPWIGAGFGLERLLK VMHGFKNI RASRSE YY GISTL- 419   SEQ ID NO:11
M.mazei      G DKPWIGAGFGLERLLK VKHDFKNI RAARSG YY GISTL- 454   SEQ ID NO:4
D.hafniense  E FDPWVGLGFGLERLLM REGTQHV SMARSL YL GVRLNIN 279   SEQ ID NO:12
M.alvus      D HEPWSGAGFGLERLLT REKYSTV KGGASI YL GAKIN-- 275   SEQ ID NO:5
ISO4-G1      D HEPWAGIGFGLERLLM KNGKSNA KTGKSI YL GYKL--- 273   SEQ ID NO:10
                : .** * ******** :  .  . :  . * :* :*     :
```

Fig. 3

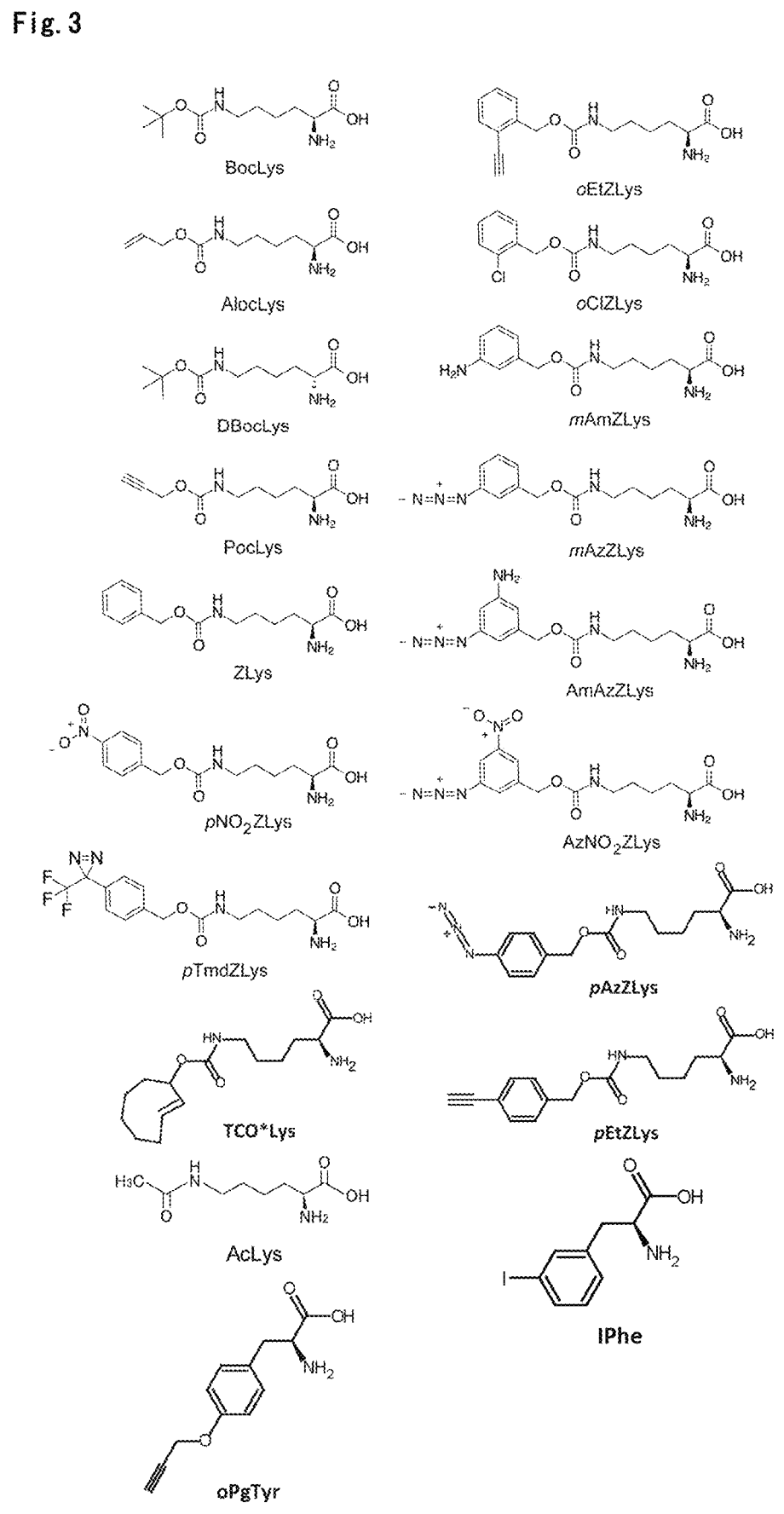

BocLys oEtZLys

AlocLys oClZLys

DBocLys mAmZLys

PocLys mAzZLys

ZLys

AmAzZLys pNO₂ZLys

AzNO₂ZLys pTmdZLys pAzZLys

TCO*Lys pEtZLys

AcLys

IPhe oPgTyr

Fig. 6

Fig. 7
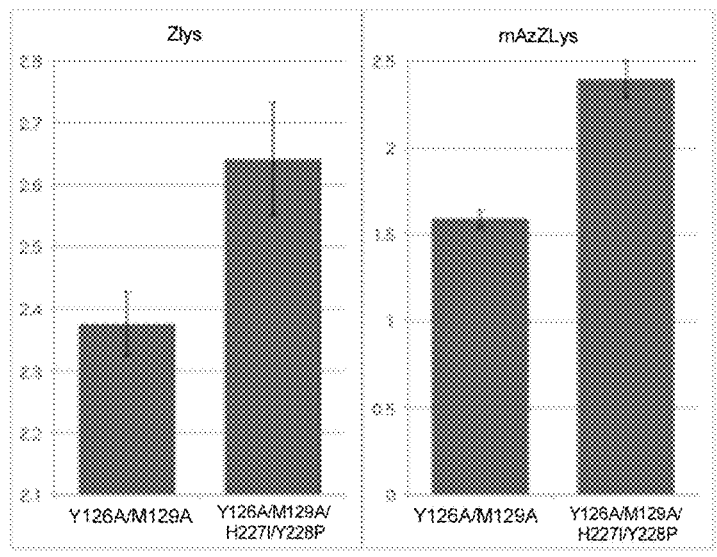
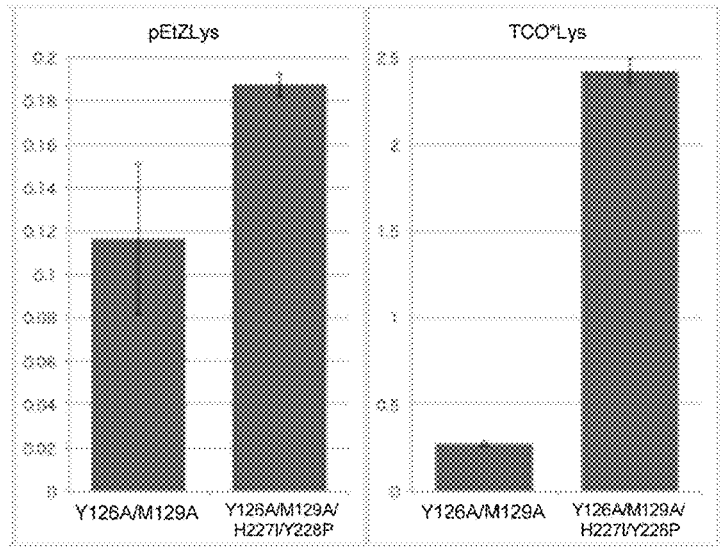
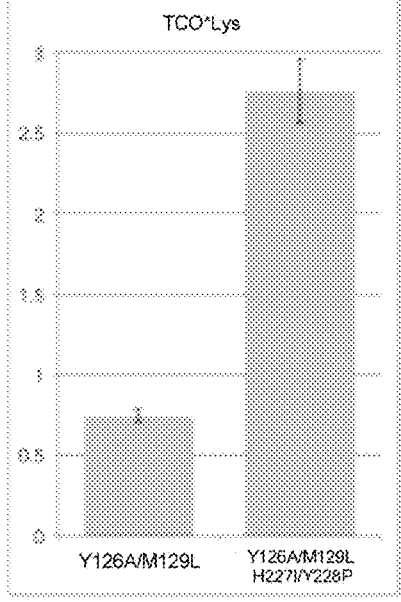

Yield of
TCO*-Lys-containing Herceptin Fab dimer

C: control, unreacted
10: reacted for 10 min
30 : reacted for 30 min

Electrophoresis:
1 μg equivalent

Fig. 16
a
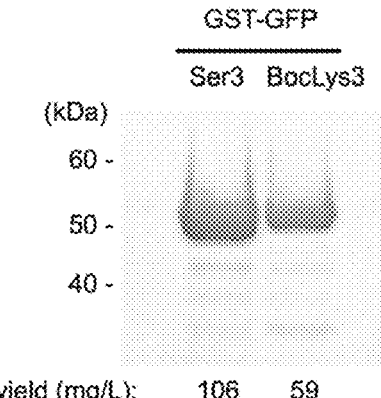
b
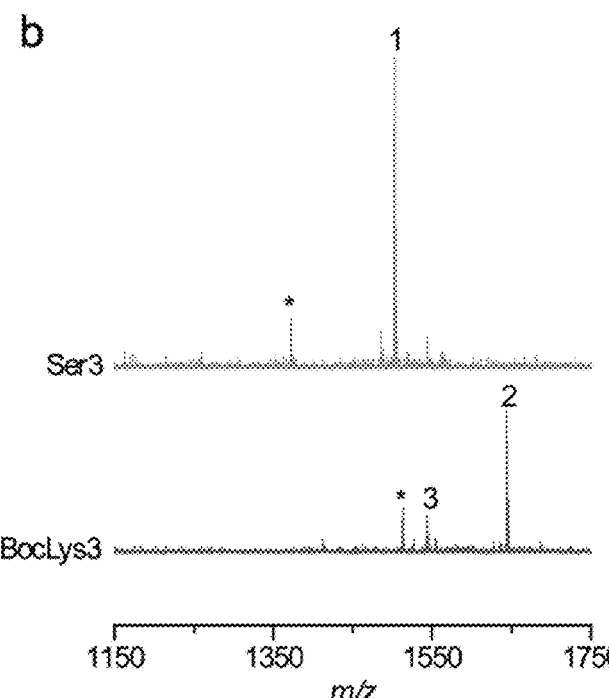
peptide 1-12 of GST-GFP
MNXSSHHHHHR
| peak No. | amino acid at X | Calculated [M+H]$^+$ | Observed [M+H]$^+$ |
|---|---|---|---|
| 1 | Ser | 1503.7 | 1503.7 |
| 2 | BocLys | 1644.8 | 1643.8 |
| 3 | Lys | 1544.7 | 1544.4 |

GFPS1 yield: pEtZLys

PYRROLYSYL-tRNA SYNTHETASE

SEQUENCE LISTING

The instant application contains a Sequence Listing which has been submitted electronically in ASCII format and is hereby incorporated by reference in its entirety. Said ASCII copy, created Feb. 26, 2024, is named 51007-022001_Sequence_Listing_2_26_24_ST25 and is 23,369 bytes in size.

TECHNICAL FIELD

The present invention relates to a method for producing a non-canonical amino acid-containing polypeptide by using a pyrrolysyl-tRNA synthetase, and others.

BACKGROUND ART

The aminoacyl-tRNA synthetase (aaRS) is an enzyme involved in protein synthesis. Specifically, the enzyme has been known to possess an activity of bonding an amino acid to tRNA through ester-bonding to synthesize an aminoacyl-tRNA. The aminoacyl-tRNA is a molecule involved, on the ribosome, in the elongation of the peptide chain constituting a protein.

A pyrrolysyl-tRNA synthetase (PylRS), which is a kind of aminoacyl-tRNA synthetase, has been used for research on incorporation of a non-canonical amino acid into a protein. For instance, Patent Literature 1 describes that PylRS (MmPylRS) from *Methanosarcina mazei* (*M. mazei*) was used to incorporate an α-hydroxy acid derivative of a lysine derivative into a protein. Patent Literature 2 describes that a MmPylRS mutant was used to incorporate a lysine derivative into a protein. Patent Literature 3 describes that a MmPylRS mutant was used to incorporate a ZLys derivative into an antibody. In addition, this literature also discloses that click chemistry was used to produce a chemically-modified compound of a ZLys derivative-corporated antibody.

Further, Non-Patent Literature 1 describes that the N-terminal domain of PylRS is essential for in vivo activity. Non-Patent Literature 2 describes that the N-terminal domain of PylRS binds to tRNA. Non-Patent Literature 3 describes that the N-terminal domain of PylRS interacts with tRNA.

Non-Patent Literature 4 describes that MmPylRS has an N-terminal domain while PylRS (MaPylRS) from Methanomethylophilus alvus (M. alvus) does not have the N-terminal domain. In addition, this literature also discloses that an *Escherichia coli* protein synthesis system with MaPylRS was used to incorporate a non-canonical amino acid into a protein.

CITATION LIST

Patent Literature

Patent Literature 1: WO/2009/066761
Patent Literature 2: WO/2009/038195
Patent Literature 3: WO/2017/030156

Non Patent Literature

Non Patent Literature 1: "The amino-terminal domain of pyrrolysyl-tRNA synthetase is dispensable in vitro but required for in vivo activity." Herring et al., FEBS Lett. 2007 Jul. 10, 581(17): 3197-203.

Non Patent Literature 2: "PylSn and the Homologous N-terminal Domain of Pyrrolysyl-tRNA Synthetase Bind the tRNA That Is Essential for the Genetic Encoding of Pyrrolysine" Jiang et al., J Biol Chem. 2012 Sep. 21, 287(39): 32738-32746.

Non Patent Literature 3: "Crystal structures reveal an elusive functional domain of pyrrolysyl-tRNA synthetase." Suzuki et al., Nat Chem Biol. 2017 December, 13(12): 1261-1266.

Non-Patent Literature 4: "Mutually orthogonal pyrrolysyl-tRNA synthetase/tRNA pairs." Willis et al., Nat Chem. 2018 May 28, doi: 10.1038/s41557-018-0052-5 [Epub ahead of print].

SUMMARY OF INVENTION

Technical Problem

The above Non-Patent Literature 4 describes that a non-canonical amino acid was successfully incorporated even in the case of using MaPylRS, which lacks the N-terminal domain. However, the *Escherichia coli* protein synthesis system in Non-Patent Literature 4 cannot be said to have sufficiently high efficiencies of incorporating non-canonical amino acids.

The above Non-Patent Literature 4 describes experiments for whether or not a non-canonical amino acid is incorporated into protein and whether the system is orthogonal, an experiment for the selectivity of non-canonical amino acid, and an experiment for the incorporation of different non-canonical amino acids into one polypeptide. Meanwhile, the literature fails to describe any method in which the incorporation efficiency is markedly increased when compared to the case of using MmPylRS. Note that the glmS promoter (a non-high expression promoter) is used as the promoter for expressing MmPylRS.

Here, the present inventors have attempted to use a cell-free protein synthesis system with MmPylRS to incorporate a non-canonical amino acid into a protein. Unfortunately, after MmPylRS was isolated and then used for the cell-free protein synthesis system, it was found that the concentration limit is 4 mg/mL or lower and the MmPylRS was thus unable to be used at a concentration higher than the limit (Experimental Example 1 and Examples 2 and 3). As a result, it was impossible to increase the non-canonical amino acid incorporation efficiency.

In addition, the present inventors have also attempted to use an *Escherichia coli* protein synthesis system with MmPylRS to incorporate a non-canonical amino acid into a protein. An attempt to express MmPylRS using a promoter for high expression resulted in reduced efficiency of incorporation efficiency . . . . In addition, suppression of *Escherichia coli* growth was observed. This indicates that high expression level of MmPylRS in the *Escherichia coli* protein synthesis system is not suitable.

The present invention has been made in light of the above observations. The purpose of the invention is to provide a method for efficiently producing a polypeptide containing a non-canonical amino acid; a method for incorporating a non-canonical amino acid into a polypeptide; a method for producing tRNA bound to a non-canonical amino acid; a non-canonical amino acid incorporation system; a material for use in these methods; or the like.

Solution to Problem

The present inventors are the first to isolate and purify MaPylRS as described in Examples later. Further, it has been found that a MaPylRS solution can be concentrated to prepare a highly concentrated MaPylRS solution, because the concentration limit of MaPylRS is remarkably high (Examples 1 and 3). This concentration limit of MaPylRS is five or more times the concentration limit of MmPylRS and is thus unexpected.

Further, a non-canonical amino acid was attempted to be incorporated into a protein by using a cell-free protein synthesis system with a highly concentrated MaPylRS solution (Examples 3 and 6). As a result, the non-canonical amino acid incorporation efficiency was unexpectedly and markedly higher than when MmPylRS was used.

In addition, it was attempted to use click chemistry for reacting a fluorescent substrate with a TCO*-Lys incorporated in a Fab antibody (Example 8). The results are surprising and the linking reaction was almost completed within just 10 min. Because the protein is unstable, it is a break-through result that the reaction was completed within a short period of time.

In addition, a non-canonical amino acid was attempted to be incorporated into a protein through an *Escherichia coli* protein synthesis system with a vector carrying a MaPylRS gene under regulation by a strong promoter (Examples 9 to 12). As a result, the non-canonical amino acid incorporation efficiency was unexpectedly and markedly higher than when MmPylRS was used.

Specifically, an aspect of the invention provides a method for producing a polypeptide containing a non-canonical amino acid, comprising: a step of contacting PylRS from an organism belonging to the order Methanomassiliicoccales or Thermoplasmatales with the non-canonical amino acid; and an incorporation step selected from step (a) of incorporating the non-canonical amino acid into the polypeptide with higher efficiency than in a case of using a cell-free protein synthesis system with MmPylRS or step (b) of incorporating the non-canonical amino acid into the polypeptide with higher efficiency than in a case of using an *Escherichia coli* protein synthesis system with a vector carrying a gene for the PylRS under regulation by a glmS promoter or a case of using an *Escherichia coli* protein synthesis system with a vector carrying a gene for the PylRS under regulation by a glnS promoter. This production method may be used to efficiently produce a polypeptide containing a non-canonical amino acid. Note that the glmS promoter and the glnS promoter (Plumbridge and Soll, Biochimie, 1987 May, 69(5): 539-41) are each a promoter that fails to fall under a high-expression promoter (non-high expression promoter).

Another aspect of the invention provides a method for incorporating a non-canonical amino acid into a polypeptide, comprising: a step of contacting PylRS from an organism belonging to the order Methanomassiliicoccales or Thermoplasmatales with the non-canonical amino acid; and an incorporation step selected from step (a) of incorporating the non-canonical amino acid into the polypeptide with higher efficiency than in a case of using a cell-free protein synthesis system with MmPylRS or step (b) of incorporating the non-canonical amino acid into the polypeptide with higher efficiency than in a case of using an *Escherichia coli* protein synthesis system with a vector carrying a gene for the PylRS under regulation by a glmS promoter or a case of using an *Escherichia coli* protein synthesis system with a vector carrying a gene for the PylRS under regulation by a glnS promoter. This incorporation method may be used to efficiently incorporate a non-canonical amino acid into a polypeptide.

Still another aspect of the invention provides a non-canonical amino acid incorporation system comprising highly concentrated PylRS from an organism belonging to the order Methanomassiliicoccales or Thermoplasmatales. This non-canonical amino acid incorporation system may be used to efficiently produce a polypeptide containing a non-canonical amino acid.

Still another aspect of the invention provides a reaction solution for a cell-free protein synthesis system, comprising PylRS from an organism belonging to the order Methanomassiliicoccales or Thermoplasmatales. This reaction solution may be used to efficiently produce a polypeptide containing a non-canonical amino acid.

Still another aspect of the invention provides a method for producing a polypeptide containing a non-canonical amino acid, comprising the step of contacting PylRS from an organism belonging to the order Methanomassiliicoccales or Thermoplasmatales with the non-canonical amino acid extracellularly. This production method may be used to efficiently produce a polypeptide containing a non-canonical amino acid.

Still another aspect of the invention provides a method for incorporating a non-canonical amino acid into a polypeptide, comprising the step of contacting PylRS from an organism belonging to the order Methanomassiliicoccales or Thermoplasmatales with the non-canonical amino acid extracellularly. This incorporation method may be used to efficiently incorporate a non-canonical amino acid into a polypeptide.

Still another aspect of the invention provides a method for producing tRNA bonded to a non-canonical amino acid, comprising the step of contacting PylRS from an organism belonging to the order Methanomassiliicoccales or Thermoplasmatales with the non-canonical amino acid and the tRNA extracellularly. This production method may be used to efficiently produce tRNA bonded to a non-canonical amino acid.

Still another aspect of the invention provides purified PylRS from an organism belonging to the order Methanomassiliicoccales or Thermoplasmatales. This PylRS may be used to efficiently produce a polypeptide containing a non-canonical amino acid.

Still another aspect of the invention provides a solution including 5 mg/mL or higher PylRS from an organism belonging to the order Methanomassiliicoccales or Thermoplasmatales. This solution may be used to efficiently produce a polypeptide containing a non-canonical amino acid.

Still another aspect of the invention provides a polynucleotide that encodes PylRS from an organism belonging to the order Methanomassiliicoccales or Thermoplasmatales and a high-expression promoter. This polynucleotide may be used to efficiently produce a polypeptide containing a non-canonical amino acid.

Still another aspect of the invention provides a method for producing a polypeptide containing a non-canonical amino acid, comprising the step of expressing, at a high level in a living cell, PylRS from an organism belonging to the order Methanomassiliicoccales or Thermoplasmatales. This production method may be used to efficiently produce a polypeptide containing a non-canonical amino acid.

BRIEF DESCRIPTION OF DRAWINGS

FIG. 2 is a diagram showing each amino acid sequence of Methanomethylophilus alvus (M. alvus), *Methanosarcina*

*barkeri* (*M. barkeri*), or *Methanosarcina mazei* (*M. mazei*) PylRS, which is aligned using Clustal Omega.

FIG. 3 is a diagram showing examples of lysine derivative that can be incorporated into a protein.

Figure 4:
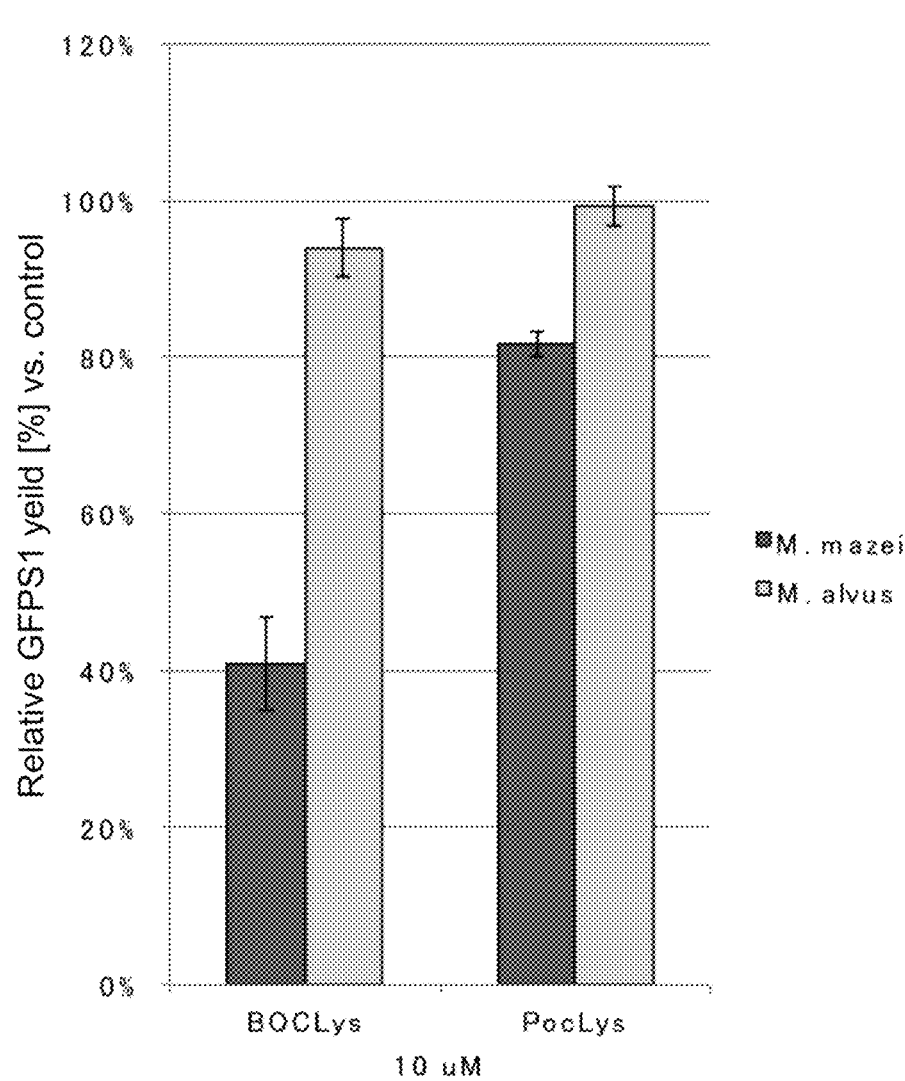

FIG. 4 is a graph showing the experimental results of comparing the yield of protein having non-canonical amino acids incorporated while MaPylRS or MmPylRS was used in a cell-free protein synthesis process.

Figure 5:
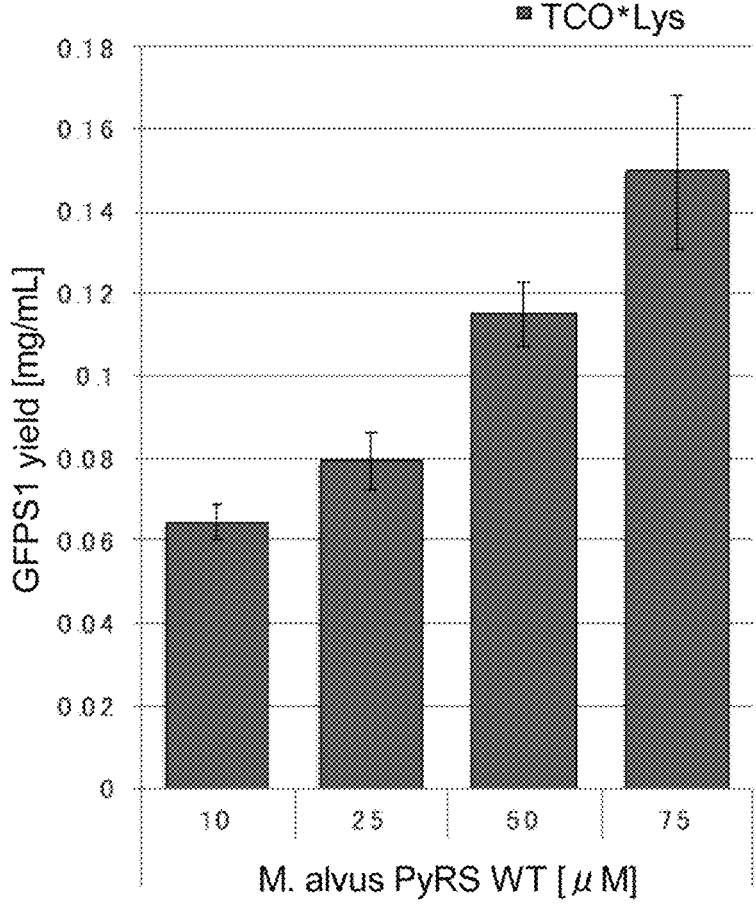

FIG. 5 is a graph showing the results of examining MaPylRS concentration dependence in a cell-free protein synthesis process.

Figure 6:
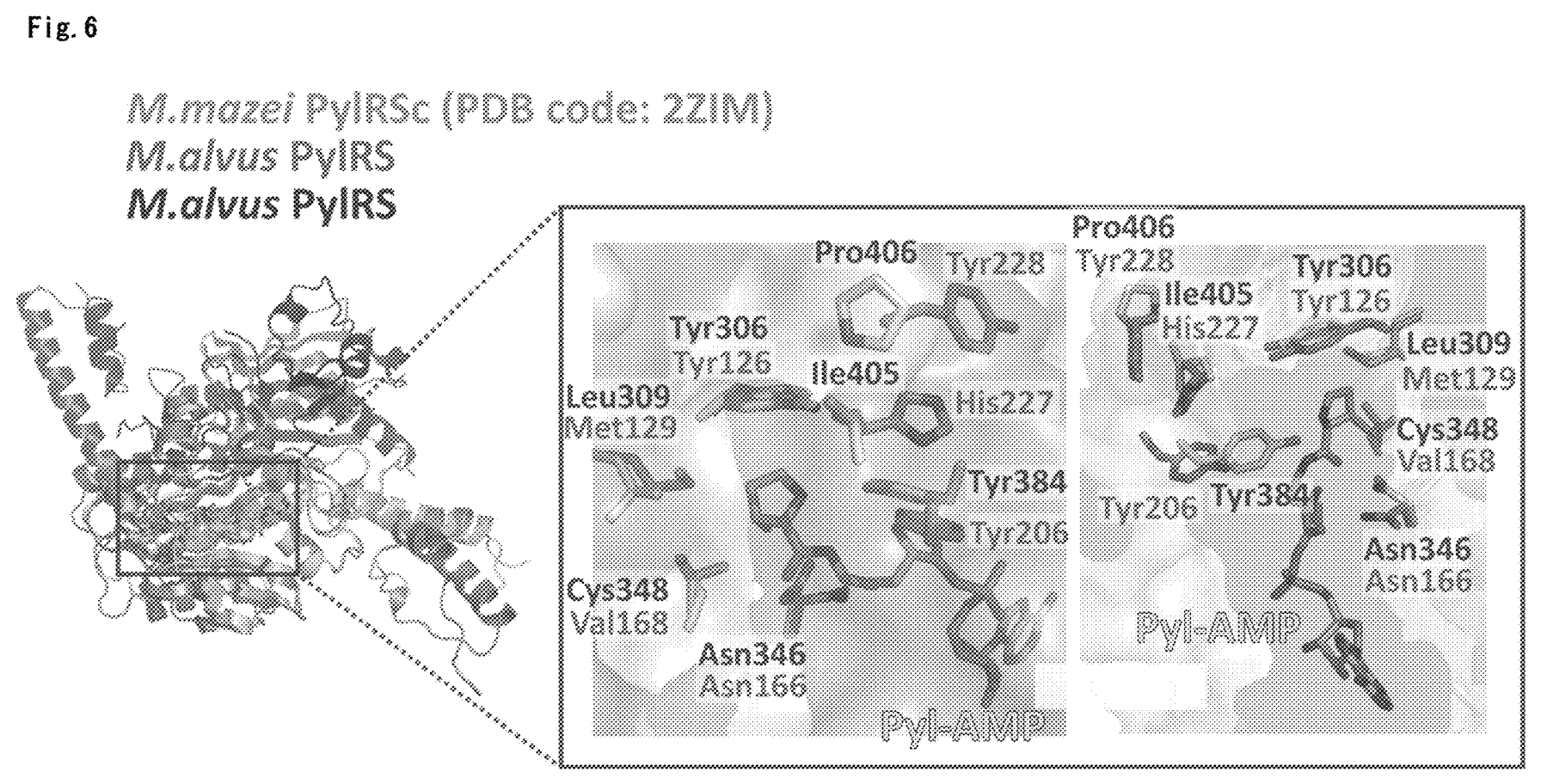

FIG. 6 is a diagram showing the results of crystallography.

FIG. 7 is graphs showing the results of checking activity of each MaPylRS mutant.

Figure 8:
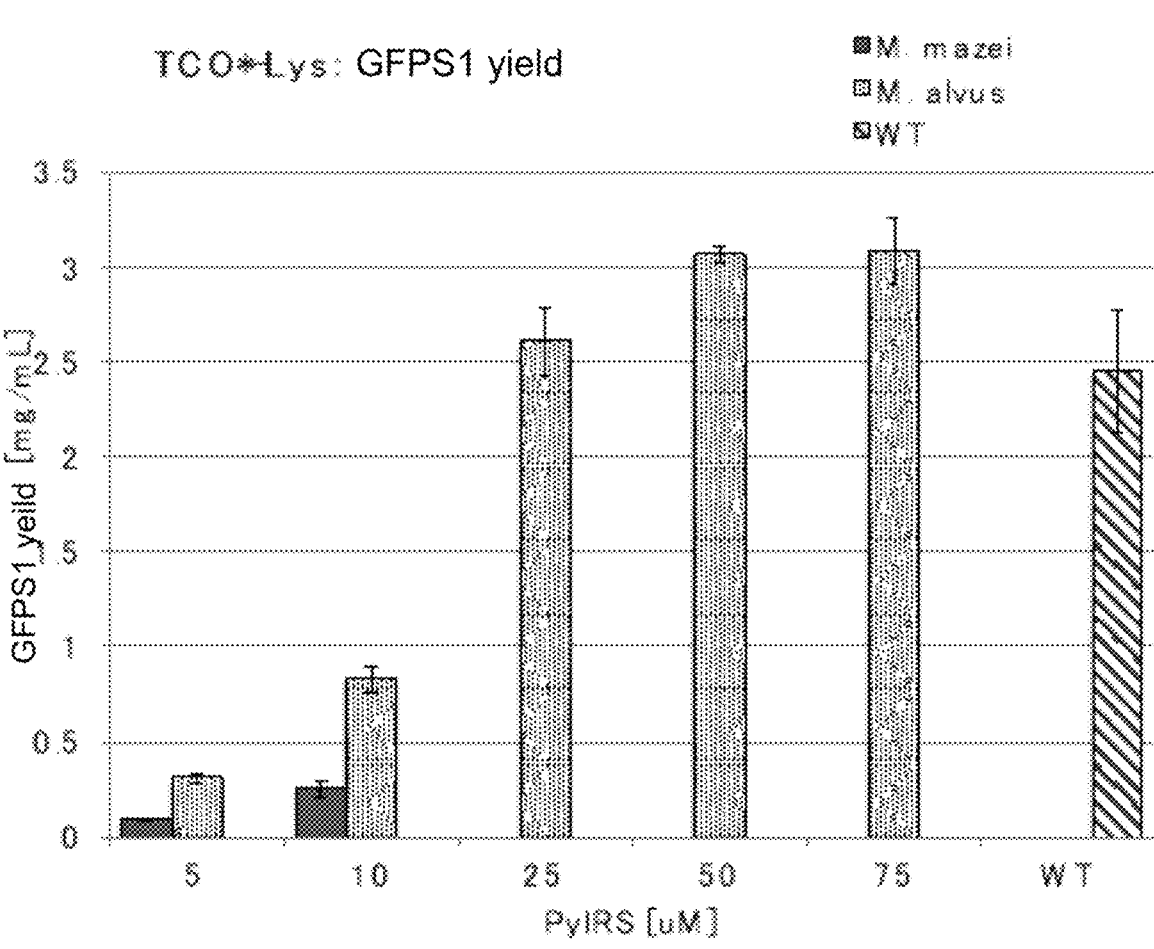

FIG. 8 is a graph showing the results of examining PylRS concentration dependence when TCO*-Lys was incorporated.

Figure 9:
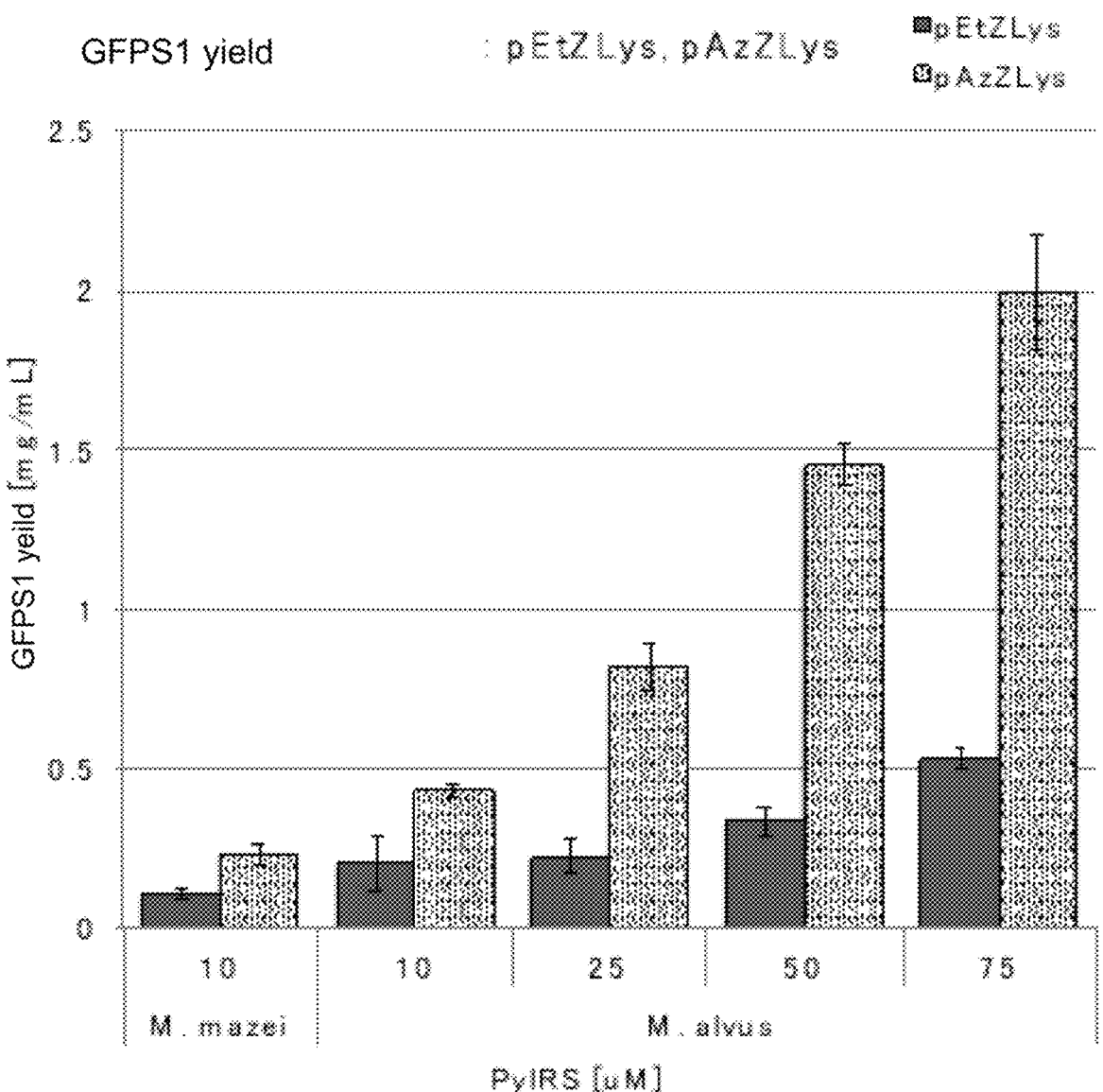

FIG. 9 is a graph showing the results of examining PylRS concentration dependence when pEtZLys or pAzZLys was incorporated.

Figure 10:
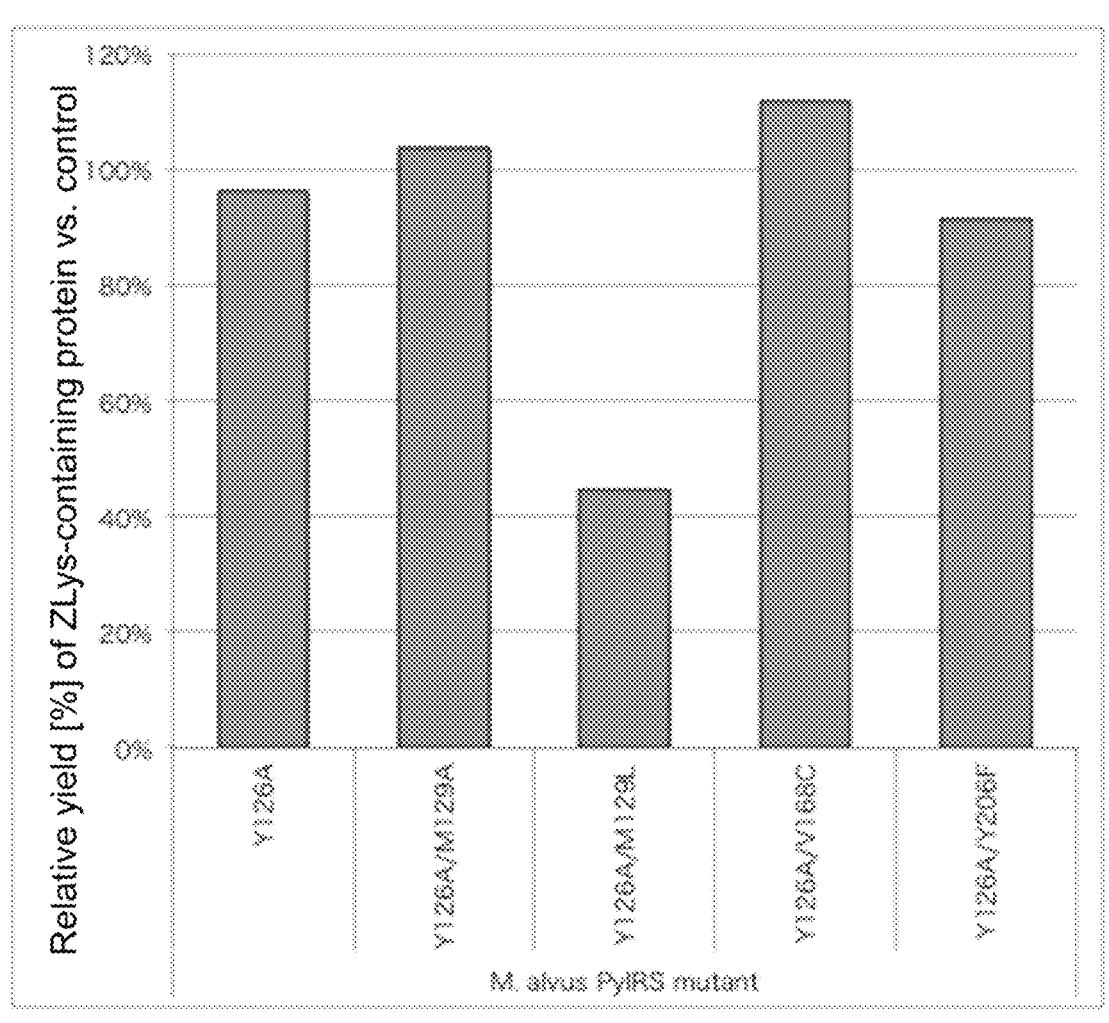

FIG. 10 is a graph showing the results of checking the yield of ZLys-corporated protein.

Figure 11:
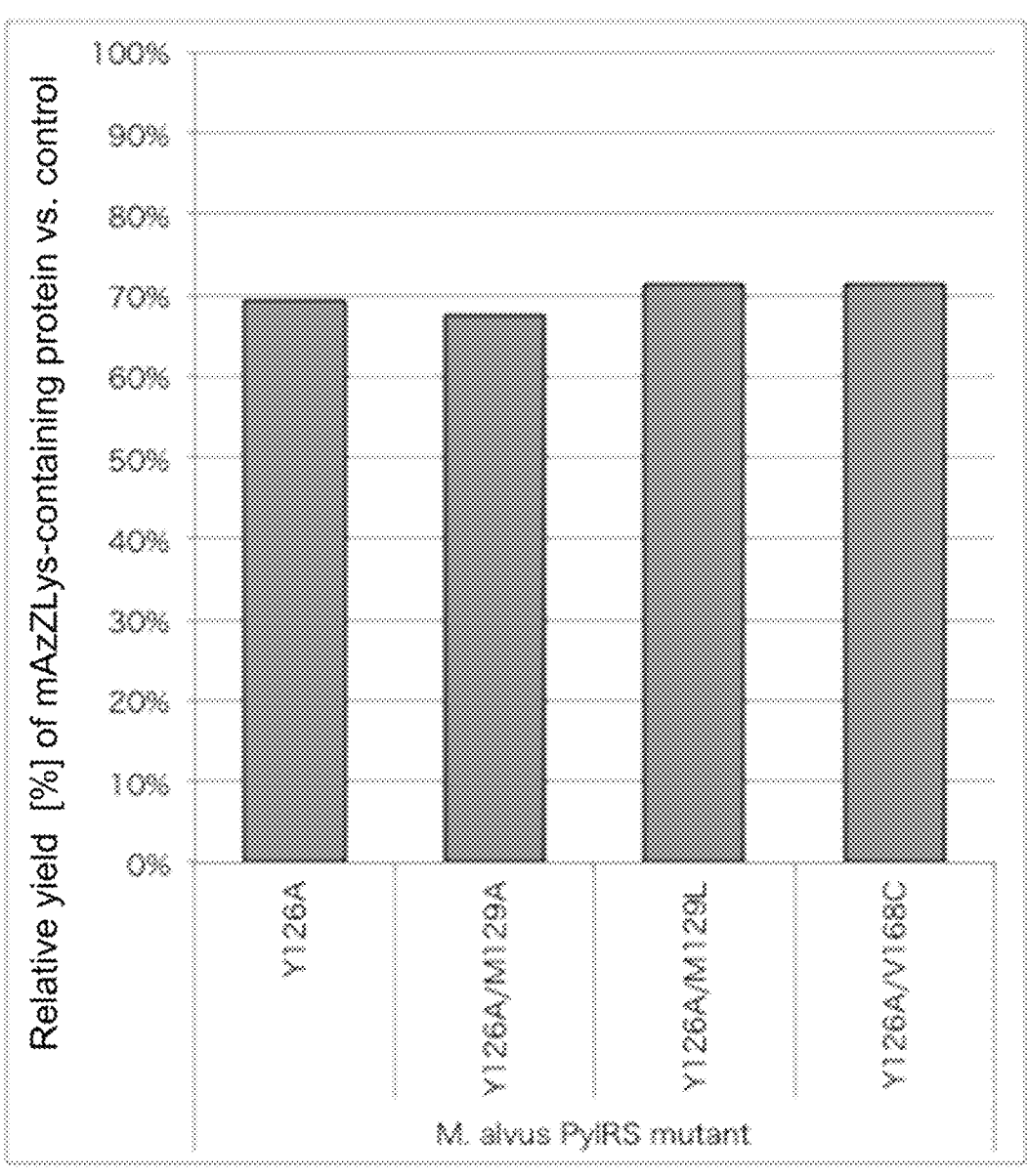

FIG. 11 is a graph showing the results of checking the yield of mAzZLys-corporated protein.

Figure 12:
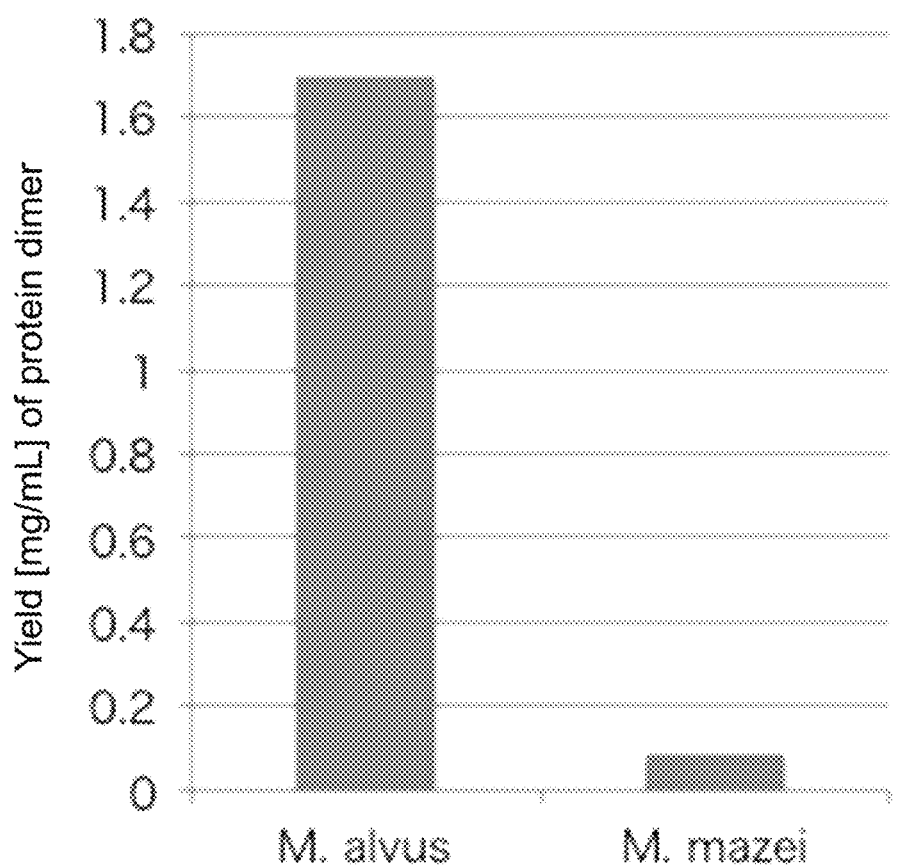

FIG. 12 is a graph indicating the yield of Fab antibody having TCO*-Lys incorporated.

Figure 13:
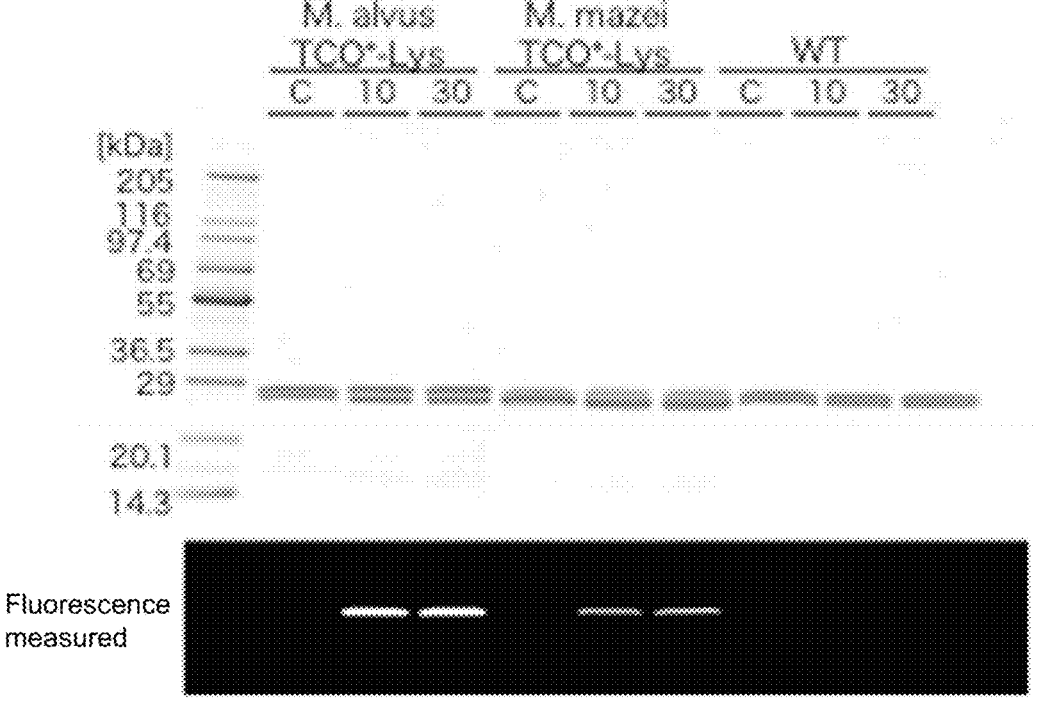

FIG. 13 is an image illustrating the results of using click chemistry for linking a fluorescent substrate with a TCO*-Lys incorporated in a Fab antibody.

Figure 14:
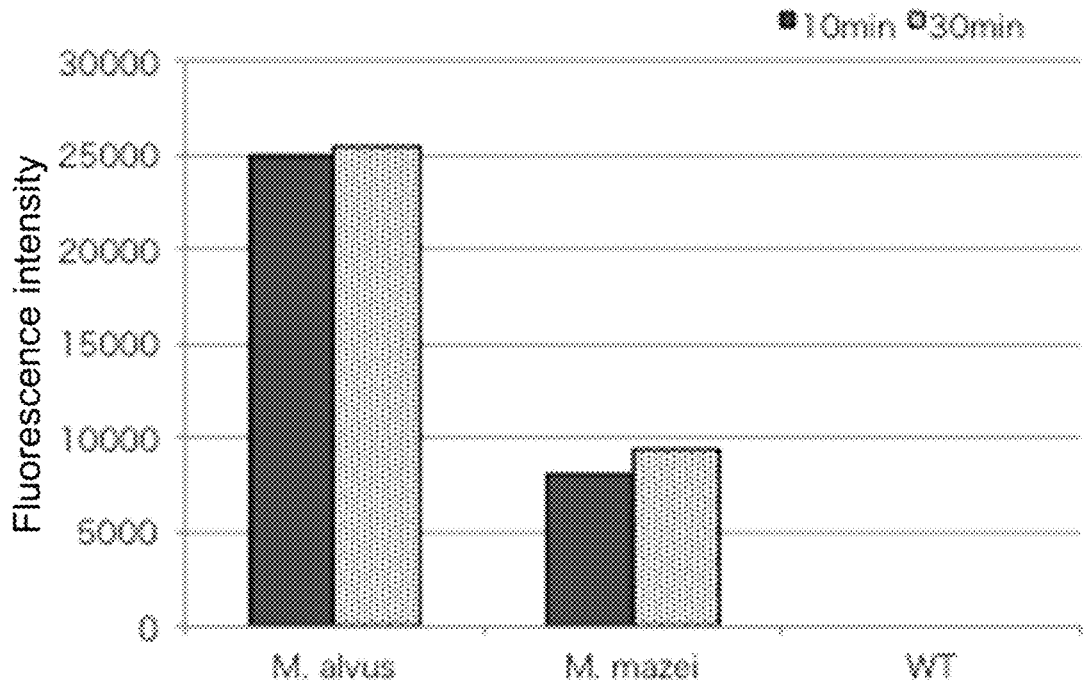

FIG. 14 is a graph indicating the fluorescent intensity of fluorescent substrate linked to the TCO*-Lys.

Figure 15:
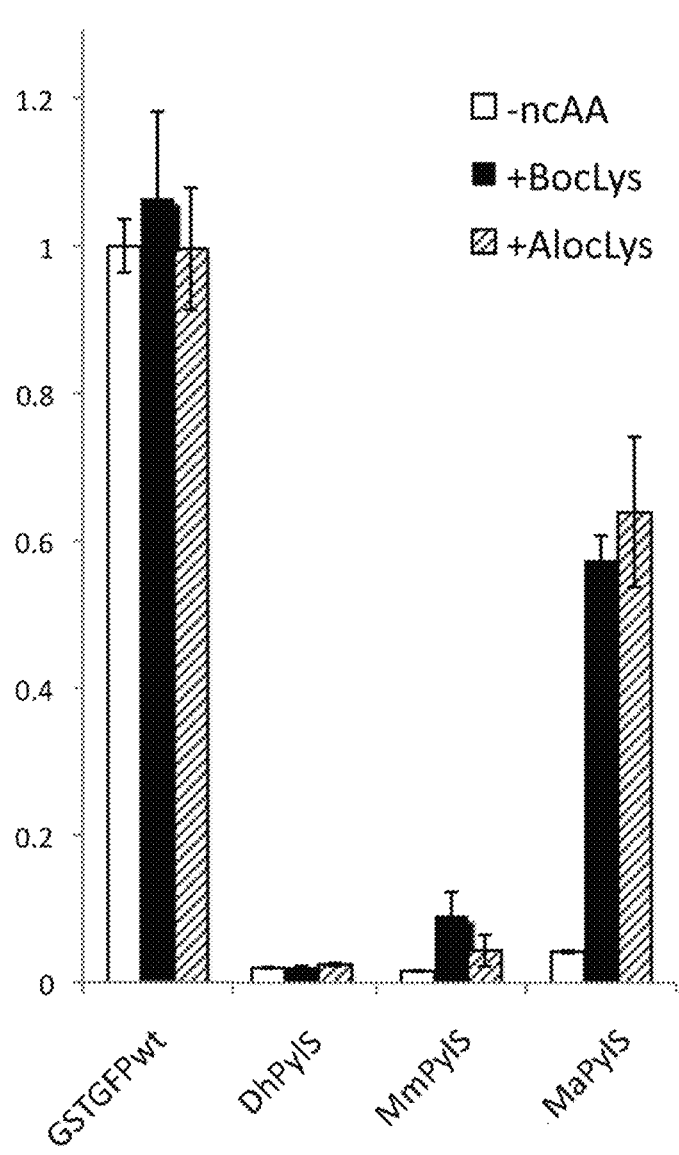

FIG. 15 is a graph showing the experimental results of comparing non-canonical amino acid incorporation efficiency while *Methanosarcina mazei* (*M. mazei*), Methanomethylophilus alvus (M. alvus), or *Desulfitobacterium hafniense* (*D. hafniense*) PylRS was used in an *Escherichia coli* expression system.

FIG. 16 is an image, a spectrogram, and a table showing the results of analyzing a wild-type GST-GFP fusion protein (3Ser) and an amber mutant of the GST-GFP fusion protein. a: CBB staining after SDS-PAGE; b: MALDI-TOF MS analysis after each product was digested with trypsin. The observed values and calculated values are provided in the table.

Figure 17:
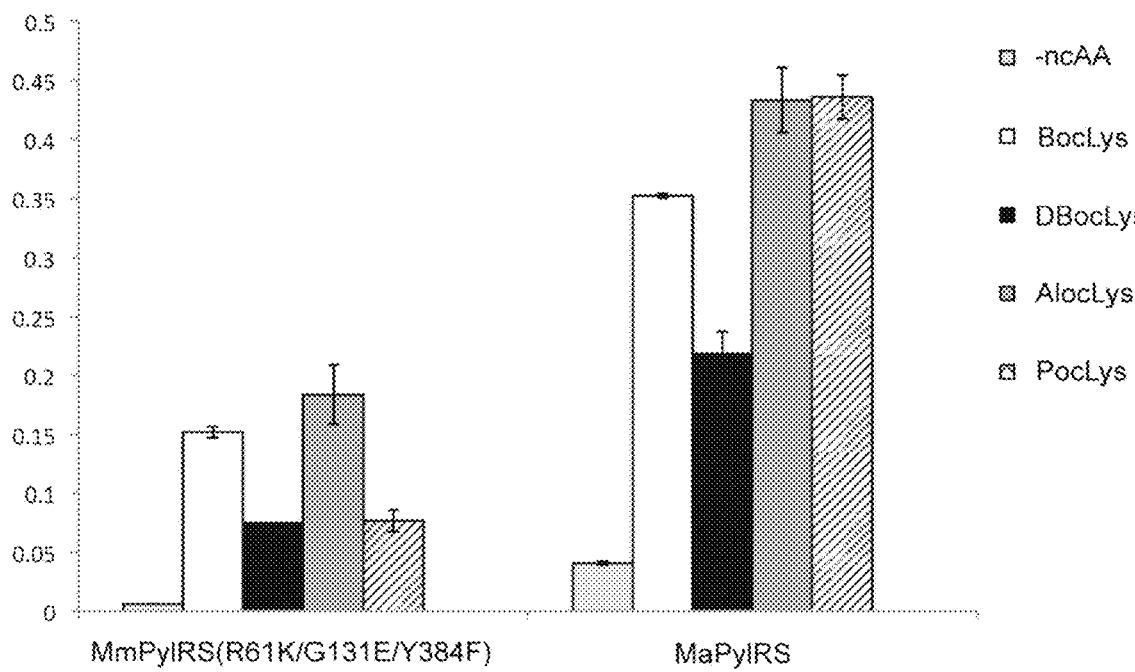

FIG. 17 is a graph showing the experimental results of site-specific incorporation of non-canonical amino acids into proteins by using MaPylRS in an *Escherichia coli* expression system.

Figure 18:
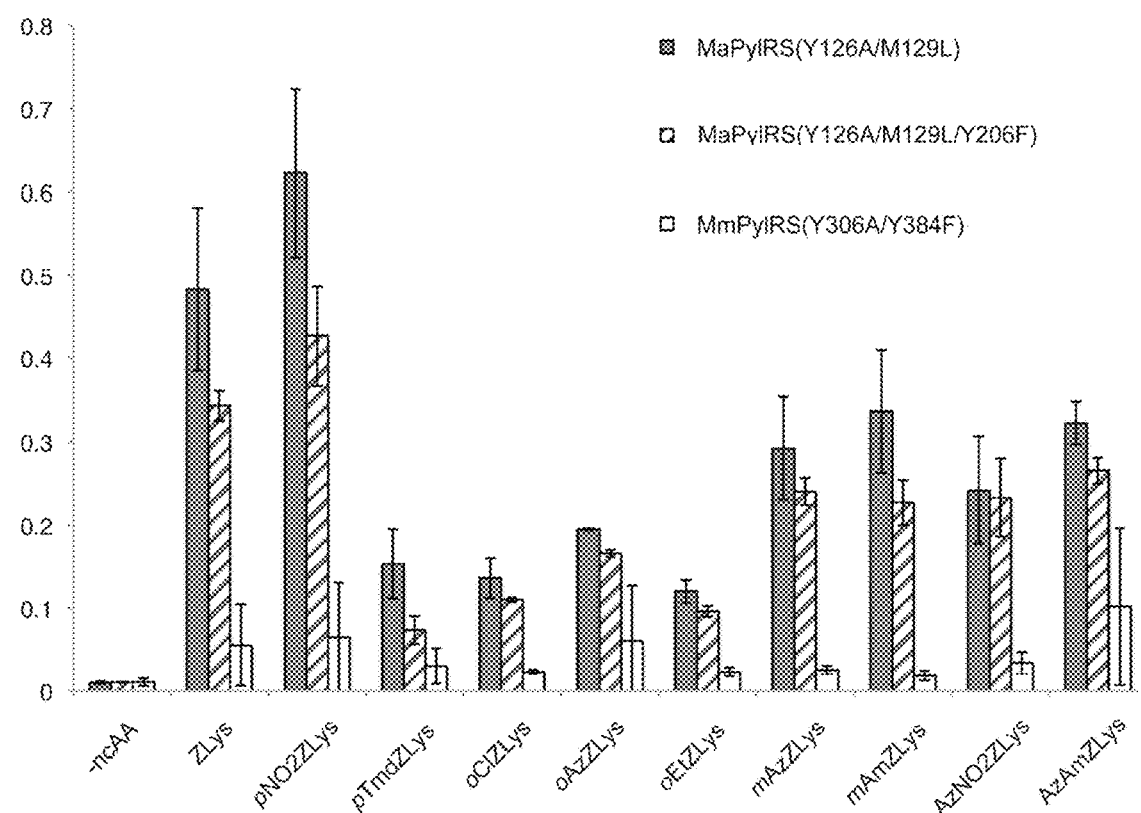

FIG. 18 is a graph showing the experimental results of site-specific incorporation of each ZLys-based non-canonical amino acid into a protein by using each MaPylRS mutant in an *Escherichia. coli* expression system.

Figure 19:
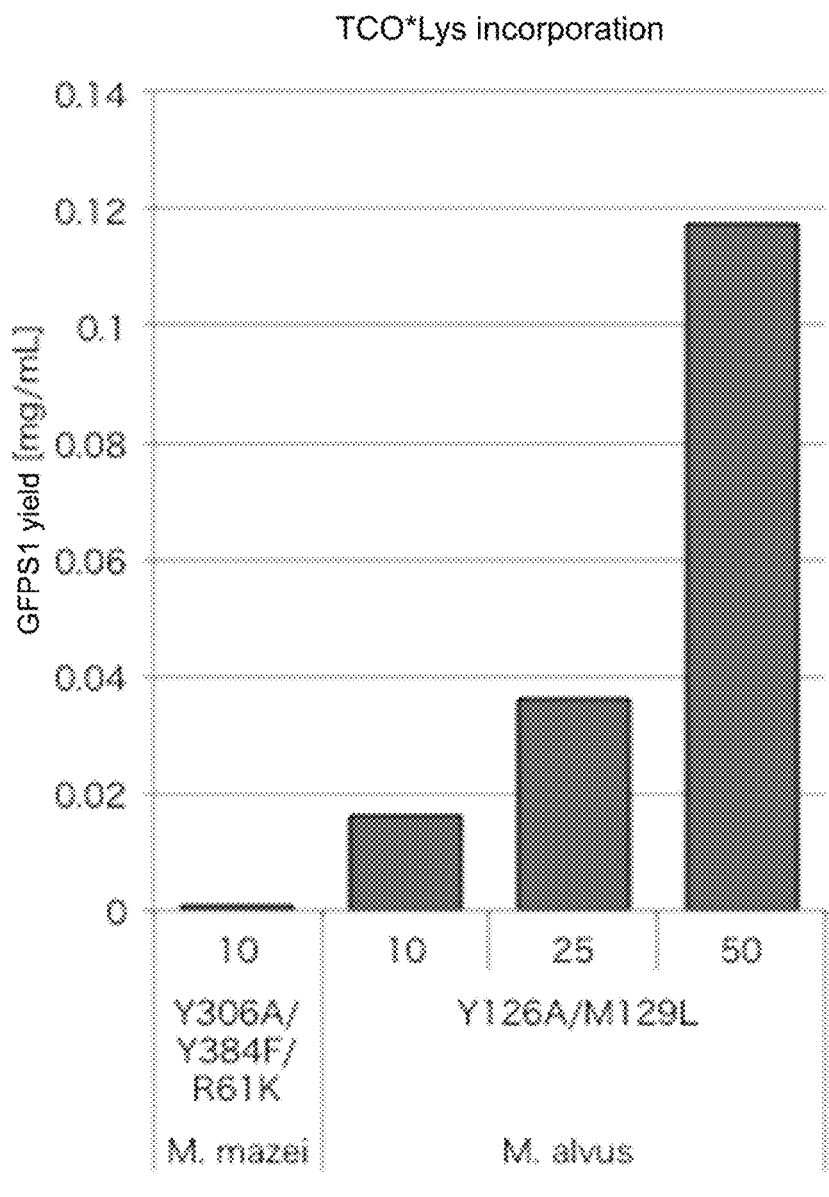

FIG. 19 is a graph showing the results of examining PylRS concentration dependence in a wheat germ-based, cell-free protein synthesis process.

Figure 20:
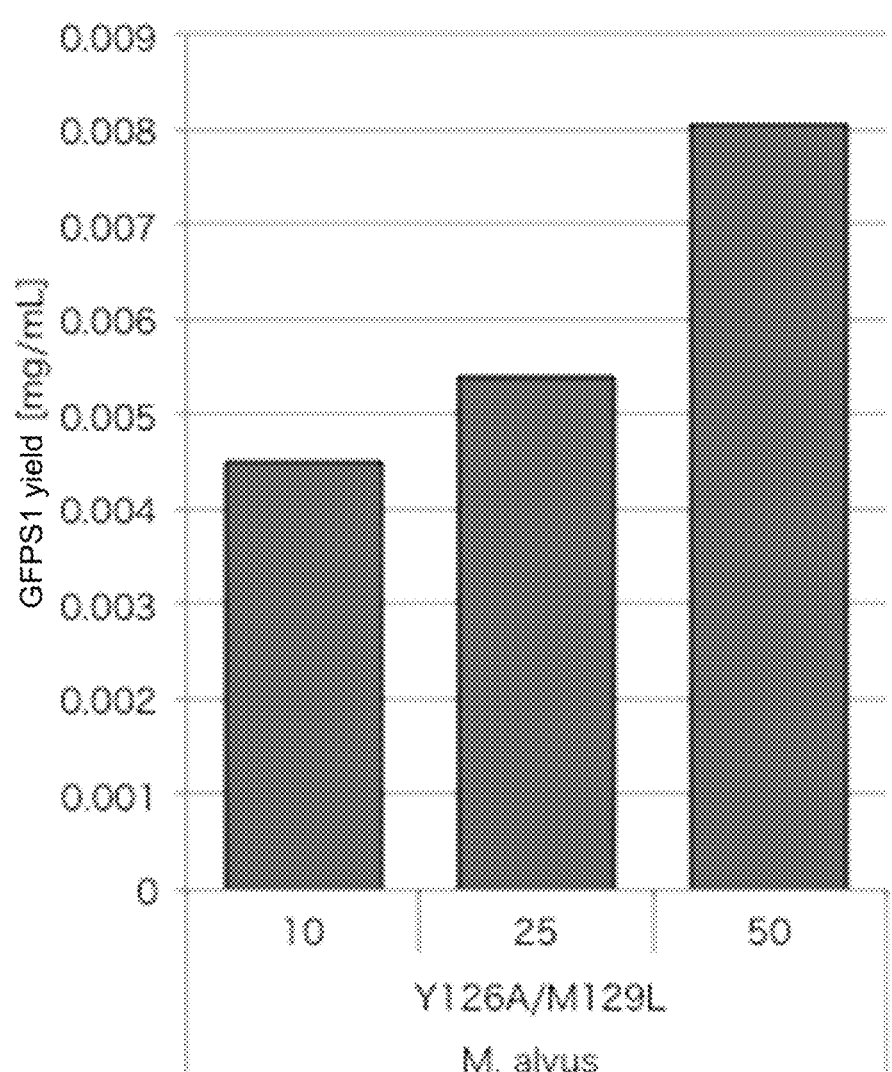

FIG. 20 is a graph indicating PylRS concentration dependence in a human-based, cell-free protein synthesis process.

Figure 21:
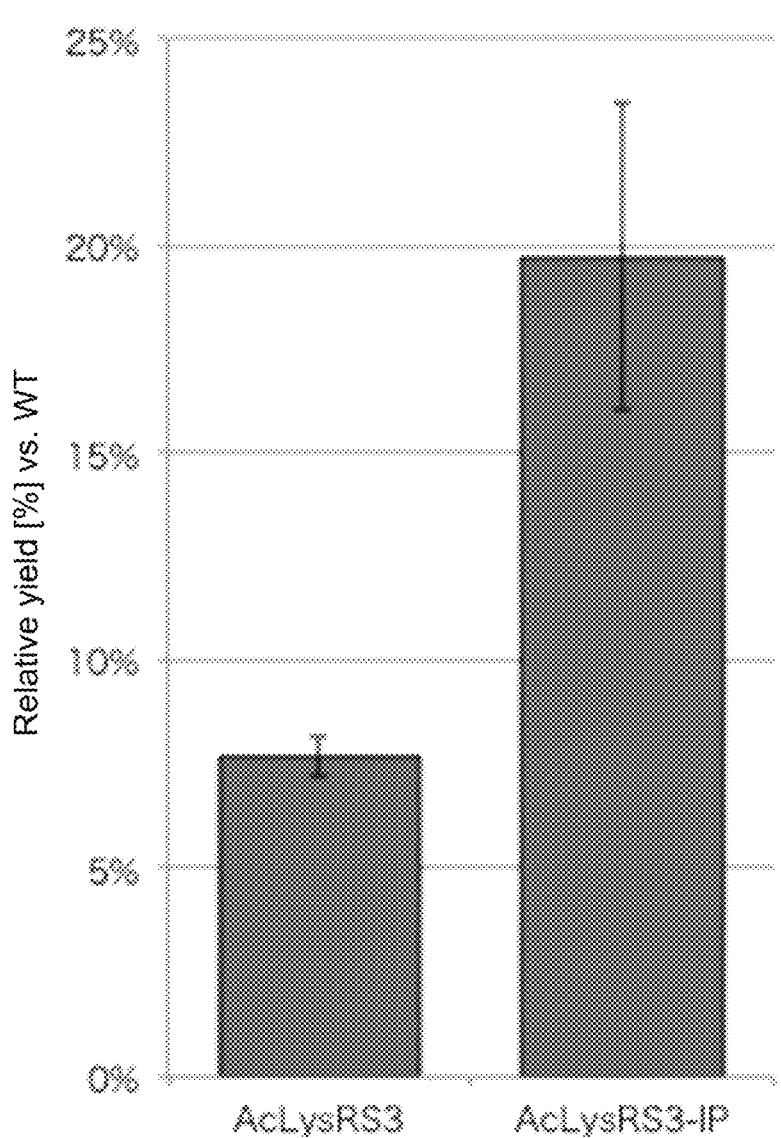

FIG. 21 is a graph showing the results of checking AcLys incorporation.

Figure 22:
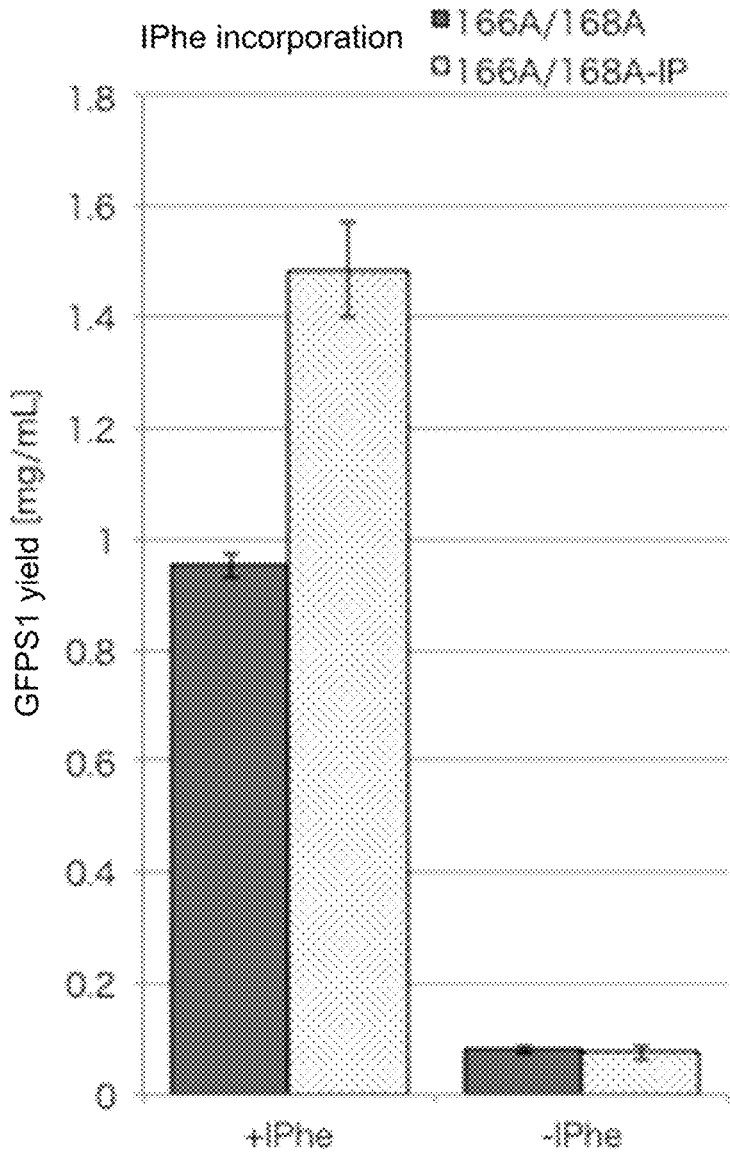

FIG. 22 is a graph showing the results of checking Phe derivative incorporation.

Figure 23:
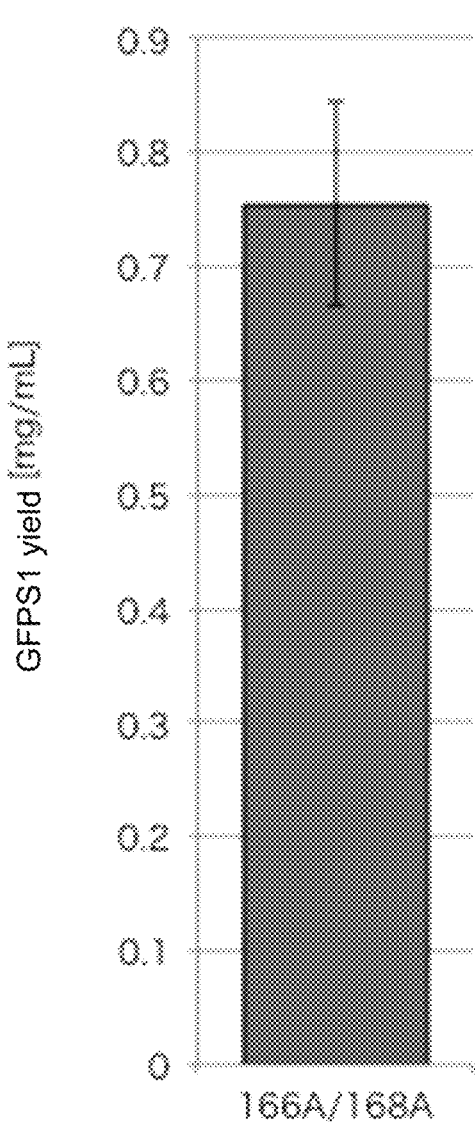

FIG. 23 is a graph showing the results of checking Tyr derivative incorporation.

Figure 24:
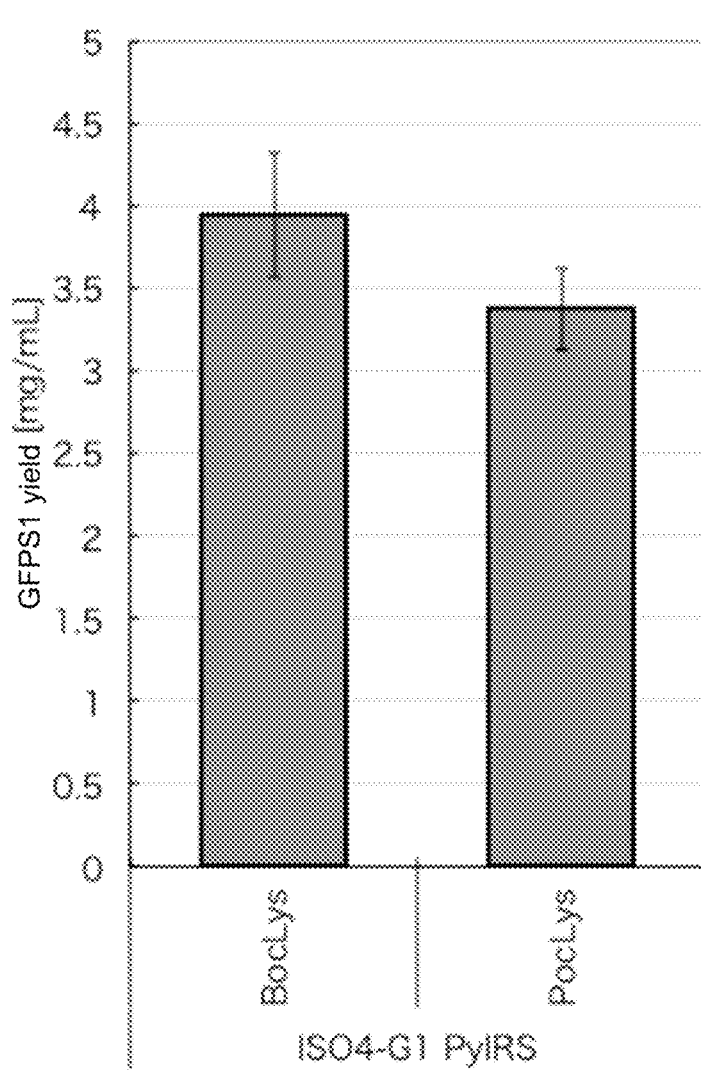

FIG. 24 is a graph showing the results of checking activity of G1PylRS in a cell-free protein synthesis process.

Figure 25:
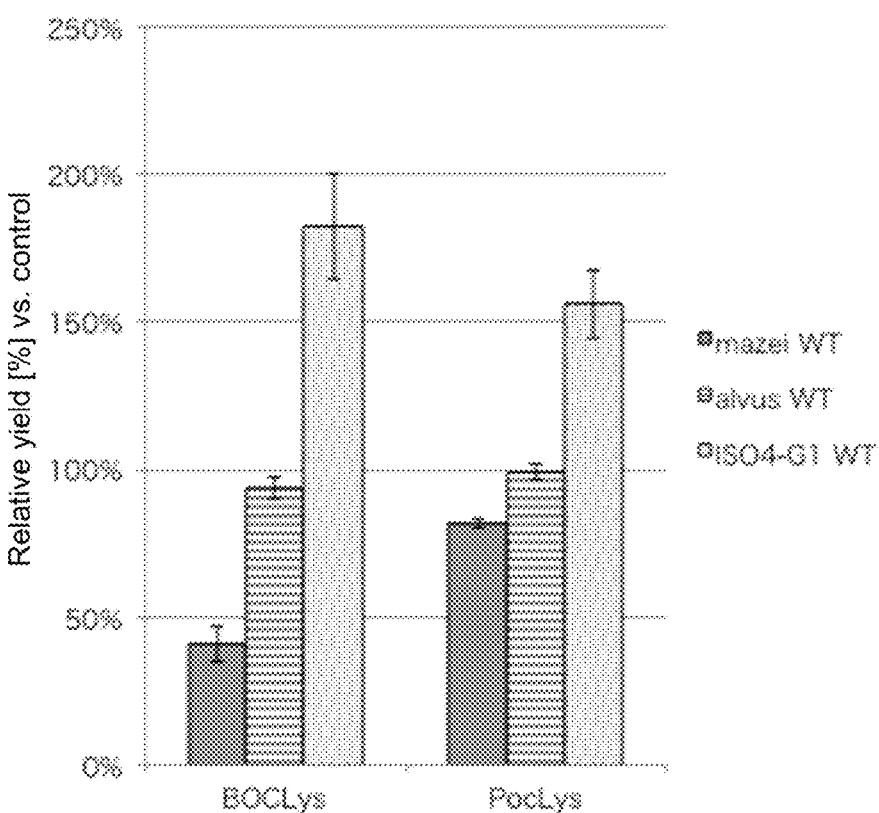

FIG. 25 is a graph showing the results of comparing the protein yield when G1PylRS, MaPylRS, or MaPylRS was used.

Figure 26:
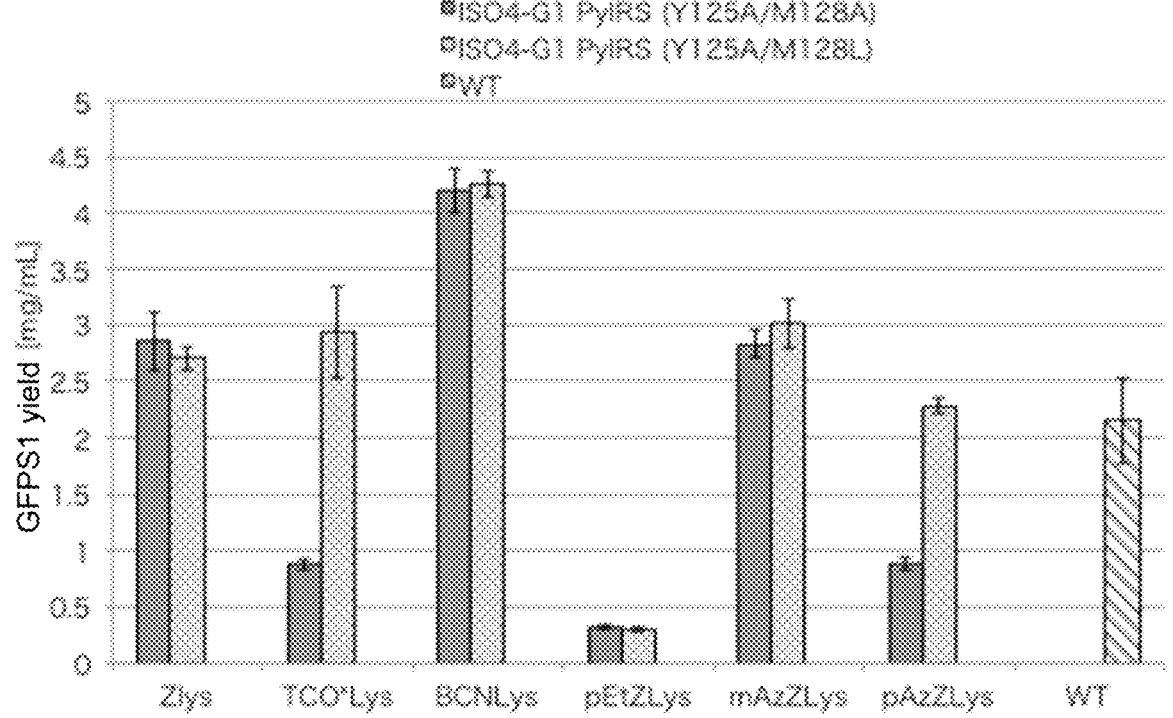

FIG. 26 is a graph showing the results of checking activity of each G1PylRS mutant in a cell-free protein synthesis process.

Figure 27:
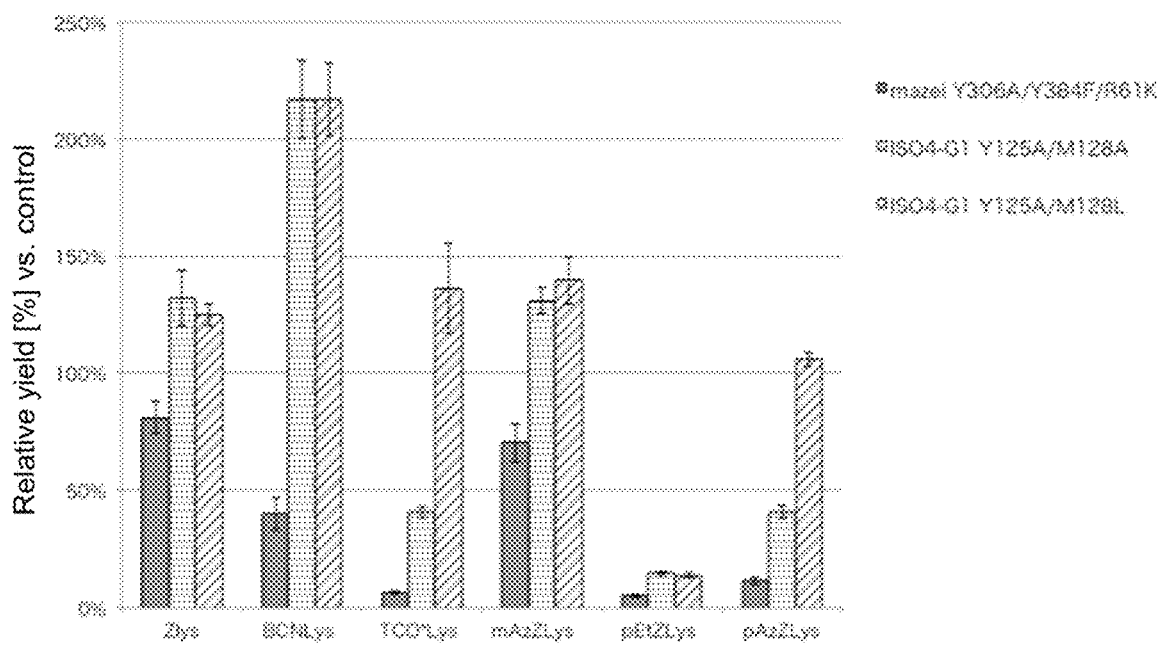

FIG. 27 is a graph showing the results of comparing the protein yield when each of G1PylRS or MaPylRS mutants was used.

Figure 28:
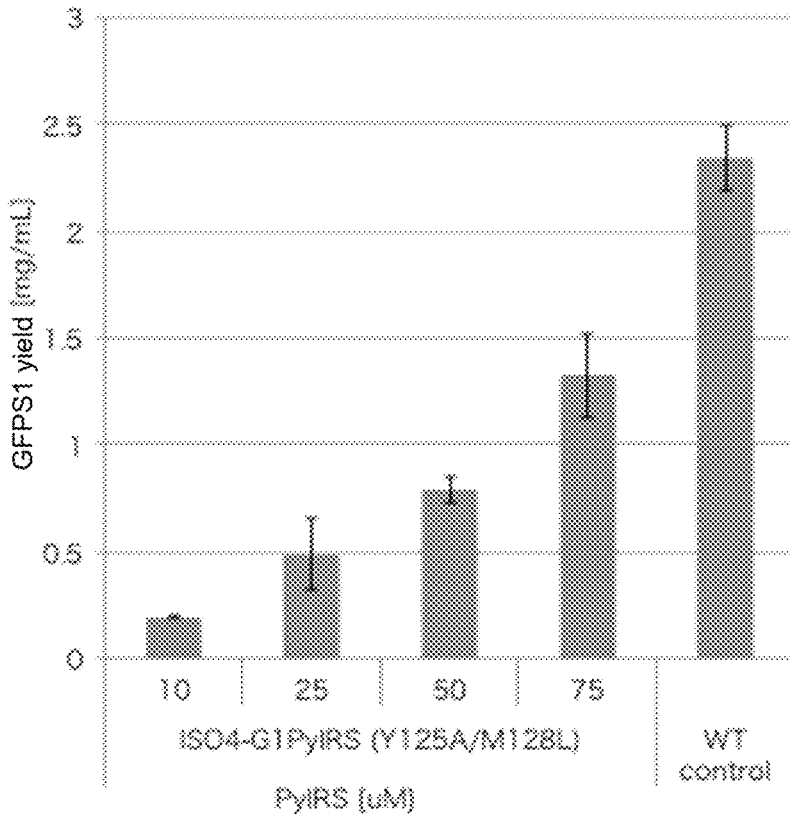

FIG. 28 is a graph indicating G1PylRS concentration dependence in a cell-free protein synthesis process.

Figure 29:
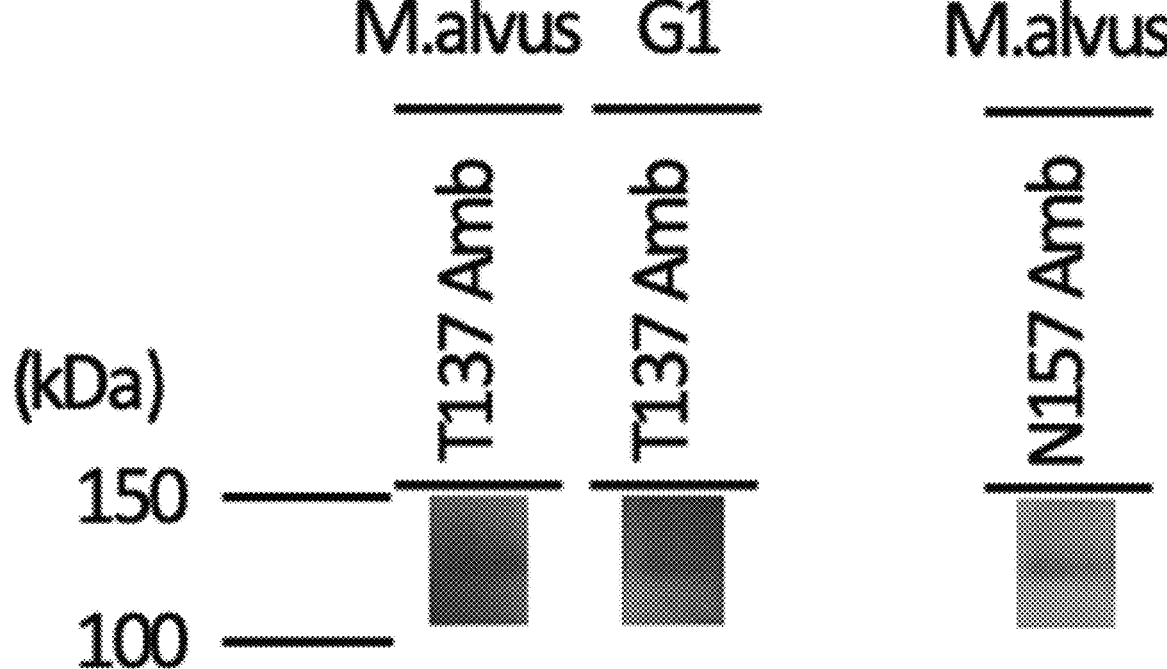

FIG. 29 is images showing the results of incorporating mAzZLys into a protein in a mammalian cell.

DESCRIPTION OF EMBODIMENTS

Hereinafter, embodiments of the invention will be described in detail. Note that repeated descriptions of the same content are omitted, if appropriate, so as to avoid redundancy.

An embodiment of the invention is a novel method for producing a polypeptide containing a non-canonical amino acid. This production method includes a step of contacting a pyrrolysyl-tRNA synthetase (PylRS) from, for instance, an organism belonging to the order Methanomassiliicoccales or Thermoplasmatales with a non-canonical amino acid. This production method preferably further includes an incorporation step selected from step (a) of incorporating the non-canonical amino acid into the polypeptide with higher efficiency than in a case of using a cell-free protein synthesis system with PylRS of *Methanosarcina mazei* (MmPylRS) or step (b) of incorporating the non-canonical amino acid into the polypeptide with higher efficiency than in a case of using an *Escherichia coli* protein synthesis system with a vector carrying a gene for the PylRS under regulation by a glmS promoter or a case of using an *Escherichia coli* protein synthesis system with a vector carrying a gene for the PylRS under regulation by a glnS promoter. In this case, this production method may be used to highly efficiently produce a polypeptide containing a non-canonical amino acid. Note that the glmS promoter and the glnS promoter are each a promoter that fails to fall under a high-expression promoter (non-high expression promoter). The incorporation step in an embodiment of the invention also includes, for instance, a step of incorporating a non-canonical amino acid into a polypeptide with higher efficiency than when MmPylRS is used as the PylRS. The degree of "high efficiency" in an embodiment of the invention is, for instance, 1.1, 1.2, 1.3, 1.4, 1.5, 2.0, 5.0, 10.0, 20.0, 30.0, or 40.0 times efficiency of a comparative subject, or may be equal to or higher than any of them or may be between any two thereof.

An embodiment of the invention is a method for incorporating a non-canonical amino acid into a polypeptide, comprising: a step of contacting PylRS from an organism belonging to the order Methanomassiliicoccales or Thermoplasmatales with the non-canonical amino acid; and an incorporation step selected from step (a) of incorporating the non-canonical amino acid into the polypeptide with higher efficiency than in a case of using a cell-free protein synthesis system with MmPylRS or step (b) of incorporating the non-canonical amino acid into the polypeptide with higher efficiency than in a case of using an *Escherichia coli* protein synthesis system with a vector carrying a gene for the PylRS under regulation by a glmS promoter or a case of using an *Escherichia coli* protein synthesis system with a vector carrying a gene for the PylRS under regulation by a glnS promoter. This method may be used to efficiently incorporate a non-canonical amino acid into a polypeptide.

An embodiment of the invention is a a non-canonical amino acid incorporation system comprising PylRS from an organism belonging to the order Methanomassiliicoccales or Thermoplasmatales. From the viewpoint of efficiently incorporating a non-canonical amino acid into a protein, it is preferable that this non-canonical amino acid incorporation system contains highly concentrated PylRS from an organism belonging to the order Methanomassiliicoccales or Thermoplasmatales.

An embodiment of the invention is a reaction solution for a cell-free protein synthesis system, comprising PylRS from an organism belonging to the order Methanomassiliicoccales or Thermoplasmatales. This reaction solution can include highly concentrated PylRS. This makes it possible to highly efficiently produce a polypeptide containing a non-canonical amino acid.

An embodiment of the invention is a method for producing a polypeptide containing a non-canonical amino acid, comprising the step of contacting PylRS from an organism belonging to the order Methanomassiliicoccales or Thermoplasmatales with the non-canonical amino acid extracellularly. This production method may be implemented using a reaction solution for a cell-free protein synthesis system. This reaction solution can include highly concentrated PylRS. This makes it possible to highly efficiently produce a polypeptide containing a non-canonical amino acid.

An embodiment of the invention is a method for incorporating a non-canonical amino acid into a polypeptide, comprising the step of contacting PylRS from an organism belonging to the order Methanomassiliicoccales or Thermoplasmatales with the non-canonical amino acid extracellularly. This incorporation method may be implemented using a reaction solution for a cell-free protein synthesis system. This reaction solution can include highly concentrated PylRS. This makes it possible to efficiently incorporate a non-canonical amino acid into a polypeptide.

An embodiment of the invention is a method for producing tRNA bound to a non-canonical amino acid, comprising the step of contacting PylRS from an organism belonging to the order Methanomassiliicoccales or Thermoplasmatales with the non-canonical amino acid and the tRNA extracellularly. This production method may be implemented using a reaction solution for a cell-free protein synthesis system. This makes it possible to highly efficiently produce tRNA bonded to a non-canonical amino acid.

An embodiment of the invention is purified PylRS from an organism belonging to the order Methanomassiliicoccales or Thermoplasmatales. A solution containing this PylRS may be enriched to prepare a solution containing PylRS at a high concentration. This solution may be utilized for a cell-free protein synthesis system to highly efficiently produce a polypeptide containing a non-canonical amino acid.

An embodiment of the invention is a solution comprising PylRS from an organism belonging to the order Methanomassiliicoccales or Thermoplasmatales. It is preferable that this solution contains 5 mg/mL or higher PylRS. In this case, this solution and a solution containing, for instance, a non-canonical amino acid and/or tRNA may be mixed to produce a reaction solution for a cell-free protein synthesis system. The resulting solution may be utilized for a cell-free protein synthesis system to highly efficiently produce a polypeptide containing a non-canonical amino acid. In an embodiment of the invention, the solution optionally includes, for instance, a buffer, NaCl, or a reductant.

An embodiment of the invention is an agent for incorporating a non-canonical amino acid into a polypeptide, comprising the above reaction solution or another type of solution. This incorporation agent may be utilized for a cell-free protein synthesis system to highly efficiently incorporate a non-canonical amino acid into a polypeptide.

An embodiment of the invention is a polynucleotide that encodes PylRS from an organism belonging to the order Methanomassiliicoccales or Thermoplasmatales. It is preferable that this polynucleotide also encodes a high-expression promoter. In this case, this polynucleotide may be utilized for a living-cell protein synthesis system to highly efficiently produce a polypeptide containing a non-canonical amino acid. Examples of the polynucleotide include a vector. The high-expression promoter may be positioned upstream of PylRS. The high-expression promoter may be linked in the polynucleotide so as to be able to regulate expression of PylRS.

An embodiment of the invention is a method for producing a polypeptide containing a non-canonical amino acid, comprising the step of incorporating the above polynucleotide into a cell or the step of expressing PylRS from the above polynucleotide. The production method may be utilized for a living-cell protein synthesis system to highly efficiently produce a polypeptide containing a non-canonical amino acid. This production method optionally includes, for instance, a step of ligating the polynucleotide to a vector; a step of incorporating a tRNA-encoding polynucleotide into a cell; a step of culturing the cell; a step of evaluating expression of PylRS; a step of evaluating expression of the polypeptide containing a non-canonical amino acid; or a step of purifying or isolating the polypeptide containing a non-canonical amino acid. The vector may be, for instance, an expression vector, a circular vector, or a plasmid.

An embodiment of the invention is a cell comprising a polynucleotide that encodes PylRS from an organism belonging to the order Methanomassiliicoccales or Thermoplasmatales and a high-expression promoter. This cell may be utilized for a living-cell protein synthesis system to highly efficiently produce a polypeptide containing a non-canonical amino acid.

An embodiment of the invention is a method for incorporating a non-canonical amino acid into a polypeptide, comprising the step of incorporating the above polynucleotide into a cell or the step of expressing PylRS from the above polynucleotide. This production method may be utilized for a living-cell protein synthesis system to highly efficiently incorporate a non-canonical amino acid into a polypeptide. This incorporation method optionally includes the same step(s) as the step(s) included in the above production method.

An embodiment of the invention is an agent for incorporating a non-canonical amino acid into a polypeptide, comprising the above polynucleotide. This incorporation agent may be utilized for a living-cell protein synthesis system to highly efficiently incorporate a non-canonical amino acid into a polypeptide.

An embodiment of the invention is a method for producing tRNA bonded to a non-canonical amino acid, comprising the step of incorporating the above polynucleotide into a cell or the step of expressing PylRS from the above polynucleotide. The production method may be utilized for a living-cell protein synthesis system to highly efficiently produce tRNA bonded to a non-canonical amino acid. This production method optionally includes, for instance, a step of incorporating a polynucleotide encoding PylRS into a cell; a step of culturing the cell; a step of evaluating expression of PylRS; a step of evaluating expression of tRNA; a step pf evaluating expression of the polypeptide containing a non-canonical amino acid; or a step of purifying or isolating the polypeptide containing a non-canonical amino acid.

An embodiment of the invention is a method for producing a polypeptide containing a non-canonical amino acid, comprising the step of expressing, at a high level in a living cell, PylRS from an organism belonging to the order Methanomassiliicoccales or Thermoplasmatales. The production method may be utilized for a living-cell protein synthesis system to highly efficiently produce a polypeptide containing a non-canonical amino acid. The step of expressing PylRS at a high level may include a step of expressing PylRS by using, for instance, a high-expression promoter.

In an embodiment of the invention, the production method or the incorporation method may be implemented in, for instance, a non-canonical amino acid incorporation system containing PylRS.

In an embodiment of the invention, the non-canonical amino acid incorporation system may be, for instance, a reaction solution for a cell-free protein synthesis system. In an embodiment of the invention, the concentration of PylRS in the reaction solution may be 15, 16, 17, 18, 19, 20, 25, 30, 40, 50, 60, 70, 80, 90, 100, or 120 μM, or may be equal to or higher than any of them or may be between any two thereof. From the viewpoint of efficiently incorporating a non-canonical amino acid into a protein, the concentration is preferably 25 μM or higher, more preferably 50 μM or higher, and still more preferably 75 μM or higher. The reaction solution may comprise a polynucleotide encoding a gene having a stop codon at a position different from a naturally occurring position, tRNA, and/or a non-canonical amino acid. The concentration of the polynucleotide encoding a gene having a stop codon at a position different from a naturally occurring position may be, for instance, 0.1, 0.2, 0.3, 0.4, 0.5, 0.6, 0.7, 0.8, 0.9, 1.0, 1.2, 1.4, 1.6, 1.8, 2.0, 2.5, 3.0, 4.0, 5.0, or 10.0 mg/mL, or may be equal to or higher than any of them or may be between any two thereof. The position different from a naturally-occurring position encompasses a position corresponding to, for instance, a site of incorporating a non-canonical amino acid into a polypeptide. The position different from a naturally occurring position may be, for instance, a position corresponding to the inside of a constant region of an antibody. The concentration of the tRNA may be, for instance, 1.0, 2.0, 3.0, 4.0, 5.0, 6.0, 7.0, 8.0, 9.0, 10.0, 12.0, 14.0, 16.0, 18.0, or 20.0 μM, or may be equal to or higher than any of them or may be between any two thereof. The concentration of the non-canonical amino acid may be, for instance, 0.1, 0.2, 0.3, 0.4, 0.5, 0.6, 0.7, 0.8, 0.9, 1.0, 1.2, 1.4, 1.6, 1.8, 2.0, 2.5, 3.0, 4.0, 5.0, or 10.0 mM, or may be equal to or higher than any of them or may be between any two thereof. The reaction solution may contain, for instance, LMCPY mixture-PEG-DTT, tRNA, magnesium acetate, an amino acid mixture, creatine kinase, an RNA polymerase, chaperone enhanced S30 extract, a buffer, a template DNA, GSSG, DsbC, a pH modifier, or water. The concentration of each component may be within ±40, ±30, ±20, ±10, or ±5% of the concentration listed in Table 2 described below. The template DNA may be a nucleic acid containing a nonsense codon in a nucleotide sequence encoding a protein that is a target for amino acid incorporation. Examples of the cell-free protein synthesis system that can be utilized in an embodiment of the invention include an *Escherichia coli*-derived, cell-free protein synthesis system, a mammalian cell-derived, cell-free protein synthesis system, an insect cell-derived, cell-free protein synthesis system, a wheat germ-derived, cell-free protein synthesis system, or a reconstituted, cell-free protein synthesis system.

In an embodiment of the invention, the non-canonical amino acid incorporation system may be a cell for a living-cell protein synthesis system. In an embodiment of the invention, the cell may comprise a polynucleotide encoding PylRS and a high-expression promoter. In an embodiment of the invention, examples of the high-expression promoter include a promoter that can drive expression of a polypeptide (e.g., PylRS) at a high level. Examples of the high-expression promoter include a promoter that can drive expression at a higher level than the glmS promoter and the glnS promoter. Examples of the high-expression promoter that can regulate PylRS include a phage-derived high-expression promoter (e.g., T3, T5, T7, SP6) or a high-expression promoter (e.g., tac, trc, lac, lacUV5, araBAD, rhaBAD, SV40, CMV, CAG, SV40, EF-1α, TEF1, PGK1, HXT71, TPI1, TDH3, PYK1, ADH1, GAL1, GAL10, polyhedrin, p10, metallothionein, or Actin 5C). In the *Escherichia coli* culture system, the high-expression promoter is preferably T3, T5, T7, SP6, tac, trc, lac, lacUV5, araBAD, or rhaBAD. In the mammalian cell culture system, the high-expression promoter is preferably SV40, CMV, CAG, SV40, or EF-1α. In the budding yeast (*S. cerevisiae*) culture system, the high-expression promoter is preferably TEF1, PGK1, HXT71, TPI1, TDH3, PYK1, ADH1, GAL1, or GAL10. In the fission yeast (*Schizosaccharomyces pombe*) culture system, the high-expression promoter is preferably CMV. In the insect cell (e.g., a moth cell that can be infected with a baculovirus) culture system, the polyhedrin or p10 is preferable. In the insect cell (e.g., *Drosophila* S2 cell) culture system, metallothionein or Actin 5C is preferable. Examples of the promoter that can regulate and drive expression of tRNA at a high level include a U6, H1, 7SK, tRNA (Val), tRNA (Arg), tRNA (Tyr), lpp, or T5 promoter. In the mammalian cell culture system or the insect cell culture system, this promoter is preferably a U6, H1, 7SK, tRNA (Val), tRNA (Arg), or tRNA (Tyr) promoter; and in the *Escherichia coli* culture system, this promoter is preferably lpp or T5. In an embodiment of the invention, the living-cell protein synthesis system may use, for instance, a bacteria (e.g., *Escherichia coli*) cell, a mammalian cell, an insect cell, or yeast.

In an embodiment of the invention, the non-canonical amino acid incorporation system is applicable to a non-canonical amino acid incorporation system containing multiple orthogonal pairs.

When the concentration of PylRS in the reaction solution in an embodiment of the invention is a high concentration, examples of the concentration include 15 μM or higher. This concentration may be, for instance, 15, 16, 17, 18, 19, 20, 25, 30, 40, 50, 60, 70, 80, 90, 100, or 120 μM, or may be equal to or higher than any of them or may be between any two thereof. From the viewpoint of efficiently incorporating a non-canonical amino acid into a protein, the concentration is preferably 25 μM or higher, more preferably 50 μM or higher, and still more preferably 75 μM or higher.

In an embodiment of the invention, the production method optionally includes a step of mixing a solution containing 5 mg/mL or higher PylRS from an organism belonging to the order Methanomassiliicoccales or Thermoplasmatales and a non-canonical amino acid to prepare a mixed solution. This mixed solution can include highly concentrated PylRS. The mixed solution containing highly concentrated PylRS may be utilized for a cell-free protein synthesis system to highly efficiently produce a polypeptide containing a non-canonical amino acid.

The concentration of PylRS at 5 mg/mL or higher in an embodiment of the invention may be, for instance, 5, 6, 7, 8, 9, 10, 12, 14, 16, 18, 20, 25, 26, 27, 28, 29, or 30 mg/mL, or may be equal to or higher than any of them or may be between any two thereof. Regarding the above case of 5 mg/mL or higher, 12.6 mg/mL or higher concentration makes the preparation easier in a particularly highly efficient cell-free protein synthesis system. From this viewpoint, 12.6 mg/mL or higher is preferable, 15 mg/mL or higher is more preferable, and 20 mg/mL or higher is still more preferable.

Examples of the cell-free protein synthesis system in an embodiment of the invention include: a synthesis system in which extract from PylRS-expressing cells, crude PylRS, or purified PylRS is added at a high concentration to a reaction solution containing cell extract from, for instance, *Escherichia coli* as prepared for cell-free protein synthesis; or a synthesis system in which cell extract prepared from, for instance, *Escherichia coli* expressing, at a high concentration, PylRS created for cell-free protein synthesis is used for a reaction solution.

In an embodiment of the invention, examples of the polypeptide containing a non-canonical amino acid include a polypeptide bonded with drug(s). Examples of the drug include an anti-cancer agent.

In an embodiment of the invention, examples of PylRS include a protein having an activity of bonding an amino acid to tRNA. Examples of the amino acid include pyrrolysine or a non-canonical amino acid. In an embodiment of the invention, examples of the non-canonical amino acid include a lysine derivative, tyrosine derivative, phenylalanine derivative, tryptophan derivative, arginine derivative, methionine derivative, leucine derivative, histidine derivative, proline derivative, cysteine derivative, threonine derivative, serine derivative, alanine derivative, isoleucine derivative, valine derivative, glutamine derivative, glutamic acid derivative, asparagine derivative, aspartic acid derivative, glycine derivative, selenocysteine derivative, pyrrolysine derivative, kynurenine derivative, ornithine derivative, citrulline derivative, canavanine derivative, or diaminopimelic acid, or an α-hydroxy acid derivative thereof. Unless otherwise indicated, examples of PylRS include any of a wild-type PylRS or mutant PylRS.

Organisms belonging to the order Methanomassiliicoccales or Thermoplasmatales form a group of population and are distant from organisms belonging to the genus *Methanosarcina* such as *Methanosarcina mazei* or *Methanosarcina barkeri*. When aligned with the amino acid sequence of PylRS from *Methanosarcina barkeri* or *Methanosarcina mazei*, the amino acid sequences of PylRS from organisms belonging to the order Methanomassiliicoccales or Thermoplasmatales may each have a structure lacking an amino acid sequence on the N-terminal side.

In an embodiment of the invention, examples of the organism belonging to the order Methanomassiliicoccales include an organism belonging to the genus Methanomethylophilus, Methanomassiliicoccus, or Methanoplasma. Meanwhile, the organism belonging to the order Methanomassiliicoccales may include an organism for which the genus has not been classified. Examples of the organism belonging to the genus Methanomethylophilus include Methanomethylophilus alvus (M. alvus) (WP_015505008), or Methanomethylophilus sp. 1R26 (WP_058747239). Examples of the organism belonging to the genus Methanomassiliicoccus include Methanomassiliicoccus luminyensis (WP_019176308) or Methanomassiliicoccus intestinalis (WP_020448777). Examples of the organism belonging to the genus Methanoplasma include Methanoplasma *termitum* (WP_048111907). Examples of the organism for which the genus is not classified include a Methanomassiliicoccales archaeon RumEn M1 (KQM11560), a methanogenic archaeon ISO4-H5 (WP_066075773), or a methanogenic archaeon ISO4-G1 (AMK13702). Note that parentheses after the organism nomenclature include and indicate the NCBI Accession Number of PylRS.

In an embodiment of the invention, examples of the organism belonging to the order Thermoplasmatales include an organism for which the genus has not been classified. Examples of the organism for which the genus has not been classified include a Thermoplasmatales archaeon BRNA1 (WP_015492598).

Figure 1:
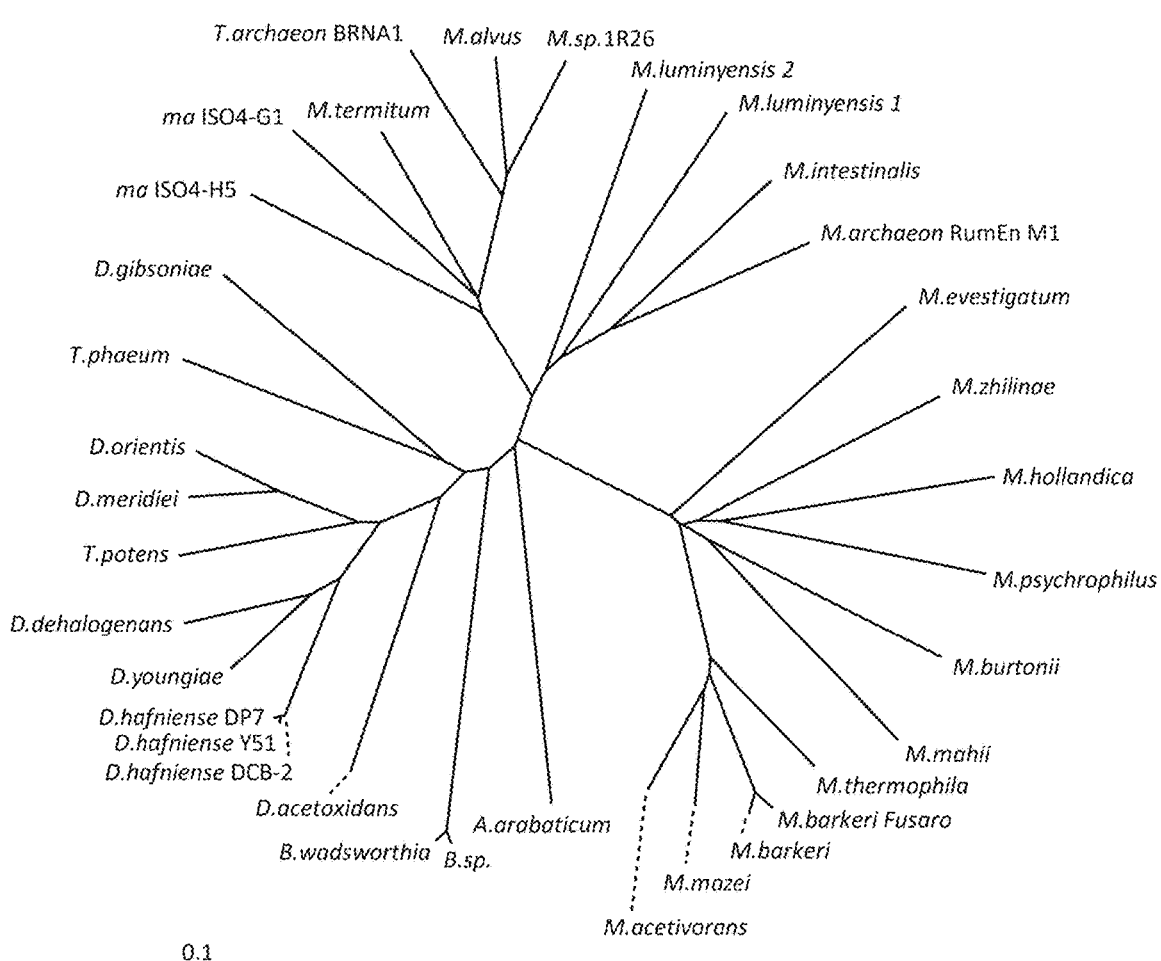
FIG. 1 is a diagram illustrating an example of a phylogenetic tree including organisms belonging to the genus Methanomethylophilus or Methanomassiliicoccus.

FIG. 1 shows an example of a phylogenetic tree including organisms belonging to the genus Methanomethylophilus or Methanomassiliicoccus. From the viewpoint of efficiently incorporating a non-canonical amino acid into a protein, the organism is preferably Methanomethylophilus alvus or a methanogenic archaeon ISO4-G1. Methanomethylophilus alvus may be generally referred to as *Candidatus* Methanomethylophilus alvus. Accordingly, Methanomethylophilus alvus herein includes *Candidatus* Methanomethylophilus alvus. In addition, regarding the other organisms (e.g., the genus or species), organisms corresponding to *Candidatus*-containing nomenclature encompass organisms designated by nomenclature without the name *Candidatus*. That is, organisms identified as *Candidatus* X should be included in organisms identified as X.

Examples of MaPylRS in an embodiment of the invention include a protein having the amino acid sequence set forth in SEQ ID NO: 5. Examples of G1PylRS in an embodiment of the invention include a protein having the amino acid sequence set forth in SEQ ID NO: 10. When aligned with amino acid sequences of PylRS of archaea such as *Methanosarcina barkeri* and *Methanosarcina mazei*, amino acid sequences of MaPylRS and G1PylRS lack an N-terminal region. FIG. 2 shows the alignment using Clustal Omega. The boxed portions are assumed to be portions of a pyrrolysine-binding pocket. In an embodiment of the invention, the amino acid sequence of PylRS from an organism belonging to the order Methanomassiliicoccales or Thermoplasmatales may have 70% or higher homology to the amino acid sequence of MaPylRS. This number may be, for instance, 70, 75, 80, 85, 90, 95, 97, 98, 99, or 100%, or may be between any two thereof.

Examples of PylRS in an embodiment of the invention include PylRS with an amino acid sequence lacking at least 50 amino acids on the N-terminal side when aligned with amino acid sequences of PylRS of archaea such as *Methanosarcina barkeri* and *Methanosarcina mazei*. This number may be 50, 60, 70, 80, 90, 100, 110, 120, 130, 140, 150, 160, 170, 180, or 185, or may be between any two thereof. From the viewpoint of efficiently incorporating a non-canonical amino acid into a protein, at least 110 amino acids are preferable and at least 130 amino acids are more preferable. The alignment may be conducted using, for instance, Clustal Omega or NCBI BLAST.

Examples of PylRS in an embodiment of the invention include PylRS bound, at an amino acid-binding pocket, to a non-canonical amino acid. Examples of an amino acid of the amino acid-binding pocket includes an amino acid at position 96, 120, 121, 122, 125, 126, 129, 164, 166, 168, 170, 203, 204, 205, 206, 207, 221, 223, 227, 228, 233, 235, 239, 241, or 243 when aligned with those of MaPylRS. Examples of an amino acid of the amino acid-binding pocket includes an amino acid at position 95, 119, 120, 121, 124, 125, 128, 163, 165, 167, 169, 201, 202, 203, 204, 205, 219, 221, 225, 226, 231, 233, 237, 239, or 241 when aligned with those of ISO4-G1 PylRS. Examples of PylRS in an embodiment of the invention include PylRS bound, at the amino acid-binding pocket, to a non-canonical amino acid (e.g., a lysine derivative).

Examples of purified PylRS in an embodiment of the invention include isolated PylRS. Examples of PylRS include PylRS synthesized in a cell-free protein synthesis system or recombinant PylRS expressed in living cells. Examples of the cell in an embodiment of the invention include an *Escherichia coli* or mammalian cell. Examples of the mammal in an embodiment of the invention include a human, rat, mouse, rabbit, cow, or monkey. Examples of purified PylRS include PylRS purified through HisTrap purification or a purification protocol such as gel filtration chromatography.

Examples of the mutant PylRS in an embodiment of the invention include a mutant PylRS having an amino acid sequence with 70% or higher homology to the amino acid sequence of naturally occurring PylRS and having pyrrolysyl-tRNA synthetase activity. The homology may be, for instance, 70, 75, 80, 85, 90, 95, 97, 98, 99, 99.5, 99.9%, or higher, or may be between any two thereof. The homology may be less than 100%. The homology may be a percentage of the number of identical amino acids between two or more amino acid sequences as calculated in accordance with a known procedure in the art. Prior to the percentage calculation, amino acid sequences of an amino acid sequence group to be compared are aligned. Next, the percentage of identical amino acids should be maximized. For this purpose, a gap(s) may be inserted in some portions of each amino acid sequence. The alignment procedure, the percentage calculation method, the comparison process, and related computer programs (e.g., BLAST, GENETYX) have been well-known in the art. The homology may be represented by a value measured using NCBI BLAST. The amino acid sequence may be compared using Blastp under default setting. Note that as used herein, a mutant PylRS and a PylRS mutant have the same meaning.

Examples of the pyrrolysyl-tRNA synthetase activity in an embodiment of the present invention include an activity of bonding a non-canonical amino acid to tRNA. Examples of the activity includes an activity of bonding a non-canonical amino acid to a suppressor tRNA. Examples of the activity include an activity of incorporating a non-canonical amino acid into a protein.

Examples of the mutant PylRS in an embodiment of the invention include a mutant PylRS having pyrrolysyl-tRNA synthetase activity and having an amino acid sequence encoded by a polynucleotide specifically hybridized under stringent conditions with a polynucleotide consisting of a nucleotide sequence complementary to a nucleotide sequence encoding the amino acid sequence of naturally occurring PylRS. The following conditions, for instance, may be employed as the stringent conditions. (1) Washing is conducted with a low ionic strength at a high temperature (e.g., 0.015 M sodium chloride/0.0015M sodium citrate/0.1% sodium dodecyl sulfate at 50° C.) or (2) a denaturing agent such as formamide is used during hybridization (e.g., 50% (v/v) formamide, 0.1% bovine serum albumin/0.1% ficoll/0.1% polyvinylpyrrolidone/50 mM sodium phosphate buffer at pH 6.5, 750 mM sodium chloride, and 75 mM sodium citrate at 42° C.). Note that the temperature during washing may be 50, 55, 60, or 65° C., or a number between any two thereof. The washing period may be 5, 15, 30, 60, or 120 min or longer. The factor that affects the stringency during the hybridization reaction may involve multiple factors such as a temperature and a salt concentration. Regarding the details, one can consult Ausubel et al., Current Protocols in Molecular Biology, Wiley Interscience Publishers, (1995).

Examples of the mutant PylRS in an embodiment of the invention include a mutant PylRS having one or several amino acid residue deletions, additions, insertions, or substitutions in the naturally occurring PylRS and having pyrrolysyl-tRNA synthetase activity. The term "several" may refer to 2, 3, 4, 5, 6, 7, 8, 9, or 10, or may refer to a number between any two thereof. Polypeptides with one or several amino acid residue deletions, additions, insertions, or substitutions are known to keep their biological activity (Mark et al., Proc Natl Acad Sci USA., 1984 September, 81 (18): 5662-5666; Zoller et al., Nucleic Acids Res., 1982 Oct. 25, 10 (20): 6487-6500; Wang et al., Science, 1984 Jun. 29, 224 (4656): 1431-1433). A polypeptide with, for instance, a deletion(s) may be created by, for example, site-directed mutagenesis or random mutagenesis. For instance, it is possible to use, as the site-directed mutagenesis, Prime-STAR mutagenesis kit (Takara Bio Inc.).

Examples of the amino acid in an embodiment of the invention include any organic compound having an amino group and a carboxyl group. When the polypeptide in an embodiment of the invention contains a specific amino acid sequence, any of amino acids in the amino acid sequence may form a salt or a solvate. In addition, any of amino acids in the amino acid sequence may be in an L-form or D-form. Even in such cases, the polypeptide in an embodiment of the invention can be said to contain the above specific amino acid sequence.

Examples of the mutant PylRS in an embodiment of the invention include PylRS with a mutation in the amino acid-binding pocket. Examples of the mutant PylRS in an embodiment of the invention include PylRS bound, at the amino acid-binding pocket, to a non-canonical amino acid (e.g., a lysine derivative).

Examples of the mutant PylRS in an embodiment of the invention include PylRS with a mutation at position 96, 120, 121, 122, 125, 126, 128, 129, 164, 166, 168, 170, 203, 204, 205, 206, 207, 221, 223, 227, 228, 233, 235, 239, 241, or 243 when aligned with those of the naturally occurring PylRS. These positions may be mutable sites as judged from the results of mutagenesis experiment or crystallography. This mutation may be a mutation to, for instance, A, R, N, D, C, Q, E, G, H, I, L, K, M, F, P, S, T, W, Y, or V. It is preferable that this mutation is a mutation to A, L, V, C, or F. For instance, Y, M, V, and Y may be at positions, in sequence, 126, 129, 168, and 206 before the mutation.

Examples of the mutant PylRS in an embodiment of the invention include a mutant PylRS having higher efficiency of incorporating a non-canonical amino acid into a protein than the naturally occurring PylRS. Examples of the mutant PylRS in an embodiment of the invention include a mutant PylRS having an activity of incorporating TCO*Lys, pEtZLys, or pAzZLys into a protein.

An embodiment of the invention is a composition for bonding a non-canonical amino acid to tRNA, comprising PylRS from an organism belonging to the order Methanomassiliicoccales or Thermoplasmatales. It is preferable that this bond-use composition contains 5 mg/mL or higher PylRS. In this case, this bond-use composition and a solution containing a non-canonical amino acid and/or tRNA, for instance, may be mixed to efficiently bond the non-canonical amino acid to tRNA. This bond-use composition may be used for synthesis of a polypeptide containing a non-canonical amino acid to efficiently produce the polypeptide containing a non-canonical amino acid. An embodiment of the invention is use of PylRS from an organism belonging to the order Methanomassiliicoccales or Thermoplasmatales in the manufacture of a composition for bonding non-canonical amino acid to tRNA. An embodiment of the invention is a method for bonding a non-canonical amino acid to tRNA, comprising using PylRS from an organism belonging to the order Methanomassiliicoccales or Thermoplasmatales.

In an embodiment of the invention, the method for incorporating a non-canonical amino acid into a polypeptide, the method for efficiently producing a polypeptide containing a non-canonical amino acid, the method for bonding a non-canonical amino acid to tRNA, or the method for producing tRNA bound to a non-canonical amino acid optionally includes, for instance, any of the following steps. Step (1) of contacting PylRS with a non-canonical amino acid; step (2) of contacting PylRS with tRNA; step (3) of putting PylRS, a PylRS-encoding nucleic acid, or a non-canonical amino acid in a solution; step (4) of putting tRNA or a tRNA-encoding nucleic acid into a solution; step (5) of contacting tRNA with a polynucleotide encoding a gene having a stop codon at a position different from a naturally occurring position; or step (6) of expressing, under the presence of a non-canonical amino acid, PylRS, tRNA, or a polynucleotide encoding a gene having a stop codon at a position different from a naturally occurring position. In addition, it is possible to include a step of concentrating a PylRS-containing solution or a step of mixing a concentrated PylRS solution and a non-canonical amino acid. Examples of the tRNA include a suppressor tRNA. Examples of the suppressor tRNA include an amber suppressor tRNA. Examples of the tRNA include tRNA from an organism belonging to the order Methanomassiliicoccales or Thermoplasmatales. Unless otherwise indicated, examples of the tRNA include any of a naturally occurring tRNA or a mutant tRNA. The solution may comprise, for instance, a buffer, tRNA, a polynucleotide encoding a gene having a stop codon at a position different from a naturally occurring position, an amino acid mixture, a template DNA, and/or an RNA polymerase. It is possible to use, in a cell-free protein synthesis process or cell protein synthesis process, the method for incorporating a non-canonical amino acid into a polypeptide or the method for producing a polypeptide containing a non-canonical amino acid.

Examples of the protein in an embodiment of the invention include a functional protein or a structural protein. Examples of the functional protein include an antibody or an enzyme. The protein may contain a naturally occurring amino acid or a non-canonical amino acid. The site where a non-canonical amino acid is incorporated may be, for instance, within a constant region of antibody.

Examples of the polypeptide in an embodiment of the invention include a protein. Examples of the polypeptide include a structure in which a plurality of amino acids are bonded. The number of amino acids in the polypeptide is, for instance, 10, 20, 30, 50, 70, 100, 200, 400, 500, 700, 1000, or 1500, or may be equal to or higher than any of them or may be between any two thereof.

Examples of the lysine derivative in an embodiment of the invention include each compound in FIG. 3. Examples of the non-canonical amino acid include each non-canonical amino acid disclosed in WO/2017/030156. Examples of the non-canonical amino acid include, for instance, any amino acid derivative. Examples of the phenylalanine derivative include 3-iodo-L-phenylalanine. Examples of the tyrosine derivative include o-propargyl-L-tyrosine.

An embodiment of the invention is a composition. Examples of this composition include a solution comprising PylRS from an organism belonging to the order Methanomassiliicoccales or Thermoplasmatales. Examples of the composition include a composition for incorporating a non-canonical amino acid into a polypeptide or a composition for producing a polypeptide containing a non-canonical amino acid. The composition may comprise, for instance, a non-canonical amino acid. The composition may comprise, for instance, a buffer, tRNA, a template DNA, an amino acid mixture and/or an RNA polymerase.

An embodiment of the invention is a polypeptide containing a non-canonical amino acid. This polypeptide may be chemically modified by click chemistry. For click chemistry, for instance, a technology (Hou J et al., Expert Opin Drug Discov. 2012 June, 7 (6): 489-501; Bonnet D et al., Bioconjug Chem. 2006 November-December, 17 (6): 1618-23) is available. An embodiment of the invention is chemically modified polypeptide containing a non-canonical amino acid. An embodiment of the invention is a polypeptide or chemically modified polypeptide containing a non-canonical amino acid. Examples of the composition include a pharmaceutical composition containing at least one pharmacologically acceptable carrier.

An embodiment of the invention is a template-use composition for producing a mutant PylRS, comprising PylRS from an organism belonging to the order Methanomassiliicoccales or Thermoplasmatales. An embodiment of the invention is a method for producing a mutant PylRS, comprising the step of incorporating a mutation into PylRS from an organism belonging to the order Methanomassiliicoccales or Thermoplasmatales. Whether a mutated PylRS has pyrrolysyl-tRNA synthetase activity may be evaluated in a cell-free protein synthesis process or a living-cell protein synthesis process as demonstrated in, for instance, the below-described Examples. An embodiment of the invention is a method for producing a polypeptide, comprising a step of contacting PylRS from an organism belonging to the order Methanomassiliicoccales or Thermoplasmatale with an amino acid; and an incorporation step selected from step (a) of incorporating the amino acid into the polypeptide with higher efficiency than in a case of using a cell-free protein synthesis system with MmPylRS or step (b) of incorporating the non-canonical amino acid into the polypeptide with higher efficiency than in a case of using an *Escherichia coli* protein synthesis system with a vector carrying a gene for the PylRS under regulation by a glmS promoter or a case of using an *Escherichia coli* protein synthesis system with a vector carrying a gene for the PylRS under regulation by a glnS promoter. An embodiment of the invention is an amino acid incorporation system comprising highly concentrated PylRS from an organism belonging to the order Methanomassiliicoccales or Thermoplasmatales. The amino acid incorporation system may involve, for instance, a reaction solution for a cell-free protein synthesis system or a cell for a living-cell protein synthesis system. An embodiment of the invention is a method for producing a polypeptide, comprising the step of contacting PylRS from an organism belonging to the order Methanomassiliicoccales or Thermoplasmatale with an amino acid extracellularly. An embodiment of the invention is a method for producing a polypeptide, comprising the step of expressing, at a high level in a living cell, PylRS from an organism belonging to the order Methanomassiliicoccales or Thermoplasmatales.

All the literatures and (patent or patent application) publications cited herein are incorporated by reference in its entirety.

As used herein, the term "or" is used when "at least one" matter listed in the text is acceptable. The same applies to "or". When the wording "number between any two" is indicated herein, this range encompasses the two numbers inclusive. The wording "from A to B" herein means A or more and B or less.

Hereinabove, embodiments of the invention have been described. However, they are examples of the invention. Hence, it is possible to employ various configurations other than the above. In addition, the configurations described in the above embodiments may be combined and then adopted.

EXAMPLES

Hereinbelow, the invention will be described in more detail with reference to Examples. However, the invention is not limited to them.

Experimental Example 1

(1) Expression and Purification of *Methanosarcina mazei* PylRS (MmPylRS)

First, a His6-SUMO-MmPylRS structural gene was cloned into pET24 and transformed into *Escherichia coli* BL21-Gold (DE3), which was then cultured in 1-L LB broth at 37° C. Next, when OD600=0.7, 1 mM IPTG was added, and the culturing was continued over day and night at 20° C. (the amino acid sequence of His6-SUMO-MmPylRS is set forth in SEQ ID NO: 1). Then, the cells were collected, and HisTrap purification and SUMO protease treatment were carried out. After that, HiTrap SP, Superdex 200 HiLoad16/60 purification was performed to recover 4.4 mg of MmPylRS (2.82 mg/ml×1.56 ml) from the 1-L broth. After this MmPylRS-containing solution was concentrated, the concentration limit was 2.82 mg/mL.

Example 1

1.1 Expression and Purification of Methanomethylophilus Alvus PylRS (MaPylRS)

First, a MaPylRS structural gene (SEQ ID NO: 2) was cloned into pET28 and transformed into *Escherichia coli* BL21-Gold (DE3), which was then cultured in 1-L LB broth at 37° C. Next, when OD600=0.6, 1 mM IPTG was added, and the culturing was continued over day and night at 20° C. Then, the cells were collected, and HisTrap purification, thrombin treatment, and HiTrapQ, Hitrap Heparin, Superdex 200 purification were performed to recover about 100 mg of MaPylRS from the 1-L broth. This recovery amount was higher than in the case of conventional archaea PylRS. In the case of expressing, in *Escherichia coli*, PylRS from the genus *Methanosarcina*, the recovery amount was small because the PylRS was readily precipitated and its purification was difficult. After this MaPylRS-containing solution was concentrated, the concentration limit was 20 mg/mL or higher.

Example 2

2.1 to Compare Yield of Protein Having Non-Canonical Amino Acid Incorporated while MaPylRS or MmPylRS was Used in Cell-Free Protein Synthesis Process.

The reaction solution and the dialysis external solution were as provided in Table 1.

TABLE 1

| Stock solution | Final concentration | Reaction solution | Dialysis External Solution |
|---|---|---|---|
| LMCPY mixture-PEG | 37.33% | 11.2 μL | 373.3 μL |
| 17.5 mg/mL tRNA | 0.175 mg/mL | 0.3 μL | — |
| 5% sodium azide | 0.05% | 0.3 μL | 10 μL |
| 1.6M magnesium acetate | 10 mM | 0.1875 μL | 6.25 μL |
| 20 mM amino acid mixture | 1.5 mM | 2.25 μL | 75 μL |
| 3.75 mg/mL creatine kinase | 0.1 mg/mL | 0.8 μL | — |
| 10 mg/mL T7 RNA polymerase | 0.067 mg/mL | 0.2 μL | — |
| S30 extract | 30% | 9 μL | — |
| S30 buffer | 30% | — | 300 μL |
| 100 μg/mL Template DNA | 2 μg/mL | 0.6 μL | — |
| 1.25 mM tRNA$^{Pyl}$ | 10 μM | 0.24 μL | — |
| 75 μM PylRS | 10 μM | 4 μL | — |
| KOH or HCl for pH adjustment | 1/2 volume of ncAA | 0.3 μL | 15 μL |
| 50 mM ncAA | 1 mM | 0.6 μL | 30 μL |
| Milli-Q water | | 0.022 μL | 190.5 μL |
| Total | | 30 μL | 1 mL |

*Methanosarcina mazei* tRNA$^{Pyl}$ or Methanomethylophilus alvus tRNA$^{Pyl}$ (the nucleotide sequence was set forth in SEQ ID NO: 3) was used as tRNA$^{Pyl}$, and the wild-type MmPylRS or MaPylRS (the amino acid sequence of MmPylRS is set forth in SEQ ID NO: 4 and the amino acid sequence of MaPylRS is set forth in SEQ ID NO: 5), respectively, was used. N$^{ε}$-(tert-butyloxycarbonyl)-L-lysine (BOCLys) (Bachem, Inc.) or N$^{ε}$-propargyloxycarbonyl-L-lysine (PocLys) (SciChem, Inc.) was used as a non-canonical amino acid. Next, pN11GFPS1sh-A17Amb or pN11GFPS1sh was used as the template DNA for non-canonical amino acid incorporation or control synthesis, respectively. Then, the synthesis reaction was carried out while 30 μL of the reaction solution was dialyzed overnight at 25° C. against 1 mL of the dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1, and was expressed as the percentage with respect to the percentage for control normal synthesis.

The results have demonstrated that each PylRS was used to incorporate a non-canonical amino acid as shown in FIG. 4. In the case of BOCLys incorporation, the amount of protein synthesized using MaPylRS was twice or larger than that using MmPylRS, indicating that the protein synthesis was equivalent to the control normal synthesis (WT). In the case of PocLys incorporation, the amount of protein synthesized using MaPylRS was very large, and the amount synthesized was substantially the same as that of control. Thus, the results have revealed that use of MaPylRS allows a non-canonical protein to be prepared efficiently.

Example 3

3.1 Wild-Type PylRS Concentration Dependence in Cell-Free Protein Synthesis Process In the case of TCO*Lys incorporation, the concentration dependence when naturally occurring PylRS was used was evaluated. The reaction solution and the dialysis external solution were as provided in Table 1. Methanomethylophilus alvus tRNA$^{Pyl}$ was used as tRNA$^{Pyl}$. The wild-type MaPylRS was used as PylRS.

The upper limit of the PylRS amount that can be added to the reaction solution is the total amount of liquid portion of water (Milli-Q water) corresponding to PylRS. Because the concentration limit of MaPylRS was 20 mg/mL or more, it was possible to add it at the final concentration of 80 μM or higher. The range used in this experiment was from 10 μM to 75 μM. Note that in the case of MmPylRS, the concentration limit was 4 mg/mL or lower, and as a result of which the maximum applicable concentration should be about 10 μM.

TCO*Lys was used as a non-canonical amino acid. Here, pN11GFPS1sh-A17Amb was used as a template DNA. The synthesis reaction was carried out while 30 μL of the reaction solution was dialyzed overnight at 25° C. against 1 mL of dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As shown in FIG. 5, the results have demonstrated that 10 μM or higher concentration caused the protein yield to increase, and the amount in the case of 75 μM PylRS was about 2.3 times higher than in the case of 10 μM PylRS.

Example 4

4.1 MaPylRS Crystallography

The MaPylRS recovered in Example 1 was subjected to crystallization screening to give a crystal under conditions in which PEG was used as a precipitant. Taiwan Beamline (TPS05A) was used to obtain diffraction data at a resolution of 2.2 Å (space group C2). Next, the data was subjected to molecular replacement using the MmPylRS structure and then structural refinement (Rf/Rw=28.8/22.8). The structure of the catalytic domain resembles that of MmPylRS, but the angles of two N-terminal α-helices are different from that of MmPylRS. An active site pocket is widely opened because Tyr206 (Phe384) does not enter the pocket and is bent and oriented inward due to several residues around Tyr206. The shape of the active site pocket in MaPylRS is somewhat distinct from that in MmPylRS, and the deep pocket portion seems to be a little narrower. Based on this structure, each PylRS mutant was created to conduct experiments of incorporating non-canonical amino acid.

The left panel of FIG. 6 shows a structure in which a monomer of the MmPylRS catalytic domain/pyrrolysyl AMP complex is superimposed on a dimer of MaPylRS (apo type; green and blue). The right panel of FIG. 6 shows an enlarged view of the active site in the structure where MmPylRSc and MaPylRS (apo type) are superimposed. In addition, depicted are each mutated amino acid residue, each corresponding amino acid residue in MmPylRS, and Asn346/Asn166 required for recognition of the carbonyl group of pyrrolysine.

Example 5

5.1 to Evaluate Each MaPylRS Mutant Created Based on Structural Analysis Results Each MaPylRS, the mutation site of which was determined on the basis of the structural analysis results, was used to evaluate incorporation of a non-canonical amino acid. The reaction solution and the dialysis external solution were as provided in Table 1. As tRNA$^{Pyl}$, 10 μM of Methanomethylophilus alvus tRNA$^{Pyl}$ was used. MaPylRS (Y126A/M129A/H227I/Y228P) or MaPylRS(Y126A/M129L/H227I/Y228P), as created by adding new mutations (H227I/Y228P), which were determined on the basis of the structural analysis results, to a conventional MaPylRS (Y126A/M129A) or MaPylRS(Y126A/M129L) mutant was used as MaPylRS. Here, 10 μM of each MaPylRS was used. The non-canonical amino acid used was ZLys, mAzZLys, pEtZLys, or TCO*Lys. The template DNA used was pN11GFPS1sh-A17Amb. The synthesis reaction was carried out while 30 μL of the reaction solution was dialyzed overnight at 25° C. against 1 mL of dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As a result, FIG. 7 shows that the H227I/Y228P mutations were incorporated into the MaPylRS(Y126A/M129A) mutant to markedly increase the protein yield in all the cases of non-canonical amino acid. In the case of ZLys, mAzZLys, or TCO*Lys, in particular, the yield reached the amount equivalent to the WT yield. The incorporation of the H227I/Y228P double mutation was found to cause about 3-fold increase in the case of Zlys, about 1.5-fold increase in the case of mAzZLys, about 1.6-fold increase in the case of pEtZLys, and about 9-fold increase in the case of TCO*Lys.

Next, the H227I/Y228P double mutations was also incorporated into the MaPylRS(Y126A/M129L) mutant having an effect in the case of TCO*Lys incorporation. Like the MaPylRS(Y126A/M129A) mutant, the yield reached the amount equivalent to the WT yield and was increased about 4-fold. This has suggested that the H227I/Y228P mutation may be effective in various mutants.

Example 6

6.1 PylRS Concentration Dependence when Non-Canonical Amino Acid was Incorporated Using Each PylRS Mutant in Cell-Free Protein Synthesis Process The reaction solution and the dialysis external solution were as provided in the above Table 1. At this time, each PylRS mutant was used as PylRS. Each PylRS mutant was checked at the final concentration between 5 μM and 75 μM. The amount of water (Milli-Q water) was changed as the liquid amount was changed while the concentration of each PylRS mutant was varied.

*Methanosarcina mazei* tRNA$^{Pyl}$ and Methanomethylophilus alvus tRNA$^{Pyl}$ were each used as tRNA$^{Pyl}$. MmPylRS (Y306A/Y384F/R61K) and MaPylRS(Y126A/M129L) were each used as a PylRS mutant. The MmPylRS(Y306A/Y384F/R61K) is among MmPylRS mutants, and is a mutant with an increased activity with respect to a large lysine derivative such as a ZLys derivative (Yanagisawa et al., Chem Biol., 2008 Nov. 24, 15 (11): 1187-97). The non-canonical amino acid used was N$^{ε}$-((((E)-cyclooct-2-en-1-yl)oxy)carbonyl)-L-lysine (TCO*Lys) (SciChem, Inc.), N$^{ε}$-(p-ethynylbenzyloxycarbonyl)-L-lysine (pEtZLys)(Sundia/Namiki, Inc.), or N$^{ε}$-(p-azidobenzyloxycarbonyl)-L-lysine (pAzZLys) (Sundia/Namiki, Inc.). Here, pN11GFPS1sh-A17Amb or pN11GFPS1sh was used as the template DNA for non-canonical amino acid incorporation or control, respectively. Then, the protein synthesis reaction was carried out while 30 μL of the reaction solution was dialyzed overnight at 25° C. against 1 mL of the dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

The upper limit of each PylRS mutant amount that can be added to the reaction solution is the total amount of liquid portion of water (Milli-Q water) corresponding to PylRS. Because the concentration limit of the MmPylRS mutant was 4 mg/mL or less, it was only possible to add it at about maximum 10 μM. Meanwhile, because the concentration limit of the MaPylRS mutant was 20 mg/mL or more, it was possible to add it at 80 μM or higher.

As shown in FIGS. 8 and 9, the above results have demonstrated that use of the highly concentrated MaPylRS mutant caused an increase in the protein yield. FIG. 8 shows the results of incorporation of a non-canonical amino acid TCO*Lys, which is promising for click chemistry reaction. When each PylRS mutant was at a concentration of 10 μM, about 0.25 mg/mL GFPS1 protein was synthesized in the case of MmPylRS and about 0.83 mg/mL GFPS1 protein was synthesized in the case of MaPylRS. Meanwhile, in the case of MaPylRS, the synthesis was possible at the PylRS mutant concentration of 75 μM. Here, at 50 μM, 3 mg/mL protein was successfully synthesized, and the amount was equal to or larger than that of control normal synthesis (WT). This amount was 10 times or higher than the amount synthesized using the MmPylRS mutant. Thus, it has been revealed that use of the highly concentrated MaPylRS mutant permits the TCO*Lys-corporated protein to be prepared highly efficiently.

FIG. 9 shows the results in the case of using pEtZLys or pAzZLys with a lower incorporation efficiency than TCO*Lys. When the PylRS concentration was 10 μM, each case of MmPylRS or MaPylRS yielded a low protein yield. Meanwhile, the MaPylRS mutant caused an increase in the protein yield in a concentration-dependent manner. As the concentration of the PylRS mutant was brought to 75 μM, the protein yield in the case of pEtZLys incorporation was increased to about 0.5 mg/mL and was about 2.5 times the amount at the time of 10 μM addition. In the case of pAzZLys incorporation, the amount was increased about 4.6-fold to about 2 mg/mL and was close to the WT yield during normal synthesis. Thus, it has been revealed that use of the highly concentrated MaPylRS mutant causes the protein yield to increase even in the case of pEtZLys or pAzZLys with a lower incorporation efficiency.

Example 7

7.1 To Incorporate Non-canonical Amino Acid ZLys by Using Each MaPylRS Mutant in Cell-Free Protein Synthesis Process The reaction solution and the dialysis external solution were as provided in the above Table 1. At this time, each PylRS mutant was used as PylRS. Methanomethylophilus alvus tRNA$^{Pyl}$ was used as tRNA$^{Pyl}$. The MaPylRS mutants in FIG. 10 were used as PylRS mutants. The non-canonical amino acid used was N$^ε$-benzyloxycarbonyl-L-lysine (ZLys) (Bachem, Inc.). Here, pN11GFPS1sh-A17Amb or pN11GFPS1sh was used as the template DNA for non-canonical amino acid incorporation or control, respectively. Then, the synthesis reaction was carried out while 30 μL of the reaction solution was dialyzed overnight at 25° C. against 1 mL of the dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1, and was expressed as the percentage with respect to the percentage for control normal synthesis.

FIG. 10 shows the results of checking the yield of ZLys-incorporated protein. Incorporation of a mutation at position 126, 129, 168, or 206 in the amino acid pocket of MaPylRS caused 40% or higher yield with respect to the control. The Y126A/M129A and Y126A/V168C mutations, in particular, caused high yields. The above results have revealed that it is possible to create a mutant fit for ZLys incorporation.

7.2 to Incorporate Non-Canonical Amino Acid mAzZLys by Using Each MaPylRS Mutant in Cell-Free Protein Synthesis Process The reaction solution and the dialysis external solution were as provided in the above Table 1. At this time, each PylRS mutant was used as PylRS. Methanomethylophilus alvus tRNA$^{Pyl}$ was used as tRNA$^{Pyl}$. The MaPylRS mutants in FIG. 11 were used as PylRS mutants. The non-canonical amino acid used was N$^ε$-(m-azidobenzyloxycarbonyl)-L-lysine (mAzZLys) (Sundia/Namiki, Inc.). Here, pN11GFPS1sh-A17Amb or pN11GFPS1sh was used as the template DNA for non-canonical amino acid incorporation or control, respectively. Then, the synthesis reaction was carried out while 30 μL of the reaction solution was dialyzed overnight at 25° C. against 1 mL of the dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1, and was expressed as the percentage with respect to the percentage for control normal synthesis.

FIG. 11 shows the results of checking the yield of mAzZLys-incorporated protein. Incorporation of a mutation at position 126, 129, or 168 in the amino acid pocket of MaPylRS caused at least 65% or higher yield with respect to control. The above results have revealed that it is possible to create a mutant fit for mAzZLys incorporation.

Example 8

8.1 to Prepare Fab Antibody Corporated Non-Canonical Amino Acid TCO*-Lys by Using Each MaPylRS Mutant The reaction solution composition and the dialysis external solution composition in Table 2 below were used to carry out cell-free protein synthesis for incorporating a non-canonical amino acid TCO*Lys, which is promising for click chemistry reaction, into the L-chain of Herceptin Fab antibody.

TABLE 2

| Stock solution | Final concentration | Reaction solution | Dialysis External Solution |
|---|---|---|---|
| LMCPY mixture-PEG-DTT | 37.33% | 1866.5 μL | 18.7 mL |
| 17.5 mg/mL tRNA | 0.175 mg/mL | 50 μL | — |
| 1.6M magnesium acetate | 10 mM | 31.25 μL | 312.5 μL |
| 20 mM amino acid mixture | 1.5 mM | 375 μL | 3.75 mL |
| 3.75 mg/mL creatine kinase | 0.1 mg/mL | 133.3 μL | — |

TABLE 2-continued

| Stock solution | Final concentration | Reaction solution | Dialysis External Solution |
|---|---|---|---|
| 10 mg/mL T7 RNA polymerase | 0.067 mg/mL | 33.3 µL | — |
| Chaperone enhanced S30 extract | 30% | 1500 µL | — |
| S30 buffer | 30% | — | 15 mL |
| Template DNA 1 | 2 µg/mL | 10 µL | — |
| Template DNA 2 | 0.8 mg/mL | 10 µL | — |
| 100 mM GSSG | 5 mM | 250 µL | 2.5 mL |
| 25 mg/mL DsbC | 32 µL | 160 µL | — |
| tRNA$^{Pyl}$ | 6.5-10 µM | | — |
| | | Total 460 µL | |
| PylRS mutant | 6.5-50 µM | | — |
| 1N HCl for pH adjustment | 1/5 volume of TCO*Lys | 20 µL | 200 µL |
| 50 mM TCO*-Lys | 1 mM | 100 µL | 1 mL |
| Milli-Q water | | 0 µL | 8.54 mL |
| Total | | 5 mL | 50 mL |

*Methanosarcina mazei* tRNA$^{Pyl}$ and Methanomethylophilus alvus tRNA$^{Pyl}$ were each used as tRNA$^{Pyl}$. The MmPylRS(Y306A/Y384F/R61K) mutant and the MaPylRS (Y126A/M129L) mutant were each used as a PylRS mutant. The maximum liquid amount of tRNA$^{Pyl}$ and PylRS that was able to be added to this system was 460 µL. Accordingly, the amount of *Methanosarcina mazei* tRNA$^{Pyl}$ or the PylRS mutant added was 6.5 µM equivalent, the amount of Methanomethylophilus alvus tRNA$^{Pyl}$ or the PylRS mutant was 10 µM or 50 µM equivalent, respectively. The template DNA used for Herceptin Fab H-chain was pN11TVGS_Her-H, and the template DNA pN11TVGS_Her-L-S203Amb used for Herceptin Fab L-chain had a codon for non-canonical amino acid incorporation site at a.a. 203. Then, the protein synthesis reaction was carried out while 5 mL of the reaction solution was dialyzed overnight at 25° C. against 50 mL of the dialysis external solution. The post-synthesis reaction solution was subjected to tag-cleavage and purification processing. Click chemistry was performed while a 10-fold equivalent of TAMRA-tetrazine was mixed and reacted at 25° C. for 10 min or 30 min.

As a result, as shown in FIG. 12, the yield of TCO*Lys-incorporated Herceptin Fab dimer per mL of the reaction solution for cell-free protein synthesis was 1.7 mg in the case of using the MaPylRS mutant. This amount was 20 times the amount in the case of using the MmPylRS mutant.

FIGS. 13 and 14 show the results of using click chemistry for linking a fluorescent substrate TAMRA with a TCO*Lys incorporated. TCO*Lys was highly reactive, and the linking reaction was almost completed within 10 min. After the synthesis using the MaPylRS mutant, each L-chain after the click chemistry in the electrophoresis image was shifted to the high-molecular-weight side and exhibited a strong fluorescent intensity. By contrast, after the synthesis using the MmPylRS mutant, the proportion of the L-chain shifted to the high-molecular-weight side was ½ of the amount in the case of the MaPylRS mutant and the fluorescent intensity was about ⅓. The fluorescent intensity per protein amount in the electrophoresis image was 1.5 times higher in the case of the MaPylRS mutant. This, together with FIG. 12, has revealed that it was possible to prepare a TCO*Lys-incorporated Fab antibody in the amount 30 times higher than the amount synthesized using the MaPylRS mutant.

Thus, use of the highly concentrated MaPylRS mutant permits the TCO*Lys-incorporated Fab antibody to be prepared more efficiently than conventional methods. In addition, the incorporation of TCO*Lys allows for highly reactive click chemistry.

Example 9

9.1 to Compare Efficiency of Incorporating Non-Canonical Amino Acid by Using *Methanosarcina mazei*, Methanomethylophilus Alvus, or *Desulfitobacterium hafniense* PylRS in *Escherichia coli* Expression System The non-canonical amino acid (ncAA) used was BocLys or AlocLys (Bachem). The PylRS gene (wild-type) used was MaPylS (Methanomethylophilus alvus PylRS gene), MmPylS (*Methanosarcina mazei* PylRS gene), or DhPylS (*Desulfitobacterium hafniense* PylRSc gene). The tRNA$^{Pyl}$ gene used was MaPylT (Methanomethylophilus alvus tRNA$^{Pyl}$), MmPylT (*Methanosarcina mazei* tRNA$^{Pyl}$), or DhPylT (*Desulfitobacterium hafniense* tRNA$^{Pyl}$). At this time, the PylRS and tRNA$^{Pyl}$ genes from the same archaeon were used in combination. The *Escherichia coli* used was BL21-Gold (DE3). The plasmid used was a pBT5 series (T5/lacO-PylRS, T5/lacO-tRNAPyl). The protein expression plasmid used was pACYC-GST-GFP (amber3) (T7/lacO-3amb-His6-GST-GFP; Ser at the third position from the N-terminus was mutated and corresponded to an amber codon).

A pBT5 series, pACYC-GST-GFP (amber3), was transformed into *Escherichia coli* BL21-Gold (DE3), and the resulting cells were cultured at 25° C. for 24 h in 2 ml or 0.2 ml of 2×YT autoinduction medium containing each non-canonical amino acid (BocLys or AlocLys) at 1 mM. At this time, the PylRS was expressed at a high level by using T5 promoter (SEQ ID NO: 6) in the pBT5 series. Then, 10 µL of the *Escherichia coli* culture liquid was added on a 96-well microplate to and diluted with 0.19 mL of PBS. After that, a SpectraMAX i3 plate reader (Molecular Devices) was used to measure fluorescence at 485/510 nm in terms of absorption at 600 nm to compare the fluorescence levels.

FIG. 15 shows the results. In the graph, -ncAA means conditions without any non-canonical amino acid. When DhPylS was used, no fluorescence was detected. When MmPylS was used, some fluorescence was detected and the incorporation efficiency was 9% in the case of BocLys. By contrast, when MaPylS was used, the highest fluorescence level was exhibited, and the BocLys or AlocLys incorporation efficiency was 57% or 64% respectively. The BocLys incorporation efficiency in the case of using MaPylRS in the PylRS high-expression system was six times higher than that in the case of MmPylRS. The AlocLys incorporation efficiency was 14 times higher than that in the case of MmPylRS. Note that growth of *Escherichia coli* in which MmPylRS was expressed at a high level appeared poor while growth of *Escherichia coli* in which MaPylRS was expressed at a high level did not appear poor.

Example 10

10.1 to Analyze Wild-Type GST-GFP Fusion Protein (3Ser) and Amber Mutant GST-GFP Fusion Protein A wild-type GST-GFP or a GST-GFP (amber3) was expressed in 5-mL broth in the presence of 1 mM BocLys. The bacterial cells were collected and then crushed with a Bugbuster Master Mix reagent (Merck Millipore). The resulting protein was purified through a GST SpinTrap (GE Healthcare), subjected to SDS-PAGE, and then stained with Simplyblue safe stain. A gel piece was excised and digested at 37° C. over day and night with Trypsin/Lys-C Mix (Mass Spec grade (Promega)). The product was purified through a His SpinTrap TALON, eluted with 4% acetonitrile containing 0.1% TFA, and then subjected to MALDI-TOF MS analysis.

FIG. 16 shows the results. Here, 59 mg of the GST-GFP product was obtained using MaPylRS (c.f., 106 mg of the wild-type GST-GFP was obtained), and each amount was proportional to the corresponding fluorescence level. It was verified from MALDI-TOF analysis after trypsin digestion that the third residue of 1-12 peptide (MNXSSHHHHHHR) was assigned to a BocLys (peak 2) and was assigned to a Ser (peak 1) in the wild-type one (peak 3 was due to degradation of BocLys to Lys by acid (TFA) treatment; * was a peak derived from a product with a different starting Met.

Example 11

11.1 Site-Specific Incorporation of Non-Canonical Amino Acid into Protein by Using MaPylRS in *Escherichia coli* Expression System.

The non-canonical amino acid (ncAA) used was BocLys, AlocLys, DBocLys (Bachem), or PocLys (SynChem). The PylRS used was MaPylRS or MmPylRS(R61K/G131E/Y384F) (BocLysRS2). The tRNA$^{Pyl}$ used was Methanomethylophilus alvus or *Methanosarcina mazei* tRNA$^{Pyl}$. At this time, PylRS and tRNA$^{Pyl}$ from the same archaeon were used in combination. The *Escherichia coli* used was BL21-Gold (DE3). The plasmid used was a pBT5 series (T5/lacO-PylRS, T5/lacO-tRNAPyl). The protein expression plasmid used was pACYC-GST-GFP (amber3) (T7/lacO-3amb-His6-GST-GFP; Ser at the third position from the N-terminus was mutated and corresponded to an amber codon).

A pBT5 series, pACYC-GST-GFP (amber3), (pBR322 as a control) was transformed into *Escherichia coli* BL21-Gold (DE3), and the resulting cells were cultured at 25° C. for 24 h in 2 ml or 0.2 ml of 2×YT autoinduction medium containing each non-canonical amino acid at 1 mM. At this time, PylRS was expressed at a high level by using T5 promoter of the pBT5 series. Then, 10 μl of the *Escherichia coli* culture liquid was added on a 96-well microplate to and diluted with 0.19 mL of PBS. After that, a SpectraMAX i3 plate reader was used to measure fluorescence at 485/510 nm in terms of absorption at 600 nm.

FIG. 17 shows the results. In the graph, -ncAA means conditions without any non-canonical amino acid. In a PylRS high-expression system, it was possible to incorporate BocLys, DBocLys, AlocLys, or PocLys in a better efficiency when MaPylRS was used than when MmPylRS (R61K/G131E/Y384F) was used. Note that growth of *Escherichia coli* in which the MmPylRS mutant was expressed at a high level appeared poor while growth of *Escherichia coli* in which MaPylRS was expressed at a high level did not appear poor.

Example 12

12.1 Site-Specific Incorporation of ZLys-Based Non-Canonical Amino Acid into Protein by Using MaPylRS Mutant in *Escherichia coli* Expression System.

The non-canonical amino acid used was ZLys (WATANABE CHEMICAL INDUSTRIES, LTD.), oClZLys, pNO2ZLys (Bachem), pTmdZLys, oAzZLys, mAzZLys, oEtZLys, AmAzZLys, or AzNO2ZLys (Shinsei Chemical Company Ltd.). The MaPylRS mutant used was MaPylRS (Y126A/M129L) or MaPylRS(Y126A/M129L/Y206F). The MmPylRS mutant used was MmPylRS(Y306A/Y384F). The tRNA$^{Pyl}$ used was Methanomethylophilus alvus or

*Methanosarcina mazei* tRNA$^{Pyl}$. At this time, PylRS and tRNAPyl from the same archaeon were used in combination. The *Escherichia coli* used was BL21-Gold (DE3). The plasmid used was a pBT5 series (T5/lacO-PylRS, T5/lacO-tRNAPyl). The protein expression plasmid used was pACYC-GST-GFP (amber3) (T7/lacO-3amb-His6-GST-GFP; Ser at the third position from the N-terminus was mutated and corresponded to an amber codon).

A pBT5 series, pACYC-GST-GFP (amber3), (pBR322 as a control) was transformed into *Escherichia coli* BL21-Gold (DE3), and the resulting cells were cultured at 25° C. for 24 h in 2 ml or 0.2 ml of 2×YT autoinduction medium containing each non-canonical amino acid at 1 mM. At this time, PylRS was expressed at a high level by using T5 promoter of the pBT5 series. Then, 10 μl of the *Escherichia coli* culture liquid was added on a 96-well microplate to and diluted with 0.19 mL of PBS. After that, a SpectraMAX i3 plate reader (Molecular Devices) was used to measure fluorescence at 485/510 nm in terms of absorption at 600 nm to compare the fluorescence levels while the fluorescence level of the wild-type GST-GFPwt was set to 1.

FIG. 18 shows the results. In the graph, -ncAA means conditions without any non-canonical amino acid. In the PylRS high-expression system, every ZLys derivative was successfully incorporated. The MaPylRS(Y126A/M129L) mutant had the highest incorporation efficiency. In particular, the MaPylRS(Y126A/M129L) mutant had an incorporation efficiency (3- to 18-fold) higher than the MmPylRS (Y306A/Y384F) mutant. Note that the growth of *Escherichia coli* in which the MmPylRS mutant was expressed at a high level appeared poor while growth of *Escherichia coli* in which each MaPylRS mutant was expressed at a high level did not appear poor.

Example 13

13.1 to Check PylRS Concentration Dependence in Wheat Germ-Based, Cell-Free Protein Synthesis Process How effective was making MaPylRS highly concentrated in a eukaryotic protein synthesis system was checked. For this purpose, a Premium PLUS Expression Kit (CellFree Sciences Co., Ltd.) for a wheat germ-based, cell-free protein synthesis process was used to test incorporation of TCO*Lys.

*Methanosarcina mazei* tRNA$^{Pyl}$ or Methanomethylophilus alvus tRNA$^{Pyl}$ was used as tRNA$^{Pyl}$. MaPylRS(Y306A/Y384F/R61K) or MaPylRS(Y126A/M129L) was used as the PylRS mutant. Each mutant was added in a range from 10 μM to 50 μM to the reaction solution. TCO*Lys at the final concentration of 1 mM was used as the non-canonical amino acid. The template DNA used for non-canonical amino acid incorporation was pEU-E01-GFPS1sh-A17Amb. The synthesis reaction was carried out at 15° C. for 20 h by a protocol in which 206 μL of substrate solution was overlaid on about 20 μL of the translation reaction solution. After the synthesis, 20 μL of the mixture was diluted about 10-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As shown in FIG. 19, the results have demonstrated that 10 μM or higher concentration of PylRS caused the protein yield to increase, and the amount in the case of 50 μM PylRS was increased by about 7.2-fold. This has demonstrated the effectiveness of making MaPylRS highly concentrated in a eukaryotic protein synthesis system.

Example 14

14.1 to Check PylRS Concentration Dependence in Human-Based, Cell-Free Protein Synthesis Process How effective was making MaPylRS highly concentrated in a human (particularly useful among eukaryotes) cell-based protein synthesis system was checked. For this purpose, a Human Cell-Free Protein Expression Maxi System (TAKARA) for a human cell-based, cell-free protein synthesis process was used to test incorporation of TCO*Lys.

Methanomethylophilus alvus tRNA$^{Pyl}$ was used as tRNA$^{Pyl}$. MaPylRS(Y126A/M129L) was used as a PylRS mutant. The mutant was added in a range from 10 μM to 50 μM to the reaction solution. TCO*Lys at the final concentration of 1 mM was used as a non-canonical amino acid. The template DNA used for non-canonical amino acid incorporation was pN11GFPS1sh-A17Amb. The synthesis reaction was carried out at 32° C. for 20 h by a protocol in which 30 μL of reaction solution was dialyzed against 350 μL of the external solution. After the synthesis, 20 μL of the mixture was diluted about 10-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As shown in FIG. 20, the results have demonstrated that as the MaPylRS concentration was increased, the protein yield became larger, and the amount in the case of 50 μM MaPylRS was increased by about 1.8-fold. This has demonstrated the effectiveness of making MaPylRS highly concentrated in a human cell-based, cell-free protein synthesis system. Alternatively, the effectiveness was verified in a cell-free protein synthesis process, indicating the effectiveness in a human cell-based expression system using the same transcription and translation system.

Example 15

15.1 Test for Checking AcLys Incorporation

Methanomethylophilus alvus PylRS was used to check incorporation of a non-canonical amino acid N$^\varepsilon$-acetyl-L-lysine (AcLys).

The reaction solution and the dialysis external solution were as provided in the above Table 1. At this time, Methanomethylophilus alvus tRNA$^{Pyl}$ was used as tRNA$^{Pyl}$; MaPylRS(121V/125I/126F/129A/168F), designated as AcLysRS3, or MaPylRS(121V/125I/126F/129A/168F/227I/228P), designated as AcLysRS3-IP, was used as a PylRS mutant; they were each added at 10 μM to the reaction solution; and AcLys was used at the final concentration of 1 mM. Here, pN11GFPS1sh-A17Amb or pN11GFPS1sh was used as the template DNA for non-canonical amino acid incorporation or control, respectively. Then, the synthesis reaction was carried out while 30 μL of the reaction solution was dialyzed overnight at 25° C. against 1 mL of the dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As shown in FIG. 21, the results have demonstrated that each MaPylRS mutant was used to successfully incorporate AcLys.

Example 16

16.1 Test for Checking Incorporation of Phe Derivative

Methanomethylophilus alvus PylRS was used to check incorporation of 3-iodo-L-phenylalanine (IPhe), a phenylalanine (Phe) derivative.

The reaction solution and the dialysis external solution were as provided in the above Table 1. At this time, Methanomethylophilus alvus tRNA$^{Pyl}$ was used as tRNA$^{Pyl}$; MaPylRS(166A/168A) or MaPylRS(166A/168A/227I/228P) was used as a MaPylRS mutant; they were each added at 10 μM to the reaction solution; and IPhe was used at the final concentration of 1 mM. Here, pN11GFPS1sh-A17Amb or pN11GFPS1sh was used as the template DNA for non-canonical amino acid incorporation or control, respectively. Meanwhile, since there is a report showing that a mutant for a Phe derivative caused incorporation of phenylalanine itself, IPhe-free synthesis was also checked. Then, the synthesis reaction was carried out while 30 μL of the reaction solution was dialyzed overnight at 25° C. against 1 mL of the dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As shown in FIG. 22, the results have demonstrated that each MaPylRS mutant was used to successfully incorporate IPhe. This has demonstrated that each MaPylRS mutant is effective for the Phe derivative.

Example 17

17.1 Test for Checking Incorporation of Tyr Derivative

Methanomethylophilus alvus PylRS was used to check incorporation of o-propargyl-L-tyrosine (oPgTyr), a tyrosine (Tyr) derivative.

The reaction solution and the dialysis external solution were as provided in the above Table 1. At this time, Methanomethylophilus alvus tRNA$^{Pyl}$ was used as tRNA$^{Pyl}$; MaPylRS(166A/168A) was used as a PylRS mutant; they were each added at 10 μM to the reaction solution; and oPgTyr was used at the final concentration of 1 mM. Here, pN11GFPS1sh-A17Amb or pN11GFPS1sh was used as the template DNA for non-canonical amino acid incorporation or control, respectively. Then, the synthesis reaction was carried out while 30 μL of the reaction solution was dialyzed overnight at 25° C. against 1 mL of the dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As shown in FIG. 23, the results have demonstrated that the Methanomethylophilus alvus PylRS mutant was used to successfully incorporate oPgTyr. This has demonstrated that the Methanomethylophilus alvus PylRS mutant is effective for the Tyr derivative.

Example 18

18.1 Test for Checking PylRS Derived from Methanogenic Archaeon ISO4-G1

PylRS of methanogenic archaeon ISO4-G1 (G1PylRS) was evaluated. The DNA sequence of ISO4-G1 PylRS, which was used for synthesis, is (SEQ ID NO: 7)
ATGGTAGTCAAATTCACTGACAGCCAAATCCAACATCTGATGGAGTATGG

TGATAATGATTGGAGCGAGGCAGAATTTGAGGACGCTGCTGCTCGTGATA

AAGAGTTTTCAAGCCAATTCTCCAAGTTGAAGAGTGCGAACGACAAAGGA

TTGAAAGACGTCATTGCGAACCCGCGTAATGACCTGACCGACCTTGAAAA

TAAGATTCGTGAGAAACTTGCTGCACGCGGTTTCATCGAAGTGCATACGC

CTATTTTTGTATCTAAGAGTGCATTAGCCAAGATGACAATCACCGAGGAT

CATCCTTTATTCAAGCAGGTCTTCTGGATCGACGACAAACGTGCCTTGCG

TCCAATGCATGCGATGAATCTTTATAAGGTAATGCGCGAGTTGCGCGATC

ACACAAAGGGACCAGTCAAGATCTTCGAGATTGGCTCGTGCTTCCGCAAG

GAAAGCAAGTCATCGACGCATTTGGAAGAATTCACTATGCTGAACTTAGT

TGAGATGGGACCCGATGGCGACCCTATGGAGCACCTTAAGATGTATATTG

GAGACATCATGGACGCGGTTGGTGTAGAATACACCACCTCACGTGAGGAG

TCTGATGTGTACGTAGAGACACTTGACGTGGAGATCAATGGAACTGAAGT

TGCGTCAGGAGCAGTAGGTCCTCATAAGCTTGACCCTGCCCACGATGTGC

ATGAACCCTGGGCAGGAATCGGATTCGGACTGGAGCGTCTGTTGATGCTT

AAGAACGGTAAATCGAATGCTCGTAAGACAGGCAAAAGTATCACCTATTT

GAATGGTTACAAATTGGAT;

and the DNA sequence for the tRNAPyl is (SEQ ID NO: 8)
GGAGGGCGCTCCGGCGAGCAAACGGGTCTCTAAAACCTGTAAGCGGGGTT

CGACCCCCCGGCCTTTCGCCA.

The RNA sequence of ISO4-G1 tRNAPyl is (SEQ ID NO: 9)
GGAGGGCGCUCCGGCGAGCAAACGGGUCUCUAAAACCUGUAAGCGGGGUU

CGACCCCCCGGCCUUUCGCCA.

ISO4-G1 tRNAPyl and PylRS were each added at 10 μM to and BocLys or PocLys was added at 1 mM to the reaction solution for an *Escherichia coli* cell-free protein synthesis system. Here, pN11GFPS1sh-A17Amb or pN11GFPS1sh was used as the template DNA for non-canonical amino acid incorporation or control, respectively. Then, the synthesis reaction was carried out while 30 μL of the reaction solution was dialyzed overnight at 25° C. against 1 mL of the dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As shown in FIG. 24, the results have demonstrated that the ISO4-G1 PylRS was used to synthesize proteins by incorporating non-canonical amino acids efficiently. In addition, FIG. 25 shows the results of comparing the yield to that in the case of *Methanosarcina mazei* or Methanomethylophilus alvus PylRS as a control. The results have demonstrated that the ISO4-G1 PylRS was effective. The G1PylRS exerted such an excellent incorporation efficiency in the cell-free protein synthesis system, which is a surprising result.

Example 19

19.1 Test for Checking PylRS Mutants Derived from Methanogenic Archaeon ISO4-G1

Each of the methanogenic archaeon ISO4-G1 PylRS mutants, designated as G1PylRS(Y125A/M128A) and G1PylRS(Y125A/M128L), was tested for incorporation of a non-canonical amino acid. The non-canonical amino acid checked was ZLys, TCO*Lys, BCNLys, pETZLys, or pAz-ZLys. ISO4-G1 tRNA$^{Pyl}$ and the respective PylRS mutant were each added at 10 μM to and the respective non-canonical amino acid was added at 1 mM to the reaction solution for an *Escherichia coli* cell-free protein synthesis system. Here, pN11GFPS1sh-A17Amb or pN11GFPS1sh was used as the template DNA for non-canonical amino acid incorporation or control, respectively. Then, the synthesis reaction was carried out while 30 μL of the reaction solution was dialyzed overnight at 25° C. against 1 mL of the dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As shown in FIG. 26, the results have demonstrated that each ISO4-G1 PylRS mutant was used to synthesize proteins by incorporating non-canonical amino acids efficiently. In addition, FIG. 27 shows the results of comparing the yield to that in the case of the *Methanosarcina mazei* PylRS mutant as a control. The results have demonstrated that each ISO4-G1 PylRS mutant was effective.

Example 20

20.1 Test for Checking Concentration Dependence in Cell-Free Protein Synthesis Process Using Methanogenic Archaeon ISO4-G1

Like Methanomethylophilus alvus PylRS, the methanogenic archaeon ISO4-G1 PylRS or PylRS mutant has a high concentration limit, and can thus be used at a high concentration. Here, the concentration dependence when the methanogenic archaeon ISO4-G1 PylRS mutant, G1PylRS (Y125A/M128L) was used was checked in the case of pEtZLys, for which the control yield did not reach 100% in FIG. 27.

The reaction solution and the dialysis external solution were as provided in Table 1.

The methanogenic archaeon ISO4-G1 PylRS(Y125A/M128L) was used in a range from 10 μM to 75 μM. ISO4-G1 tRNA$^{Pyl}$ and a non-canonical amino acid pEtZLys were added at 10 μM and 1 mM, respectively. The template DNA used was pN11GFPS1sh-A17Amb. The synthesis reaction was carried out while 30 μL of the reaction solution was dialyzed overnight at 25° C. against 1 mL of dialysis external solution. After the synthesis, 1-μL equivalent of the reaction solution was diluted about 200-fold, and the fluorescence level was measured while the excitation was at 485 nm and the emission was monitored at 535 nm. The synthesized GFPS1 protein amount was quantified with reference to the fluorescence level of 1 mg/mL standard GFPS1.

As shown in FIG. 28, the results have demonstrated that 10 μM or higher concentration caused the protein yield to increase, and the amount in the case of 75 μM PylRS was increased by about 6.8-fold. The results have demonstrated that it was effective to use the ISO4-G1 PylRS mutant at a high concentration.

Example 21

21.1 Incorporation of mAzZLys into Protein in Mammalian Cell.

A Methanomethylophilus alvus PylRS mutant, MaPylRS (Y126A/M129L/H227I/Y228P), and Methanomethylophilus alvus tRNA$^{Pyl}$ or a methanogenic archaeon ISO4-G1 PylRS mutant, G1PylRS(Y125A/M128L), and ISO4-G1 tRNA$^{Pyl}$ were expressed at a high level in a mammalian cell (HEK293c18 cell). For this purpose, a system (disclosed in Mukai, et al., Biochem. Biophys. Res. Commun. Vol. 371, pp. 818-822 (2008)) was used. For a protein of interest, a mutated gene in which an amber codon (T137 or N157) had been incorporated in a coding region of the gene and its expression system were used.

FIG. 29 shows the results. In any of the cases, it was found that non-canonical amino acid was incorporated into the protein. In this experiment, 1 copy of each tRNA gene was used instead of 9 copy. Nevertheless, the non-canonical amino acid-incorporated proteins were able to be synthesized. The above experiment has demonstrated that the system for expressing, at a high level, the Methanomethylophilus alvus PylRS mutant, MaPylRS(Y126A/M129L/H227I/Y228P), or the methanogenic archaeon ISO4-G1 PylRS mutant, G1PylRS(Y125A/M128L), was effective for site-specific incorporation of mAzZLys into a desired site in a mammalian cell.

Hereinabove, the invention has been described based on the Examples. The Examples are just examples. It should be understood by those skilled in the art that various modifications are allowed and such modified embodiments are also within the scope of the invention.

---

The invention claimed is:

1. A method for producing a polypeptide containing a non-canonical amino acid, comprising:

a step of contacting a pyrrolysyl-tRNA synthetase (PylRS) with the non-canonical amino acid; wherein:

the contact is performed in a non-canonical amino acid incorporation system containing the PylRS, the non-canonical amino acid incorporation system comprises a reaction solution for a cell-free protein synthesis system, and the reaction solution comprises 25-μm or higher PylRS, the PylRS is a wild-type or mutant PylRS, and the wild-type or mutant PylRS has an amino acid sequence with at least 90% identity to the amino acid sequence set forth in SEQ ID NO: 5 and has pyrrolysyl-tRNA synthetase activity, and the non-canonical amino acid is a lysine derivative, tyrosine derivative, phenylalanine derivative, tryptophan derivative, arginine derivative, methionine derivative, leucine derivative, histidine derivative, proline derivative, cysteine derivative, threonine derivative, serine derivative, alanine derivative, isoleucine derivative, valine derivative, glutamine derivative, glutamic acid derivative, asparagine derivative, aspartic acid derivative, glycine derivative, selenocysteine derivative, pyrrolysine derivative, kynurenine derivative, ornithine derivative, citrulline derivative, canavanine derivative, or diaminopimelic acid, or an α-hydroxy acid derivative thereof.

2. The production method according to claim 1, wherein the contact incorporates the non-canonical amino acid into the polypeptide with efficiency at least 1.5 times than efficiency when MmPylRS is used as the PylRS.

3. The production method according to claim 1, wherein the reaction solution comprises a polynucleotide encoding a gene having a stop codon at a position different from a naturally occurring position.

4. The production method according to claim 1, further comprising a step of mixing a solution containing the wild-type or mutant PylRS of at least 5 mg/mL and the non-canonical amino acid to prepare a mixed solution.

5. The production method according to claim 1, wherein the wild-type or mutant PylRS is PylRS from Methanomethylophilus alvus (MaPylRS).

6. The production method according to claim 1, wherein the wild-type or mutant PylRS has pyrrolysyl-tRNA synthetase activity, and has (i) the amino acid sequence set forth in SEQ ID NO: 5, or (ii) an amino acid sequence having a mutation at position 96, 120, 121, 122, 125, 126, 128, 129, 164, 166, 168, 170, 203, 204, 205, 206, 207, 221, 223, 227, 228, 233, 235, 239, 241, or 243 of the amino acid sequence set forth in SEQ ID NO: 5.

7. The production method according to claim 1, wherein the polypeptide containing a non-canonical amino acid is bonded to a drug.

8. The production method according to claim 1, wherein the wild-type or mutant PylRS has an amino acid sequence with at least 95% identity to the amino acid sequence set forth in SEQ ID NO: 5 and has pyrrolysyl-tRNA synthetase activity.

* * * * *

SEQUENCE LISTING

<160> NUMBER OF SEQ ID NOS: 12

<210> SEQ ID NO 1
<211> LENGTH: 558
<212> TYPE: PRT
<213> ORGANISM: Methanosarcina mazeii

<400> SEQUENCE: 1

```
Met His His His His His His Gly Ser Asp Ser Glu Val Asn Gln Glu
1               5                   10                  15

Ala Lys Pro Glu Val Lys Pro Glu Val Lys Pro Glu Thr His Ile Asn
                20                  25                  30

Leu Lys Val Ser Asp Gly Ser Ser Glu Ile Phe Phe Lys Ile Lys Lys
            35                  40                  45

Thr Thr Pro Leu Arg Arg Leu Met Glu Ala Phe Ala Lys Arg Gln Gly
        50                  55                  60

Lys Glu Met Asp Ser Leu Arg Phe Leu Tyr Asp Gly Ile Arg Ile Gln
65                  70                  75                  80

Ala Asp Gln Thr Pro Glu Asp Leu Asp Met Glu Asp Asn Asp Ile Ile
                85                  90                  95

Glu Ala His Arg Glu Gln Ile Gly Gly Asp Lys Lys Pro Leu Asn Thr
            100                 105                 110

Leu Ile Ser Ala Thr Gly Leu Trp Met Ser Arg Thr Gly Thr Ile His
            115                 120                 125

Lys Ile Lys His His Glu Val Ser Arg Ser Lys Ile Tyr Ile Glu Met
        130                 135                 140

Ala Cys Gly Asp His Leu Val Val Asn Asn Ser Arg Ser Ser Arg Thr
145                 150                 155                 160

Ala Arg Ala Leu Arg His His Lys Tyr Arg Lys Thr Cys Lys Arg Cys
                165                 170                 175

Arg Val Ser Asp Glu Asp Leu Asn Lys Phe Leu Thr Lys Ala Asn Glu
            180                 185                 190

Asp Gln Thr Ser Val Lys Val Lys Val Val Ser Ala Pro Thr Arg Thr
            195                 200                 205

Lys Lys Ala Met Pro Lys Ser Val Ala Arg Ala Pro Lys Pro Leu Glu
        210                 215                 220
```

```
Asn Thr Glu Ala Ala Gln Ala Gln Pro Ser Gly Ser Lys Phe Ser Pro
225                 230                 235                 240

Ala Ile Pro Val Ser Thr Gln Glu Ser Val Ser Val Pro Ala Ser Val
                245                 250                 255

Ser Thr Ser Ile Ser Ser Ile Ser Thr Gly Ala Thr Ala Ser Ala Leu
                260                 265                 270

Val Lys Gly Asn Thr Asn Pro Ile Thr Ser Met Ser Ala Pro Val Gln
                275                 280                 285

Ala Ser Ala Pro Ala Leu Thr Lys Ser Gln Thr Asp Arg Leu Glu Val
        290                 295                 300

Leu Leu Asn Pro Lys Asp Glu Ile Ser Leu Asn Ser Gly Lys Pro Phe
305                 310                 315                 320

Arg Glu Leu Glu Ser Glu Leu Leu Ser Arg Arg Lys Lys Asp Leu Gln
                325                 330                 335

Gln Ile Tyr Ala Glu Glu Arg Glu Asn Tyr Leu Gly Lys Leu Glu Arg
                340                 345                 350

Glu Ile Thr Arg Phe Phe Val Asp Arg Gly Phe Leu Glu Ile Lys Ser
                355                 360                 365

Pro Ile Leu Ile Pro Leu Glu Tyr Ile Glu Arg Met Gly Ile Asp Asn
        370                 375                 380

Asp Thr Glu Leu Ser Lys Gln Ile Phe Arg Val Asp Lys Asn Phe Cys
385                 390                 395                 400

Leu Arg Pro Met Leu Ala Pro Asn Leu Tyr Asn Tyr Leu Arg Lys Leu
                405                 410                 415

Asp Arg Ala Leu Pro Asp Pro Ile Lys Ile Phe Glu Ile Gly Pro Cys
                420                 425                 430

Tyr Arg Lys Glu Ser Asp Gly Lys Glu His Leu Glu Glu Phe Thr Met
                435                 440                 445

Leu Asn Phe Cys Gln Met Gly Ser Gly Cys Thr Arg Glu Asn Leu Glu
        450                 455                 460

Ser Ile Ile Thr Asp Phe Leu Asn His Leu Gly Ile Asp Phe Lys Ile
465                 470                 475                 480

Val Gly Asp Ser Cys Met Val Tyr Gly Asp Thr Leu Asp Val Met His
                485                 490                 495

Gly Asp Leu Glu Leu Ser Ser Ala Val Val Gly Pro Ile Pro Leu Asp
                500                 505                 510

Arg Glu Trp Gly Ile Asp Lys Pro Trp Ile Gly Ala Gly Phe Gly Leu
                515                 520                 525

Glu Arg Leu Leu Lys Val Lys His Asp Phe Lys Asn Ile Lys Arg Ala
        530                 535                 540

Ala Arg Ser Gly Ser Tyr Tyr Asn Gly Ile Ser Thr Asn Leu
545                 550                 555
```

<210> SEQ ID NO 2
<211> LENGTH: 828
<212> TYPE: DNA
<213> ORGANISM: Methanomethylophilus alvus

<400> SEQUENCE: 2

```
atgacggtca agtacaccga tgctcaaatt caacgtcttc gcgaatatgg aaacggaacc        60
tacgaacaaa aggttttcga ggacttagca tctcgtgacg cggctttcag taaagagatg       120
agcgtggcgt caactgacaa tgaaaaaaag attaaaggga tgattgcaaa tccatcacgt       180
catggtttaa cgcagttaat gaatgatatt gcagacgcat tagtggcaga gggctttatt       240
```

```
gaagtccgta cgccgatttt catctccaaa gatgctttgg cacgtatgac tatcaccgaa      300
gacaagcccc tgtttaagca agttttctgg atcgacgaaa agcgtgcact tcgccctatg      360
ttggcaccaa acctgtactc cgtaatgcgc gacttacgcg atcacaccga cggacccgtg      420
aagattttcg aaatgggatc atgttttcgc aaggaatcac attcaggat gcatctggag       480 gaattcacca tgttgaactt agttgatatg ggaccgcgcg cgatgccac agaagtatta       540 aaaaactaca tcagtgtcgt aatgaaggct gctggtttgc ctgattatga tttagtacaa      600
gaagaaagtg atgtatacaa agaaacaatt gatgtggaaa tcaacgggca agaagtatgc      660
agtgccgcag tggggccgca ttacctggat gcggcccatg acgtgcatga gccttggtct      720
ggtgctggct tcgggttgga gcgtcttta acgattcgtg agaaatactc aacggtcaag       780
aaaggcggcg cttccatcag ttacttgaac ggcgccaaga ttaattaa               828

<210> SEQ ID NO 3
<211> LENGTH: 71
<212> TYPE: RNA
<213> ORGANISM: Methanomethylophilus alvus

<400> SEQUENCE: 3
gggggacggu ccggcgacca gcgggucucu aaaaccuagc cagcgggguu cgacgccccg        60
gucucucgcc a                                                            71

<210> SEQ ID NO 4
<211> LENGTH: 454
<212> TYPE: PRT
<213> ORGANISM: Methanosarcina mazeii

<400> SEQUENCE: 4

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205
```

-continued

```
Ser Leu Asn Ser Gly Lys Pro Phe Arg Glu Leu Glu Ser Glu Leu Leu
    210             215                 220

Ser Arg Arg Lys Lys Asp Leu Gln Gln Ile Tyr Ala Glu Glu Arg Glu
225             230                 235                 240

Asn Tyr Leu Gly Lys Leu Glu Arg Glu Ile Thr Arg Phe Phe Val Asp
            245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
    275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305             310                 315                 320

Lys Ile Phe Glu Ile Gly Pro Cys Tyr Arg Lys Glu Ser Asp Gly Lys
            325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
            355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385             390                 395                 400

Val Val Gly Pro Ile Pro Leu Asp Arg Glu Trp Gly Ile Asp Lys Pro
            405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Gly Ser Tyr Tyr Asn
            435                 440                 445

Gly Ile Ser Thr Asn Leu
    450
```

```
<210> SEQ ID NO 5
<211> LENGTH: 275
<212> TYPE: PRT
<213> ORGANISM: Methanomethylophilus alvus

<400> SEQUENCE: 5
```

```
Met Thr Val Lys Tyr Thr Asp Ala Gln Ile Gln Arg Leu Arg Glu Tyr
1               5                   10                  15

Gly Asn Gly Thr Tyr Glu Gln Lys Val Phe Glu Asp Leu Ala Ser Arg
            20                  25                  30

Asp Ala Ala Phe Ser Lys Glu Met Ser Val Ala Ser Thr Asp Asn Glu
        35                  40                  45

Lys Lys Ile Lys Gly Met Ile Ala Asn Pro Ser Arg His Gly Leu Thr
    50                  55                  60

Gln Leu Met Asn Asp Ile Ala Asp Ala Leu Val Ala Glu Gly Phe Ile
65              70                  75                  80

Glu Val Arg Thr Pro Ile Phe Ile Ser Lys Asp Ala Leu Ala Arg Met
            85                  90                  95

Thr Ile Thr Glu Asp Lys Pro Leu Phe Lys Gln Val Phe Trp Ile Asp
            100                 105                 110

Glu Lys Arg Ala Leu Arg Pro Met Leu Ala Pro Asn Leu Tyr Ser Val
            115                 120                 125
```

-continued

```
Met Arg Asp Leu Arg Asp His Thr Asp Gly Pro Val Lys Ile Phe Glu
    130                 135                 140

Met Gly Ser Cys Phe Arg Lys Glu Ser His Ser Gly Met His Leu Glu
145                 150                 155                 160

Glu Phe Thr Met Leu Asn Leu Val Asp Met Gly Pro Arg Gly Asp Ala
                165                 170                 175

Thr Glu Val Leu Lys Asn Tyr Ile Ser Val Val Met Lys Ala Ala Gly
            180                 185                 190

Leu Pro Asp Tyr Asp Leu Val Gln Glu Glu Ser Asp Val Tyr Lys Glu
        195                 200                 205

Thr Ile Asp Val Glu Ile Asn Gly Gln Glu Val Cys Ser Ala Ala Val
    210                 215                 220

Gly Pro His Tyr Leu Asp Ala Ala His Asp Val His Glu Pro Trp Ser
225                 230                 235                 240

Gly Ala Gly Phe Gly Leu Glu Arg Leu Leu Thr Ile Arg Glu Lys Tyr
                245                 250                 255

Ser Thr Val Lys Lys Gly Gly Ala Ser Ile Ser Tyr Leu Asn Gly Ala
            260                 265                 270

Lys Ile Asn
        275
```

```
<210> SEQ ID NO 6
<211> LENGTH: 99
<212> TYPE: DNA
<213> ORGANISM: Bacteriophage T5

<400> SEQUENCE: 6
aaatcataaa aaatttattt gctttgtgag cggataacaa ttataataga ttcaattgtg      60
agcggataac aatttcacac agaattcatt aaagaggag                            99

<210> SEQ ID NO 7
<211> LENGTH: 819
<212> TYPE: DNA
<213> ORGANISM: Methanogenic archaeon ISO4-G1

<400> SEQUENCE: 7
atggtagtca aattcactga cagccaaatc caacatctga tggagtatgg tgataatgat      60
tggagcgagg cagaatttga ggacgctgct gctcgtgata aagagttttc aagccaattc     120
tccaagttga agagtgcgaa cgacaaagga ttgaaagacg tcattgcgaa cccgcgtaat     180
gacctgaccg accttgaaaa taagattcgt gagaaacttg ctgcacgcgg tttcatcgaa     240
gtgcatacgc ctatttttgt atctaagagt gcattagcca agatgacaat caccgaggat     300
catcctttat tcaagcaggt cttctggatc gacgacaaac gtgccttgcg tccaatgcat     360
gcgatgaatc tttataaggt aatgcgcgag ttgcgcgatc acacaaaggg accagtcaag     420
atcttcgaga ttggctcgtg cttccgcaag gaaagcaagt catcgacgca tttggaagaa     480
ttcactatgc tgaacttagt tgagatggga cccgatggcg accctatgga gcaccttaag     540
atgtatattg agacatcat ggacgcggtt ggtgtagaat acaccaccte acgtgaggag     600 tctgatgtgt acgtagagac acttgacgtg gagatcaatg gaactgaagt tgcgtcagga     660
gcagtaggtc ctcataagct tgaccctgcc cacgatgtgc atgaaccctg ggcaggaatc     720
ggattcggac tggagcgtct gttgatgctt aagaacggta atcgaatgc tcgtaagaca     780 ggcaaaagta tcacctattt gaatggttac aaattggat                           819
```

<210> SEQ ID NO 8
<211> LENGTH: 71
<212> TYPE: DNA
<213> ORGANISM: Methanogenic archaeon ISO4-G1

<400> SEQUENCE: 8
ggagggcgct ccggcgagca acgggtctc taaaacctgt aagcggggtt cgacccccg          60 gcctttcgcc a                                                             71

<210> SEQ ID NO 9
<211> LENGTH: 71
<212> TYPE: RNA
<213> ORGANISM: Methanogenic archaeon ISO4-G1

<400> SEQUENCE: 9
ggagggcgcu ccggcgagca acgggucuc uaaaaccugu aagcgggguu cgacccccg          60 gccuuucgcc a                                                             71

<210> SEQ ID NO 10
<211> LENGTH: 273
<212> TYPE: PRT
<213> ORGANISM: Methanogenic archaeon ISO4-G1

<400> SEQUENCE: 10

Met Val Val Lys Phe Thr Asp Ser Gln Ile Gln His Leu Met Glu Tyr
1               5                   10                  15

Gly Asp Asn Asp Trp Ser Glu Ala Glu Phe Glu Asp Ala Ala Ala Arg
                20                  25                  30

Asp Lys Glu Phe Ser Ser Gln Phe Ser Lys Leu Lys Ser Ala Asn Asp
            35                  40                  45

Lys Gly Leu Lys Asp Val Ile Ala Asn Pro Arg Asn Asp Leu Thr Asp
        50                  55                  60

Leu Glu Asn Lys Ile Arg Glu Lys Leu Ala Ala Arg Gly Phe Ile Glu
65                  70                  75                  80

Val His Thr Pro Ile Phe Val Ser Lys Ser Ala Leu Ala Lys Met Thr
                85                  90                  95

Ile Thr Glu Asp His Pro Leu Phe Lys Gln Val Phe Trp Ile Asp Asp
            100                 105                 110

Lys Arg Ala Leu Arg Pro Met His Ala Met Asn Leu Tyr Lys Val Met
        115                 120                 125

Arg Glu Leu Arg Asp His Thr Lys Gly Pro Val Lys Ile Phe Glu Ile
        130                 135                 140

Gly Ser Cys Phe Arg Lys Glu Ser Lys Ser Ser Thr His Leu Glu Glu
145                 150                 155                 160

Phe Thr Met Leu Asn Leu Val Glu Met Gly Pro Asp Gly Asp Pro Met
                165                 170                 175

Glu His Leu Lys Met Tyr Ile Gly Asp Ile Met Asp Ala Val Gly Val
            180                 185                 190

Glu Tyr Thr Thr Ser Arg Glu Glu Ser Asp Val Tyr Val Glu Thr Leu
            195                 200                 205

Asp Val Glu Ile Asn Gly Thr Glu Val Ala Ser Gly Ala Val Gly Pro
        210                 215                 220

His Lys Leu Asp Pro Ala His Asp Val His Glu Pro Trp Ala Gly Ile
225                 230                 235                 240

Gly Phe Gly Leu Glu Arg Leu Leu Met Leu Lys Asn Gly Lys Ser Asn
                245                 250                 255

```
Ala Arg Lys Thr Gly Lys Ser Ile Thr Tyr Leu Asn Gly Tyr Lys Leu
        260             265             270

Asp

<210> SEQ ID NO 11
<211> LENGTH: 419
<212> TYPE: PRT
<213> ORGANISM: Methanosarcina barkeri

<400> SEQUENCE: 11

Met Asp Lys Lys Pro Leu Asp Val Leu Ile Ser Ala Thr Gly Leu Trp
1               5               10              15

Met Ser Arg Thr Gly Thr Leu His Lys Ile Lys His His Glu Val Ser
                20              25              30

Arg Ser Lys Ile Tyr Ile Glu Met Ala Cys Gly Asp His Leu Val Val
            35              40              45

Asn Asn Ser Arg Ser Cys Arg Thr Ala Arg Ala Phe Arg His His Lys
        50              55              60

Tyr Arg Lys Thr Cys Lys Arg Cys Arg Val Ser Asp Glu Asp Ile Asn
65              70              75              80

Asn Phe Leu Thr Arg Ser Thr Glu Ser Lys Asn Ser Val Lys Val Arg
                85              90              95

Val Val Ser Ala Pro Lys Val Lys Lys Ala Met Pro Lys Ser Val Ser
            100             105             110

Arg Ala Pro Lys Pro Leu Glu Asn Ser Val Ser Ala Lys Ala Ser Thr
            115             120             125

Asn Thr Ser Arg Ser Val Pro Ser Pro Ala Lys Ser Thr Pro Asn Ser
        130             135             140

Ser Val Pro Ala Ser Ala Pro Ala Pro Ser Leu Thr Arg Ser Gln Leu
145             150             155             160

Asp Arg Val Glu Ala Leu Leu Ser Pro Glu Asp Lys Ile Ser Leu Asn
                165             170             175

Met Ala Lys Pro Phe Arg Glu Leu Glu Pro Glu Leu Val Thr Arg Arg
                180             185             190

Lys Asn Asp Phe Gln Arg Leu Tyr Thr Asn Asp Arg Glu Asp Tyr Leu
            195             200             205

Gly Lys Leu Glu Arg Asp Ile Thr Lys Phe Phe Val Asp Arg Gly Phe
        210             215             220

Leu Glu Ile Lys Ser Pro Ile Leu Ile Pro Ala Glu Tyr Val Glu Arg
225             230             235             240

Met Gly Ile Asn Asn Asp Thr Glu Leu Ser Lys Gln Ile Phe Arg Val
                245             250             255

Asp Lys Asn Leu Cys Leu Arg Pro Met Leu Ala Pro Thr Leu Tyr Asn
            260             265             270

Tyr Leu Arg Lys Leu Asp Arg Ile Leu Pro Gly Pro Ile Lys Ile Phe
            275             280             285

Glu Val Gly Pro Cys Tyr Arg Lys Glu Ser Asp Gly Lys Glu His Leu
        290             295             300

Glu Glu Phe Thr Met Val Asn Phe Cys Gln Met Gly Ser Gly Cys Thr
305             310             315             320

Arg Glu Asn Leu Glu Ala Leu Ile Lys Glu Phe Leu Asp Tyr Leu Glu
                325             330             335

Ile Asp Phe Glu Ile Val Gly Asp Ser Cys Met Val Tyr Gly Asp Thr
                340             345             350
```

-continued

```
Leu Asp Ile Met His Gly Asp Leu Glu Leu Ser Ser Ala Val Val Gly
        355                 360                 365

Pro Val Pro Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu

<210> SEQ ID NO 12
<211> LENGTH: 279
<212> TYPE: PRT
<213> ORGANISM: Desulfitobacterium hafniense

<400> SEQUENCE: 12

Met Ser Ser Ser Trp Thr Lys Val Gln Tyr Gln Arg Leu Lys Glu Leu
1               5                   10                  15

Asn Ala Ser Gly Glu Gln Leu Glu Met Gly Phe Ser Asp Ala Leu Ser
                20                  25                  30

Arg Asp Arg Ala Phe Gln Gly Ile Glu His Gln Leu Met Ser Gln Gly
        35                  40                  45

Lys Arg His Leu Glu Gln Leu Arg Thr Val Lys Tyr Arg Pro Ala Leu
    50                  55                  60

Leu Glu Leu Glu Glu Lys Leu Ala Lys Ala Leu His Gln Gln Gly Phe
65                  70                  75                  80

Val Gln Val Val Thr Pro Thr Ile Ile Thr Lys Ser Ala Leu Ala Lys
                85                  90                  95

Met Thr Ile Gly Glu Asp His Pro Leu Phe Ser Gln Val Phe Trp Leu
            100                 105                 110

Asp Gly Lys Lys Cys Leu Arg Pro Met Leu Ala Pro Asn Leu Tyr Thr
        115                 120                 125

Leu Trp Arg Glu Leu Glu Arg Leu Trp Asp Lys Pro Ile Arg Ile Phe
    130                 135                 140

Glu Ile Gly Thr Cys Tyr Arg Lys Glu Ser Gln Gly Ala Gln His Leu
145                 150                 155                 160

Asn Glu Phe Thr Met Leu Asn Leu Thr Glu Leu Gly Thr Pro Leu Glu
                165                 170                 175

Glu Arg His Gln Arg Leu Gly Asp Met Ala Arg Trp Val Leu Glu Ala
            180                 185                 190

Ala Gly Ile Arg Glu Phe Glu Leu Val Thr Glu Ser Ser Val Val Tyr
        195                 200                 205

Gly Asp Thr Val Asp Val Met Lys Gly Asp Leu Glu Leu Ala Ser Gly
    210                 215                 220

Ala Met Gly Pro His Phe Leu Asp Glu Lys Trp Glu Ile Phe Asp Pro
225                 230                 235                 240

Trp Val Gly Leu Gly Phe Gly Leu Glu Arg Leu Leu Met Ile Arg Glu
                245                 250                 255

Gly Thr Gln His Val Gln Ser Met Ala Arg Ser Leu Ser Tyr Leu Asp
            260                 265                 270

Gly Val Arg Leu Asn Ile Asn
        275
```